US012359207B2

(12) United States Patent
Heux et al.

(10) Patent No.: US 12,359,207 B2
(45) Date of Patent: Jul. 15, 2025

(54) SYNTHETIC METHYLOTROPHY

(71) Applicants: INSTITUT NATIONAL DES SCIENCES APPLIQUEES DE TOULOUSE, Toulouse (FR); UNIVERSITE TOULOUSE III-PAUL SABATIER, Toulouse (FR); CENTRE NATIONAL DE LA RECHERCHE SCIENTIFIQUE, Paris (FR); INSTITUT NATIONAL DE LA RECHERCHE AGRONOMIQUE, Paris (FR)

(72) Inventors: Stéphanie Heux, Balma (FR); Alessandro De Simone, Bari (IT); Jean-Charles Portais, Pibrac (FR)

(73) Assignees: INSTITUT NATIONAL DES SCIENCES APPLIQUEES DE TOULOUSE, Toulouse (FR); UNIVERSITE TOULOUSE III-PAUL SABATIER, Toulouse (FR); CENTRE NATIONAL DE LA RECHERCHE SCIENTIFIQUE, Paris (FR); INSTITUT NATIONAL DE RECHERCHE POUR L'AGRICULTURE, L'ALIMENTATION ET L'ENVIRONNEMENT, Paris (FR)

( * ) Notice: Subject to any disclaimer, the term of this patent is extended or adjusted under 35 U.S.C. 154(b) by 1368 days.

(21) Appl. No.: 16/614,878

(22) PCT Filed: Jun. 22, 2018

(86) PCT No.: PCT/EP2018/066762
§ 371 (c)(1),
(2) Date: Nov. 19, 2019

(87) PCT Pub. No.: WO2018/234546
PCT Pub. Date: Dec. 27, 2018

(65) Prior Publication Data
US 2023/0183710 A1 Jun. 15, 2023

(30) Foreign Application Priority Data

Jun. 23, 2017 (EP) ...................... 17305781

(51) Int. Cl.
*C12N 15/52* (2006.01)
*C12N 9/04* (2006.01)
*C12N 9/10* (2006.01)

(52) U.S. Cl.
CPC ........... *C12N 15/52* (2013.01); *C12N 9/0006* (2013.01); *C12N 9/1022* (2013.01); *C12Y 101/01244* (2013.01); *C12Y 202/01001* (2013.01)

(58) Field of Classification Search
CPC .... C12N 15/52; C12N 9/0006; C12N 9/1022; C12Y 101/01244; C12Y 202/01001; C12Y 101/02007; C12Y 202/01003
See application file for complete search history.

(56) References Cited

U.S. PATENT DOCUMENTS

2010/0205690 A1 * 8/2010 Blasing ............. C12N 15/8261
435/417
2016/0060635 A1 3/2016 Liao

FOREIGN PATENT DOCUMENTS

| WO | WO 2013/110797 | 8/2013 | |
|---|---|---|---|
| WO | WO-2013110797 A1 * | 8/2013 | ............. C12N 1/205 |
| WO | WO 2015/013295 | 1/2015 | |
| WO | WO-2015013295 A1 * | 1/2015 | ............... C12N 1/16 |
| WO | WO 2015/051298 | 4/2015 | |
| WO | WO-2015051298 A2 * | 4/2015 | ........... C12N 9/0006 |
| WO | WO 2015/160848 | 10/2015 | |

OTHER PUBLICATIONS

Becker et al. "Advanced biotechnology: metabolically engineered cells for the bio-based production of chemicals and fuels, materials, and health-care products." Angew Chem Int Ed Engl. Mar. 9, 2015;54(11):3328-50. doi: 10.1002/anie.201409033. Epub Feb. 11, 2015. PMID: 25684732. (Year: 2015).*
International Search Report, PCT/EP2018/066762, dated Jul. 30, 2018.
European Search Report, EP 17 30 5781, dated Nov. 7, 2017.
9 Apr. 1, 2015 (Apr. 9, 2015), B. methanolicus NAD(P)+-dependent methanol dehydrogenase protein, SEQ 11. XP002775328, Database accession No. BBX93904, the whole document.

(Continued)

*Primary Examiner* — Neil P Hammell
*Assistant Examiner* — Morgan Taylor Lindgren Baltzel
(74) *Attorney, Agent, or Firm* — NIXON & VANDERHYE

(57) ABSTRACT

Disclosed is a microorganism, which has been engineered to acquire methylotrophy. More particularly, the application describes a non-naturally occurring microorganism, which has been engineered to express or include a first enzyme and a second enzyme, wherein the first enzyme is a methanol dehydrogenase (Mdh) enzyme or a methanol oxidase (Mox) enzyme, and wherein the second enzyme is a dihydroxyacetone synthase (Das) enzyme or a transketolase enzyme. The application also describes element and applications, more particularly kits and methods, which include or use the microorganism.

7 Claims, 4 Drawing Sheets
Specification includes a Sequence Listing.

(56) References Cited

OTHER PUBLICATIONS

Dai Zhongxue et al: "Metabolic construction strategies for direct methanol utilization in *Saccharomyces cerevisiae*", Bioresource Technology, vol. 245, May 19, 2017 (May 19, 2017), pp. 1407-1412, XP085238067, ISSN: 0960-8524, 001: 10.1016/J.BIORTECH. 2017.05.100, the whole document.

Whitaker W Brian et al: "Engineering the biological conversion of methanol to specialty chemicals in *Escherichia coli*", Metabolic Engineering, Academic Press, US, vol. 39, Nov. 1, 2016 (Nov. 1, 2016), pp. 49-59, XP029880989, ISSN: 1096-7176, 001: 10.1016/J.YMBEN.2016.10.015,abstract,figure 1 p. 50, left-hand column paragraph 4—paragraph 5.

Jonas E.N. Muller et al: "Engineering *Escherichia coli* for methanol conversion", Metabolic Engineering, vol. 28, Mar. 1, 2015 (Mar. 1, 2015), pp. 190-201, XP055255408, US ISSN: 1096-7176, 001: 10.1016/j.ymben.2014.12.008, cited in the application, the whole document.

Wenming Zhang et al: "Guidance for engineering of synthetic methylotrophy based on methanol metabolism in methylotrophy", RSC ADV., vol. 7. No. 7, Jan. 1, 2017 (Jan. 1, 2017) pp. 4083-4091. XP055392694, 001: 10.1039/C6RA27038G, the whole document.

Written Opinion, PCT/EP2018/066762, dated Jul. 30, 2018.

Baba et al., "Construction of *Escherichia coli* K-12 in-frame, single-gene knockout mutants: the Keio collection," Molecular systems biology 2006, Article No. 2006.0008, doi:10.1038/msb4100050, 11 pages.

Becker and Wittmann, "Advanced biotechnology: metabolically engineered cells for the bio-based production of chemicals and fuels, materials and healthcare products," Angew. Chem. Int. Ed., 2015, vol. 54, pp. 3328-3350.

Hanahan, "Studies on transformation of *Escherichia coli* with plasmids," Journal of molecular biology, 1983, vol. 166, pp. 557-580.

Hibbert et al., "Directed evolution of transketolase activity on non-phosphorylated substrates," Journal of Biotechnology, 2007, vol. 131, pp. 425-432.

Miyasaki, "Chapter seventeen—MEGAWHOP Cloning: A Method of Creating Random Mutagenesis Libraries via Megaprimer PCR of Whole Plasmids," Methods in Enzymology, 2011, vol. 498, pp. 399-406, https://doi.org/10.1016/B978-0-12-385120-8.00017-6.

MÜLLER et al., "Engineering *Escherichia coli* for methanol conversion," Metabolic Engineering, 2015, vol. 28, pp. 190-201.

Silva-Rocha et al., "The Standard European Vector Architecture (SEVA): a coherent platform for the analysis and deployment of complex prokaryotic phenotypes," Nucleic acids research, 2013, vol. 41 (Database issue), doi:10.1093/har/gks1119, pp. D666-D675.

Sambrook et al., "Molecular cloning: a laboratory manual," Second edition, Fritsch & Maniatis, T., 1989, Cold Spring Harbor, New York: Cold Spring Harbor Laboratory Press, 425 pages.

* cited by examiner

SEQUENCE LISTING

```
<160> NUMBER OF SEQ ID NOS: 65

<210> SEQ ID NO 1
<211> LENGTH: 385
<212> TYPE: PRT
<213> ORGANISM: Bacillus methanolicus

<400> SEQUENCE: 1

Met Thr Asn Thr Gln Ser Ile Phe Tyr Ile Pro Ser Val Asn Leu Phe
1               5                   10                  15

Gly Pro Gly Ser Val Asn Glu Val Gly Thr Arg Leu Ala Gly Leu Gly
            20                  25                  30

Val Lys Lys Ala Leu Leu Val Thr Asp Ala Gly Leu His Gly Leu Gly
        35                  40                  45

Leu Ser Glu Lys Ile Ala Ser Ile Ile Arg Glu Ala Gly Val Glu Val
    50                  55                  60

Leu Ile Phe Pro Lys Ala Glu Pro Asn Pro Thr Asp Lys Asn Val Ala
```

```
            65                  70                  75                  80
        Glu Gly Leu Glu Val Tyr Asn Ala Glu Asn Cys Asp Ser Ile Val Thr
                        85                  90                  95

Leu Gly Gly Gly Ser Ser His Asp Ala Gly Lys Gly Ile Ala Leu Val
                        100                 105                 110

Ala Ala Asn Gly Gly Thr Ile Tyr Asp Tyr Glu Gly Val Asp Lys Ser
                        115                 120                 125

Lys Lys Pro Met Val Pro Leu Ile Ala Ile Asn Thr Thr Ala Gly Thr
        130                 135                 140

Gly Ser Glu Leu Thr Arg Phe Thr Ile Ile Thr Asp Thr Glu Arg Lys
        145                 150                 155                 160

Val Lys Met Ala Ile Val Asp Lys His Val Thr Pro Thr Leu Ser Ile
                        165                 170                 175

Asn Asp Pro Glu Leu Met Val Gly Met Pro Pro Ser Leu Thr Ala Ala
                        180                 185                 190

Thr Gly Leu Asp Ala Leu Thr His Ala Ile Glu Ala Tyr Val Ser Thr
                        195                 200                 205

Ala Ala Thr Pro Ile Thr Asp Ala Leu Ala Ile Gln Ala Ile Lys Ile
                        210                 215                 220

Ile Ser Lys Tyr Leu Pro Arg Ala Phe Ala Asn Gly Lys Asp Met Glu
        225                 230                 235                 240

Ala Arg Glu Gln Met Ala Phe Ala Gln Ser Leu Ala Gly Met Ala Phe
                        245                 250                 255

Asn Asn Ala Ser Leu Gly Tyr Val His Ala Ile Ala His Gln Phe Gly
                        260                 265                 270

Gly Phe Tyr Asn Phe Pro His Gly Val Cys Asn Ala Ile Leu Leu Pro
                        275                 280                 285

His Val Cys Arg Phe Asn Leu Ile Ser Lys Val Glu Arg Phe Ala Glu
                        290                 295                 300

Ile Ala Ala Leu Leu Gly Glu Asn Val Ala Gly Leu Ser Thr Arg Glu
        305                 310                 315                 320

Ala Ala Glu Lys Gly Ile Lys Ala Ile Glu Arg Met Ala Lys Asp Leu
                        325                 330                 335

Asn Ile Pro Arg Gly Phe Lys Glu Leu Gly Ala Lys Glu Glu Asp Ile
                        340                 345                 350

Val Thr Leu Ala Glu Asn Ala Met Lys Asp Ala Thr Ala Leu Thr Asn
                        355                 360                 365

Pro Arg Lys Pro Lys Leu Glu Glu Val Ile Gln Ile Ile Lys Asn Ala
                        370                 375                 380

Met
        385

<210> SEQ ID NO 2
<211> LENGTH: 386
<212> TYPE: PRT
<213> ORGANISM: Bacillus coagulans

<400> SEQUENCE: 2

Met Leu Thr Gly Leu Arg Thr Asp Phe Gln Met Pro Ser Val Asn Leu
1               5                   10                  15

Phe Gly Gln Gly Thr Ala Glu Glu Ile Gly Asn Arg Leu Lys Asn Leu
                20                  25                  30

Gly Cys Arg Arg Pro Leu Ile Val Thr Asp Glu Gly Leu His Gln Leu
                35                  40                  45
```

```
Gly Tyr Ser Glu Lys Ile Ala Ala Tyr Ile Lys Glu Ala Gly Leu Glu
     50                  55                  60

Val Ala Ile Tyr Pro Lys Ala Glu Pro Asn Pro Thr Asp Lys Asn Val
 65                  70                  75                  80

Glu Asp Gly Leu Lys Thr Tyr His Glu Asn Cys Asp Ser Ile Val
                 85                  90                  95

Ser Leu Gly Gly Gly Ser Ala His Asp Cys Ala Lys Gly Ile Gly Leu
                100                 105                 110

Val Ala Ala Asn Gly Gly Lys Ile His Asp Tyr Glu Gly Leu Asp Arg
            115                 120                 125

Ser Glu Lys Pro Met Val Pro Leu Val Ala Ile Asn Thr Thr Ala Gly
    130                 135                 140

Thr Ala Ser Glu Met Thr Lys Phe Thr Ile Ile Thr Asp Thr Ser Arg
145                 150                 155                 160

Lys Val Lys Met Ala Ile Val Asp Lys His Val Thr Pro Val Leu Ser
                165                 170                 175

Ile Asn Asp Pro Leu Leu Met Val Gly Met Pro Pro Ser Leu Thr Ala
            180                 185                 190

Ala Thr Gly Leu Asp Ala Leu Thr His Ala Val Glu Ala Tyr Val Ser
        195                 200                 205

Thr Ala Ala Thr Pro Val Thr Asp Ala Cys Ala Ile Lys Ala Ile Gln
210                 215                 220

Ile Ile Pro Gln Tyr Leu Pro Lys Ala Val Ala Asn Gly Asn Asp Met
225                 230                 235                 240

Glu Ala Arg Glu Gln Met Val Tyr Ala Gln Tyr Leu Ala Gly Met Ala
                245                 250                 255

Phe Asn Asn Ala Ser Leu Gly Tyr Val His Ala Ile Ala His Gln Phe
            260                 265                 270

Gly Gly Phe Tyr Asn Leu Pro His Gly Val Cys Asn Ala Ile Leu Leu
        275                 280                 285

Pro His Val Cys Arg Phe Asn Leu Ile Ala Arg Lys Glu Arg Phe Ala
290                 295                 300

Glu Ile Ala Val Ala Leu Gly Glu Lys Thr Asp Gly Leu Ser Val Asp
305                 310                 315                 320

Glu Ala Ala Glu Lys Ala Ile Thr Ala Ile Glu Arg Leu Ala Ala Gln
                325                 330                 335

Leu Asn Ile Pro Lys Gly Phe Lys Glu Leu Gly Ala Lys Glu Glu Asp
            340                 345                 350

Ile Glu Ile Leu Ala Gln His Ala Met Gln Asp Ala Cys Ala Ala Thr
        355                 360                 365

Asn Pro Arg Lys Pro Thr Gln Lys Glu Val Glu Ala Ile Ile Lys Ala
370                 375                 380

Ala Met
385

<210> SEQ ID NO 3
<211> LENGTH: 390
<212> TYPE: PRT
<213> ORGANISM: Burkholderia

<400> SEQUENCE: 3

Met Ser Tyr Leu Asn Ile Ala Glu Arg Thr Asp Ser Phe Phe Met Pro
1               5                   10                  15

Cys Val Thr Leu Ile Gly Pro Gly Cys Ala Arg Glu Thr Gly Thr Arg
                20                  25                  30
```

Ala Lys Ser Leu Gly Ala Lys Lys Val Leu Ile Val Thr Asp Ala Gly
             35                  40                  45

Leu His Lys Met Gly Leu Ser Glu Ile Ile Ala Gly Tyr Leu Arg Glu
 50                  55                  60

Ala Gly Leu Gln Ala Thr Ile Phe Ala Gly Ala Glu Pro Asn Pro Thr
 65                  70                  75                  80

Asp Leu Asn Val His Asp Gly Val Ala Leu Phe Glu Gln His Gly Cys
                 85                  90                  95

Asp Phe Ile Val Ser Leu Gly Gly Ser Ser His Asp Cys Ala Lys
                100                 105                 110

Gly Ile Gly Leu Val Ser Ala Gly Gly His Ile Arg Asp Tyr Glu
                115                 120                 125

Gly Ile Asp Arg Ser Ser Val Pro Met Thr Pro Leu Ile Ser Ile Asn
130                 135                 140

Thr Thr Ala Gly Thr Ala Ala Glu Met Thr Arg Phe Cys Ile Ile Thr
145                 150                 155                 160

Asn Ser Ser Asn His Val Lys Met Ala Ile Val Asp Trp Arg Ser Thr
                165                 170                 175

Pro Leu Val Ala Ile Asp Asp Pro Arg Leu Met Val Ala Met Pro Pro
                180                 185                 190

Ala Leu Thr Ala Ala Thr Gly Met Asp Ala Leu Thr His Ala Val Glu
                195                 200                 205

Ala Tyr Val Ser Thr Ala Ala Thr Pro Ile Thr Asp Ala Cys Ala Glu
                210                 215                 220

Lys Ala Ile Ala Leu Ile Gly Gln Trp Leu Pro Lys Ala Val Ala Asn
225                 230                 235                 240

Gly Glu Ser Met Glu Ala Arg Ala Ala Met Cys Tyr Ala Gln Tyr Leu
                245                 250                 255

Ala Gly Met Ala Phe Asn Asn Ala Ser Leu Gly Tyr Val His Ala Met
                260                 265                 270

Ala His Gln Leu Gly Gly Phe Tyr Asn Leu Pro His Gly Val Cys Asn
                275                 280                 285

Ala Ile Leu Leu Pro His Val Cys Glu Phe Asn Leu Ile Ala Ala Pro
                290                 295                 300

Glu Arg Phe Ala Ala Ile Ala Ser Leu Leu Gly Ala Ser Thr Pro Gly
305                 310                 315                 320

Leu Ser Thr Thr Glu Ala Ala Arg Ala Ala Ile Ala Ile Arg Ser
                325                 330                 335

Leu Ser Ala Ser Ile Gly Ile Pro Ser Gly Leu Ala Gly Leu Gly Val
                340                 345                 350

Lys Ala Asp Asp His Glu Val Met Ala His Asn Ala Gln Lys Asp Ala
                355                 360                 365

Cys Met Leu Thr Asn Pro Arg Lys Ala Ser Val Ala Gln Val Ile Ala
370                 375                 380

Ile Phe Glu Ala Ala Met
385                 390

<210> SEQ ID NO 4
<211> LENGTH: 390
<212> TYPE: PRT
<213> ORGANISM: Acinetobacter gerneri

<400> SEQUENCE: 4

Met Ala Phe Lys Asn Leu Ala Asp Gln Thr Asn Gly Phe Tyr Ile Pro

```
  1               5                  10                 15
Cys Val Ser Leu Phe Gly Pro Gly Cys Ala Lys Glu Val Gly Ala Lys
             20                 25                 30

Ala Gln Asn Leu Gly Ala Lys Lys Ala Leu Ile Val Thr Asp Ala Gly
             35                 40                 45

Leu Phe Lys Phe Gly Val Ala Asp Ile Ile Val Gly Tyr Leu Lys Asp
             50                 55                 60

Ala Gly Val Asp Ser His Val Phe Pro Gly Ala Glu Pro Asn Pro Thr
 65              70                 75                 80

Asp Ile Asn Val Leu Asn Gly Val Gln Ala Tyr Asn Asp Asn Gly Cys
                 85                 90                 95

Asp Phe Ile Val Ser Leu Gly Gly Ser Ser His Asp Cys Ala Lys
                100                105                110

Gly Ile Gly Leu Val Thr Ala Gly Gly Asn Ile Arg Asp Tyr Glu
                115                120                125

Gly Ile Asp Lys Ser Ser Val Pro Met Thr Pro Leu Ile Ala Ile Asn
                130                135                140

Thr Thr Ala Gly Thr Ala Ser Glu Met Thr Arg Phe Cys Ile Ile Thr
145                150                155                160

Asn Thr Asp Thr His Val Lys Met Ala Ile Val Asp Trp Arg Cys Thr
                165                170                175

Pro Leu Val Ala Ile Asp Asp Pro Lys Leu Met Ile Ala Lys Pro Ala
                180                185                190

Ala Leu Thr Ala Ala Thr Gly Met Asp Ala Leu Thr His Ala Val Glu
                195                200                205

Ala Tyr Val Ser Thr Ala Ala Asn Pro Ile Thr Asp Ala Cys Ala Glu
                210                215                220

Lys Ala Ile Ser Met Ile Ser Glu Trp Leu Ser Ser Ala Val Ala Asn
225                230                235                240

Gly Glu Asn Ile Glu Ala Arg Asp Ala Met Ala Tyr Ala Gln Tyr Leu
                245                250                255

Ala Gly Met Ala Phe Asn Asn Ala Ser Leu Gly Tyr Val His Ala Met
                260                265                270

Ala His Gln Leu Gly Gly Phe Tyr Asn Leu Pro His Gly Val Cys Asn
                275                280                285

Ala Ile Leu Leu Pro His Val Cys Glu Phe Asn Leu Ile Ala Cys Pro
                290                295                300

Asp Arg Phe Ala Lys Ile Ala Gln Leu Met Gly Val Asp Thr Thr Gly
305                310                315                320

Met Thr Val Thr Glu Ala Gly Tyr Glu Ala Ile Ala Ala Ile Arg Glu
                325                330                335

Leu Ser Ala Ser Ile Gly Ile Pro Ser Gly Leu Thr Glu Leu Gly Val
                340                345                350

Lys Ala Ala Asp His Ala Val Met Thr Ser Asn Ala Gln Lys Asp Ala
                355                360                365

Cys Met Leu Thr Asn Pro Arg Lys Ala Thr Asp Ala Gln Val Ile Ala
                370                375                380

Ile Phe Glu Ala Ala Met
385                390
```

<210> SEQ ID NO 5
<211> LENGTH: 389
<212> TYPE: PRT
<213> ORGANISM: Herbaspirillum rubrisubalbicans

<400> SEQUENCE: 5

```
Met Ala Met Ala Asn Gln Thr Phe Gly Phe Tyr Met Pro Asn Val Ser
1               5                   10                  15

Leu Met Gly Val Gly Cys Ala Glu Val Gly Leu Gln Ala Lys Ala
            20                  25                  30

Leu Gly Ala Arg Arg Val Phe Leu Cys Thr Asp Val Gly Met Val Lys
            35                  40                  45

Leu Gly Met Ala Asn Lys Ile Lys Ala Ile Leu Glu Ser Ala Asp Leu
50                  55                  60

Ala Val Thr Val Tyr Asp Gly Ser Asp Pro Asn Pro Thr Asp Lys Asn
65                  70                  75                  80

Val Glu Leu Gly Val Gln Leu Tyr Arg Ala Ala Asp Cys Asp Ala Ile
                85                  90                  95

Val Ser Leu Gly Gly Gly Ser Ala His Asp Cys Ala Lys Gly Ile Gly
            100                 105                 110

Met Val Val Ser Asn Gly Gly Asn Ile Arg Asp Tyr Glu Gly Leu Asn
            115                 120                 125

Lys Thr Ser Lys Pro Met Pro Pro Phe Leu Ala Ile Asn Thr Thr Ala
130                 135                 140

Gly Thr Ala Ser Glu Met Thr Arg Phe Cys Ile Ile Thr Asn Thr Asp
145                 150                 155                 160

Asn His Val Lys Met Ala Leu Val Asp Trp Arg Cys Thr Pro Asn Val
                165                 170                 175

Ala Ile Asn Asp Pro Leu Leu Met Lys Asp Met Pro Ala Ser Leu Thr
            180                 185                 190

Ala Ala Thr Gly Met Asp Ala Leu Thr His Ala Ile Glu Ala Tyr Val
            195                 200                 205

Ser Thr Ala Ala Thr Pro Ile Thr Asp Ala Cys Ala Leu Gln Ala Ile
210                 215                 220

Arg Leu Ile Ser Gln Trp Leu Arg Pro Ala Val Ala Asn Ala Gln Gln
225                 230                 235                 240

Met Glu Ala Arg Asp Lys Met Ala Tyr Ala Glu Tyr Leu Ala Gly Met
                245                 250                 255

Ala Phe Asn Asn Ala Ser Leu Gly Tyr Val His Ala Met Ala His Gln
            260                 265                 270

Leu Gly Gly Phe Tyr Asn Leu Pro His Gly Val Cys Asn Ala Ile Leu
            275                 280                 285

Leu Pro Glu Val Cys Ser Phe Asn Leu Ile Ala Cys Pro Gln Arg Tyr
290                 295                 300

Ala Asp Ile Ala Glu Ala Met Gly Glu Lys Ile Ala Asn Leu Ser Val
305                 310                 315                 320

Met Asp Ala Ala Asp Lys Ala Ile Lys Ala Ile Arg Gln Leu Ala Arg
                325                 330                 335

Asp Val Ala Ile Pro Pro Asn Leu Ala Val Leu Gly Val Lys Glu Ser
            340                 345                 350

Asp Phe Glu Leu Met Ala Thr Asn Ala Lys Lys Asp Ala Cys Gln Leu
            355                 360                 365

Thr Asn Pro Arg Thr Ala Thr Leu Glu Gln Val Val Gly Ile Phe Arg
370                 375                 380

Gln Ala His Gln Gly
385
```

<210> SEQ ID NO 6
<211> LENGTH: 382
<212> TYPE: PRT
<213> ORGANISM: Wohlfahrtiimonas chitiniclastica

<400> SEQUENCE: 6

```
Met Ala Thr Gln Phe Leu Met Pro Ser Lys Asn Ile Met Gly Ala Gly
1               5                   10                  15

Ala Leu Asp Leu Ala Tyr Asp Asp Ile Lys Ala Gln Gly Phe Lys Lys
            20                  25                  30

Ile Leu Ile Val Ser Asp Glu Gly Leu Lys Gly Ala Gly Ile Ile Asp
        35                  40                  45

Leu Val Val Lys Gly Leu Lys Asp Lys Gly Ile Glu Ser Ala Val Tyr
    50                  55                  60

Ser Gly Thr Lys Pro Asn Pro Thr Thr Lys Asn Val Glu Glu Gly Leu
65                  70                  75                  80

Ala Ile Leu Lys Ala Glu His Cys Asp Ala Ile Ile Ser Leu Gly Gly
                85                  90                  95

Gly Ser Pro His Asp Cys Ala Lys Gly Ile Ala Leu Val Ala Ala Asn
            100                 105                 110

Gly Gly Lys Ile Asn Asp Tyr Glu Gly Ile Asn Lys Ser Ala Lys Pro
        115                 120                 125

Gln Leu Pro Leu Ile Ala Ile Asn Thr Thr Ala Gly Thr Ala Ser Glu
    130                 135                 140

Met Thr Tyr Phe Cys Ile Ile Thr Asp Glu Ser Arg His Ile Lys Met
145                 150                 155                 160

Ala Ile Val Asp Ala His Thr Thr Pro Leu Leu Ser Val Asn Asp Pro
                165                 170                 175

Glu Leu Met Lys Gly Met Pro Lys Ser Leu Thr Ala Ala Thr Gly Met
            180                 185                 190

Asp Ala Leu Thr His Ala Val Glu Ala Tyr Val Ser Thr Ala Ala Thr
        195                 200                 205

Pro Ile Thr Asp Ala Cys Ala Val Lys Ala Val Ala Leu Ile His Lys
    210                 215                 220

Asn Leu Arg Asp Ala Val Asn Asp Gly Ala Asn Met His Ala Arg Glu
225                 230                 235                 240

Gln Met Ala Tyr Ala Gln Phe Leu Ala Gly Met Ala Phe Asn Asn Ala
                245                 250                 255

Ser Leu Gly Tyr Val His Ala Met Ala His Gln Leu Gly Gly Phe Tyr
            260                 265                 270

Asp Leu Pro His Gly Val Cys Asn Ala Val Leu Leu Pro His Val Gln
        275                 280                 285

Glu Tyr Asn Ala Lys Val Ala Ala Gly Arg Leu Lys Asp Leu Ala Ala
    290                 295                 300

Cys Phe Asp Ile Asp Thr Arg Ala Met Ser Asp Glu Gly Ala Lys
305                 310                 315                 320

Ala Leu Ile Ala Ala Ile Arg Thr Leu Ser Gln Asp Val Gly Ile Pro
                325                 330                 335

Ala Gly Leu Lys Asp Leu Gly Ala Lys Glu Glu Asp Phe Thr Ile Leu
            340                 345                 350

Ala Glu Asn Ala Leu Lys Asp Ala Cys Ser Phe Thr Asn Pro Arg Lys
        355                 360                 365

Gly Asp Glu Ala Glu Val Ile Ala Ile Phe Lys Ala Ala Phe
    370                 375                 380
```

<210> SEQ ID NO 7
<211> LENGTH: 382
<212> TYPE: PRT
<213> ORGANISM: Pseudomonas lini

<400> SEQUENCE: 7

```
Met Ser Ser Thr Phe Phe Ile Pro Ala Val Asn Ile Met Gly Thr Gly
1               5                   10                  15
Cys Leu Asp Glu Ala Met Asp Ala Ile Arg Lys Tyr Gly Phe Arg Lys
            20                  25                  30
Ala Leu Ile Val Thr Asp Thr Gly Leu Ala Lys Ala Gly Val Ala Thr
        35                  40                  45
Met Ile Ala Gly Lys Leu Ala Leu Gln Asp Ile Asp Ser Val Ile Phe
50                  55                  60
Asp Gly Ala Lys Pro Asn Pro Ser Ile Ala Asn Val Glu Leu Gly Leu
65                  70                  75                  80
Gly Leu Leu Lys Glu Ser Arg Cys Asp Phe Val Val Ser Leu Gly Gly
                85                  90                  95
Gly Ser Pro His Asp Cys Ala Lys Gly Ile Ala Leu Cys Ala Thr Asn
            100                 105                 110
Gly Gly Thr Ile Arg Asp Tyr Glu Gly Val Asp Gln Ser Ala Lys Pro
        115                 120                 125
Gln Met Pro Leu Ile Ala Ile Asn Thr Thr Ala Gly Thr Ala Ser Glu
130                 135                 140
Met Thr Arg Phe Cys Ile Ile Thr Asp Glu Ser Arg His Val Lys Met
145                 150                 155                 160
Ala Ile Val Asp Arg Asn Val Thr Pro Leu Leu Ser Val Asn Asp Pro
                165                 170                 175
Ala Leu Met Val Ala Met Pro Lys Gly Leu Thr Ala Thr Gly Met
            180                 185                 190
Asp Ala Leu Thr His Ala Ile Glu Ala Tyr Val Ser Thr Ala Ala Asn
        195                 200                 205
Pro Ile Thr Asp Ala Cys Ala Leu Lys Ala Ile Thr Leu Ile Ser Asn
210                 215                 220
Asn Leu Arg Leu Ala Val Arg Asp Gly Ser Asp Met Ile Ala Arg Glu
225                 230                 235                 240
Asn Met Ala Tyr Ala Gln Phe Leu Ala Gly Met Ala Phe Asn Asn Ala
                245                 250                 255
Ser Leu Gly Tyr Val His Ala Met Ala His Gln Leu Gly Gly Phe Tyr
            260                 265                 270
Asp Leu Pro His Gly Val Cys Asn Ala Val Leu Leu Pro His Val Gln
        275                 280                 285
Ser Phe Asn Ala Leu Val Cys Ala Asp Arg Leu Thr Asp Val Ala Arg
290                 295                 300
Ala Met Gly Ala Asp Ile Arg Gly Phe Ser Pro Glu Glu Gly Ala Gln
305                 310                 315                 320
Ala Ala Ile Ala Ala Ile Arg Asn Leu Ala Lys Asp Val Glu Ile Pro
                325                 330                 335
Ala Gly Leu Arg Glu Leu Gly Thr Lys Leu Thr Asp Ile Pro Val Leu
            340                 345                 350
Ala Ser Asn Ala Met Lys Asp Ala Cys Gly Leu Thr Asn Pro Arg Lys
        355                 360                 365
Ala Asp Gln Arg Gln Ile Glu Glu Ile Phe Arg Ser Ala Phe
370                 375                 380
```

<210> SEQ ID NO 8
<211> LENGTH: 384
<212> TYPE: PRT
<213> ORGANISM: Paenibacillus

<400> SEQUENCE: 8

```
Met Thr Gly Thr Ser Lys Phe Met Met Pro Gly Met Ser Leu Met Gly
1               5                   10                  15

Ser Gly Ala Leu Ala Asp Ala Gly Thr Glu Ile Gly Lys Leu Gly Phe
            20                  25                  30

Lys Asn Ala Leu Ile Val Thr Asp Lys Pro Leu Val Asp Ile Gly Ile
        35                  40                  45

Val Glu Lys Val Thr Thr Met Leu Glu Ser His Asn Val Lys Ser Val
50                  55                  60

Val Tyr Ser Gly Thr Gln Pro Asn Pro Thr Val Ser Asn Val Asn Glu
65                  70                  75                  80

Gly Leu Ala Leu Leu Lys Gln Ser Gly Cys Asp Phe Ile Ile Ser Leu
                85                  90                  95

Gly Gly Gly Ser Pro His Asp Cys Ala Lys Gly Ile Ala Leu Leu Ala
            100                 105                 110

Ser Asn Gly Gly Gln Ile Gly Asp Tyr Glu Gly Val Asp Lys Ser Gly
        115                 120                 125

Lys Pro Ser Phe Pro Leu Ile Ala Ile Asn Thr Thr Ala Gly Thr Ala
130                 135                 140

Ser Glu Met Thr Met Phe Cys Ile Ile Thr Asp Glu Glu Arg His Ile
145                 150                 155                 160

Lys Met Ala Ile Val Asp Lys His Thr Thr Pro Leu Ile Ala Val Asn
                165                 170                 175

Asp Pro Asp Leu Met Met Ala Met Pro Lys Ser Leu Thr Ala Ala Thr
            180                 185                 190

Gly Met Asp Ala Leu Thr His Ser Ile Glu Ala Tyr Val Ser Thr Asn
        195                 200                 205

Ala Thr Pro Ile Thr Asp Ala Cys Ala Leu Lys Ala Ile Glu Leu Ile
210                 215                 220

Arg Asp His Leu Val Lys Ala Val Asp Asp Gly Asn Asp Val Glu Ala
225                 230                 235                 240

Arg Ser Gln Met Ala Tyr Ala Glu Phe Leu Ala Gly Met Ala Phe Asn
                245                 250                 255

Asn Ala Gly Leu Gly Phe Val His Ala Met Ala His Gln Leu Gly Gly
            260                 265                 270

Phe Tyr Asn Leu Pro His Gly Val Cys Asn Ala Ile Leu Leu Pro His
        275                 280                 285

Val Glu Arg Tyr Asn Ala Lys Ala Ser Ala Glu Arg Leu Thr Asp Ile
290                 295                 300

Ala Arg Thr Leu Gly Glu Lys Thr Asp Gly Val Thr Pro Glu Gln Gly
305                 310                 315                 320

Ala Asn Leu Ala Leu His Ala Ile Glu Lys Leu Ala Lys Arg Val Asn
                325                 330                 335

Ile Pro Ser Gly Leu Glu Glu Leu Gly Val Lys Arg Glu Asp Phe Ala
            340                 345                 350

Val Leu Ala Ala Asn Ala Leu Lys Asp Ala Cys Gly Ala Thr Asn Pro
        355                 360                 365

Ile Gln Pro Thr Gln Gln Glu Val Ile Asp Ile Phe Glu Gln Ala Met
```

```
                370                 375                 380

<210> SEQ ID NO 9
<211> LENGTH: 382
<212> TYPE: PRT
<213> ORGANISM: Photobacterium damselae

<400> SEQUENCE: 9

Met Ser Ser Ala Phe Tyr Ile Pro Thr Val Asn Phe Met Gly Ala Gly
1               5                   10                  15

Cys Leu Thr Gln Ala Ala Asp Ala Ile Lys Ser His Gly Phe Lys Lys
            20                  25                  30

Ala Leu Ile Val Thr Asp Lys Val Leu Asn Gln Ile Gly Val Val Thr
        35                  40                  45

Gln Val Ala Val Leu Leu Thr Glu Arg Asp Ile Asp Ser Val Val Tyr
    50                  55                  60

Asp Gly Thr Gln Pro Asn Pro Thr Ile Lys Asn Val Asp Glu Gly Leu
65                  70                  75                  80

Ala Leu Leu Lys Glu Asn Gln Cys Asp Phe Val Ile Ser Leu Gly Gly
                85                  90                  95

Gly Ser Pro His Asp Cys Ala Lys Gly Ile Ala Leu Leu Ala Ala Asn
            100                 105                 110

Gly Gly His Ile Gly Asp Tyr Glu Gly Val Asp Arg Ser Ala Lys Ala
        115                 120                 125

Gln Leu Pro Val Val Ala Ile Asn Thr Thr Ala Gly Thr Ala Ser Glu
    130                 135                 140

Met Thr Arg Phe Cys Ile Ile Thr Asp Glu Glu Arg His Ile Lys Met
145                 150                 155                 160

Ala Ile Val Asp Lys Asn Thr Thr Pro Leu Ile Ser Val Asn Asp Pro
                165                 170                 175

Gln Leu Met Leu Ala Lys Pro Ala Ser Leu Thr Ala Ala Thr Gly Met
            180                 185                 190

Asp Ala Leu Thr His Ala Ile Glu Ala Tyr Val Ser Thr Ala Ala Thr
        195                 200                 205

Pro Ile Thr Asp Ala Val Ala Ile Lys Ala Ile Glu Leu Ile Gln Gln
    210                 215                 220

Asn Leu Arg Thr Ala Val Lys Asp Gly Gln Asn Leu Asn Ala Arg Glu
225                 230                 235                 240

Gln Met Ala Tyr Ala Gln Phe Met Ala Gly Met Ala Phe Asn Asn Ala
                245                 250                 255

Ser Leu Gly Tyr Val His Ala Met Ala His Gln Leu Gly Gly Tyr Tyr
            260                 265                 270

Asn Leu Pro His Gly Val Cys Asn Ala Val Leu Leu Pro His Val Gln
        275                 280                 285

Arg Tyr Asn Ala Gln Val Ser Ala Glu Arg Leu Arg Asp Val Ala Lys
    290                 295                 300

Ala Met Gly Val Asp Val Glu Gly Met Thr Ala Glu Gln Gly Ala Asn
305                 310                 315                 320

Ala Ala Leu Glu Ala Ile Val Ala Leu Ser Lys Asp Val Gly Ile Pro
                325                 330                 335

Leu Gly Leu Lys Glu Leu Gly Val Lys Glu Glu Asp Ile Ala Leu Leu
            340                 345                 350

Ala Asp Asn Ala Leu Lys Asp Ala Cys Gly Phe Thr Asn Pro Lys Gln
        355                 360                 365
```

```
Ala Thr His Glu Glu Ile Ser Gln Ile Phe Met Ala Ala Met
    370                 375                 380

<210> SEQ ID NO 10
<211> LENGTH: 382
<212> TYPE: PRT
<213> ORGANISM: Vibrio

<400> SEQUENCE: 10

Met Ser Asn Ala Phe Tyr Ile Pro Ser Leu Asn Leu Met Gly Val Gly
1               5                   10                  15

Cys Leu Glu Glu Ala Val Asn Ala Ile Lys Ser His Gly Phe Thr Lys
            20                  25                  30

Ala Leu Ile Val Thr Asp Lys Val Leu Asn Glu Leu Gly Ala Val Ser
        35                  40                  45

Lys Leu Thr Ser Leu Leu Asp Ser Ala Asn Val Ala Ala Val Val Phe
    50                  55                  60

Tyr Glu Thr Lys Pro Asn Pro Thr Ile Glu Asn Val Asn Asp Gly Leu
65                  70                  75                  80

Ala Leu Leu Lys Gly Asn Gln Cys Asp Cys Val Ile Ser Phe Gly Gly
                85                  90                  95

Gly Ser Pro His Asp Cys Ala Lys Gly Ile Ala Leu Leu Ala Thr Asn
            100                 105                 110

Gly Gly Glu Ile Lys Asp Tyr Glu Gly Val Asp Val Ser Ala Lys Pro
        115                 120                 125

Gln Leu Pro Leu Ile Ser Ile Asn Thr Thr Ala Gly Thr Ala Ser Glu
    130                 135                 140

Met Thr Arg Phe Cys Ile Ile Thr Asp Glu Ala Arg His Ile Lys Met
145                 150                 155                 160

Ala Ile Val Asp Lys Asn Val Thr Pro Ile Ile Ser Val Asn Asp Pro
                165                 170                 175

Glu Leu Met Leu Ala Lys Pro Ala Ser Leu Thr Ala Ala Thr Gly Met
            180                 185                 190

Asp Ala Leu Thr His Ala Ile Glu Ala Tyr Val Ser Ile Ala Ala Thr
        195                 200                 205

Pro Val Thr Asp Ala Val Ala Ile Lys Ala Ile Glu Met Val Gln Ala
    210                 215                 220

Asn Leu Arg Glu Ala Val Gln Asn Gly Asp Asn Leu Thr Ala Arg Asp
225                 230                 235                 240

Asn Met Ala Tyr Ala Gln Phe Met Ala Gly Met Ala Phe Asn Asn Ala
                245                 250                 255

Ser Leu Gly Tyr Val His Ala Ile Ala His Gln Leu Gly Gly Phe Tyr
            260                 265                 270

Asp Leu Pro His Gly Val Cys Asn Ala Ile Leu Leu Pro His Val Gln
        275                 280                 285

Gln Tyr Asn Ala Lys Val Val Pro Ala Arg Leu Ala Asp Val Ala Arg
    290                 295                 300

Ala Met Gly Val Asp Thr Asn Gly Met Thr Asp Glu Gln Ala Ala Asn
305                 310                 315                 320

Ala Gly Leu Asp Ala Ile Arg Gln Leu Ser Lys Asp Val Asn Ile Pro
                325                 330                 335

Ala Gly Leu Glu Gln Leu Gly Val Lys Arg Asp Asp Phe Asp Val Leu
            340                 345                 350

Ala Glu Asn Ala Leu Lys Asp Ala Cys Gly Phe Thr Asn Pro Lys Gln
        355                 360                 365
```

```
Ala Ser His Glu Glu Ile Val Ala Ile Leu Asp Ser Ala Leu
    370                 375                 380
```

<210> SEQ ID NO 11
<211> LENGTH: 382
<212> TYPE: PRT
<213> ORGANISM: Vibrio

<400> SEQUENCE: 11

```
Met Ser Ser Ser Ile Ile Leu Pro Ser Thr Asn Leu Leu Gly Ser Gly
1               5                   10                  15

Cys Leu Ser Gln Ala Val Asp Thr Ile His Gln Gln Gly Phe Ser Lys
            20                  25                  30

Ala Leu Ile Val Thr Asp Ala Val Leu Thr Gln Ile Gly Leu Val Ala
        35                  40                  45

Thr Ile Thr Glu Gln Leu Ala Ala Lys Gly Met Ser Phe Ala Ile Tyr
    50                  55                  60

Asp Gly Thr Gln Pro Asn Pro Thr Ile Asp Asn Val Glu Gln Gly Leu
65                  70                  75                  80

Ser Thr Leu Val Asp Asn Asp Cys Asp Leu Ile Ile Ser Val Gly Gly
                85                  90                  95

Gly Ser Pro His Asp Cys Ala Lys Gly Ile Ala Leu Val Ala Thr Asn
            100                 105                 110

Gly Gly Lys Ile Thr Asp Tyr Glu Gly Ile Asn Lys Ala Ser Lys Ser
        115                 120                 125

Pro Phe Pro Leu Val Ala Ile Asn Thr Thr Ala Gly Thr Ala Ser Glu
    130                 135                 140

Met Thr Met Phe Ser Val Ile Thr Asp Glu Ser Arg Gln Ile Lys Met
145                 150                 155                 160

Ala Ile Val Asp Gln Lys Val Thr Pro Leu Ile Ser Val Asn Asp Pro
                165                 170                 175

Gln Leu Met Leu Ala Met Pro Ser Ser Leu Ser Ala Ala Thr Gly Met
            180                 185                 190

Asp Ala Leu Thr His Ala Ile Glu Ala Tyr Val Ser Val Ala Ala Asn
        195                 200                 205

Pro Ile Thr Asp Thr Val Ala Leu Lys Ala Ile Glu Leu Ile Thr Lys
    210                 215                 220

His Leu Pro Thr Cys Val Ser Asn Gly Ser Asn Leu Glu Ala Arg Glu
225                 230                 235                 240

Gln Met Ala Tyr Ala Gln Phe Met Ala Gly Met Ala Phe Asn Asn Ala
                245                 250                 255

Leu Leu Gly Tyr Val His Ala Met Ala His Gln Leu Gly Ala Thr Tyr
            260                 265                 270

His Leu Pro His Gly Ile Cys Asn Ala Val Leu Leu Pro His Val Gln
        275                 280                 285

Arg Phe Asn Leu Thr Ala Asn Pro Glu Lys Phe Val Asp Ile Ala Gln
    290                 295                 300

Ala Met Gly Lys Glu Val His Gly Leu Thr Thr Glu Glu Ala Ser Gln
305                 310                 315                 320

Leu Ala Ile Glu Ala Met Asn Glu Leu Ala Arg Lys Val Asn Ile Pro
                325                 330                 335

Ala Thr Leu Ala Glu Leu Gly Val Asn Gln Gly Asp Ile Asp Lys Leu
            340                 345                 350

Ser Glu Ser Thr Leu Asn Asp Val Cys Cys Leu Thr Asn Pro Arg Gln
```

355                 360                 365
Ala Thr Lys Gln Glu Ile Ala Glu Ile Phe Gln Ala Ala Trp
    370                 375                 380

<210> SEQ ID NO 12
<211> LENGTH: 382
<212> TYPE: PRT
<213> ORGANISM: Virgibacillus pantothenticus

<400> SEQUENCE: 12

Met Ser Lys Val Leu Tyr Val Pro Ser Ile Asn Leu Ile Gly Arg Gly
1               5                   10                  15

Cys Leu Ala Glu Val Gly Pro Phe Ile Glu Glu Leu Gly Phe Lys Lys
                20                  25                  30

Ala Leu Leu Val Thr Asp Lys Phe Leu Asn Glu Ser Gly Ile Ala Gln
            35                  40                  45

Arg Val Leu Asp Gln Leu Asp Lys Ile Gly Val Ser Tyr Val Val Tyr
        50                  55                  60

Asp Glu Val Lys Pro Asn Pro Thr Thr Lys Asn Val His Asp Gly Val
65                  70                  75                  80

Glu Val Phe Lys Asn Asn Cys Asp Phe Ile Ile Ser Val Gly Gly
                85                  90                  95

Gly Ser Pro Gln Asp Ala Ala Lys Gly Ile Gly Leu Val Val Thr Asn
            100                 105                 110

Gly Gly His Val Arg Asp Tyr Glu Gly Val Gly Lys Thr Lys Tyr Lys
        115                 120                 125

Ala Val Pro Thr Ile Ala Val Asn Thr Thr Ala Gly Thr Ser Ala Glu
    130                 135                 140

Tyr Thr Ile Asn Tyr Val Ile Thr Asp Glu Asp Arg Glu Val Lys Met
145                 150                 155                 160

Val Met Val Asp Lys Asn Ser Leu Val Thr Ile Thr Val Asn Asp Pro
                165                 170                 175

Glu Leu Met Met Gly Lys Pro Lys Asp Leu Thr Ala Ala Thr Gly Met
            180                 185                 190

Asp Ala Leu Thr His Ala Met Glu Ala Ile Val Thr Pro Gly Ala Tyr
        195                 200                 205

Pro Ile Thr Asp Ala Thr Ala Leu Ala Ala Val Glu Ile Ile Phe Glu
    210                 215                 220

Tyr Leu Pro Arg Ala Val Lys Asp Ser Thr Asp Ile Glu Ala Arg Glu
225                 230                 235                 240

Gln Met Val Tyr Val Met Phe Leu Ala Gly Val Ala Phe Asn Asn Ala
                245                 250                 255

Gly Leu Gly Tyr Val His Ala Met Ala His Gln Leu Gly Gly Val Tyr
            260                 265                 270

Asp Leu Pro His Gly Val Cys Asn Ala Met Leu Leu Pro Ile Val Glu
        275                 280                 285

Arg Glu Asn Ala Lys Arg Asp Pro Ser Lys Phe Arg Ala Ile Ala Lys
    290                 295                 300

Ala Ala Gly Ile Asp Ile Thr Asp Lys Thr Asp Glu Gln Cys Ala Ser
305                 310                 315                 320

Ala Val Ile Lys Ala Ile Lys Lys Leu Ser Asn Glu Val Gly Ile Pro
                325                 330                 335

Ser Lys Leu Ser Glu Leu Gly Val Lys Glu Val Asp Leu Glu Lys Leu
            340                 345                 350

```
Ala Asn Asn Ala Met Lys Asp Ala Cys Ala Pro Gly Asn Pro Phe Gln
            355                 360                 365

Pro Thr Lys Asp Glu Val Ile Ser Met Phe Lys Glu Ile Leu
    370                 375                 380

<210> SEQ ID NO 13
<211> LENGTH: 339
<212> TYPE: PRT
<213> ORGANISM: Bacillus stearothermophilus

<400> SEQUENCE: 13

Met Lys Ala Ala Val Val Asn Glu Phe Lys Lys Ala Leu Glu Ile Lys
1               5                   10                  15

Glu Val Glu Arg Pro Lys Leu Glu Glu Gly Glu Val Leu Val Lys Ile
            20                  25                  30

Glu Ala Cys Gly Val Cys His Thr Asp Leu His Ala Ala His Gly Asp
        35                  40                  45

Trp Pro Ile Lys Pro Lys Leu Pro Leu Ile Pro Gly His Glu Gly Val
    50                  55                  60

Gly Ile Val Val Glu Val Ala Lys Gly Val Lys Ser Ile Lys Val Gly
65                  70                  75                  80

Asp Arg Val Gly Ile Pro Trp Leu Tyr Ser Ala Cys Gly Glu Cys Glu
                85                  90                  95

Tyr Cys Leu Thr Gly Gln Glu Thr Leu Cys Pro His Gln Leu Asn Gly
            100                 105                 110

Gly Tyr Ser Val Asp Gly Gly Tyr Ala Glu Tyr Cys Lys Ala Pro Ala
        115                 120                 125

Asp Tyr Val Ala Lys Ile Pro Asp Asn Leu Asp Pro Val Glu Val Ala
    130                 135                 140

Pro Ile Leu Cys Ala Gly Val Thr Thr Tyr Lys Ala Leu Lys Val Ser
145                 150                 155                 160

Gly Ala Arg Pro Gly Glu Trp Val Ala Ile Tyr Gly Ile Gly Gly Leu
                165                 170                 175

Gly His Ile Ala Leu Gln Tyr Ala Lys Ala Met Gly Leu Asn Val Val
            180                 185                 190

Ala Val Asp Ile Ser Asp Glu Lys Ser Lys Leu Ala Lys Asp Leu Gly
        195                 200                 205

Ala Asp Ile Ala Ile Asn Gly Leu Lys Glu Asp Pro Val Lys Ala Ile
    210                 215                 220

His Asp Gln Val Gly Gly Val His Ala Ala Ile Ser Val Ala Val Asn
225                 230                 235                 240

Lys Lys Ala Phe Glu Gln Ala Tyr Gln Ser Val Lys Arg Gly Gly Thr
                245                 250                 255

Leu Val Val Val Gly Leu Pro Asn Ala Asp Leu Pro Ile Pro Ile Phe
            260                 265                 270

Asp Thr Val Leu Asn Gly Val Ser Val Lys Gly Ser Ile Val Gly Thr
        275                 280                 285

Arg Lys Asp Met Gln Glu Ala Leu Asp Phe Ala Ala Arg Gly Lys Val
    290                 295                 300

Arg Pro Ile Val Glu Thr Ala Glu Leu Glu Glu Ile Asn Glu Val Phe
305                 310                 315                 320

Glu Arg Met Glu Lys Gly Lys Ile Asn Gly Arg Ile Val Leu Lys Leu
                325                 330                 335

Lys Glu Asp
```

<210> SEQ ID NO 14
<211> LENGTH: 664
<212> TYPE: PRT
<213> ORGANISM: Pichia angusta

<400> SEQUENCE: 14

```
Met Ala Ile Pro Asp Glu Phe Asp Ile Ile Val Gly Gly Gly Ser
1               5                   10                  15

Thr Gly Cys Cys Ile Ala Gly Arg Leu Ala Asn Leu Asp Asp Gln Asn
            20                  25                  30

Leu Thr Val Ala Leu Ile Glu Gly Gly Glu Asn Asn Ile Asn Asn Pro
        35                  40                  45

Trp Val Tyr Leu Pro Gly Val Tyr Pro Arg Asn Met Arg Leu Asp Ser
    50                  55                  60

Lys Thr Ala Thr Phe Tyr Ser Ser Arg Pro Ser Lys Ala Leu Asn Gly
65                  70                  75                  80

Arg Arg Ala Ile Val Pro Cys Ala Asn Ile Leu Gly Gly Ser Ser
                85                  90                  95

Ile Asn Phe Leu Met Tyr Thr Arg Ala Ser Ala Ser Asp Tyr Asp Asp
                100                 105                 110

Trp Glu Ser Glu Gly Trp Ser Thr Asp Glu Leu Leu Pro Leu Ile Lys
            115                 120                 125

Lys Ile Glu Thr Tyr Gln Arg Pro Cys Asn Asn Arg Asp Leu His Gly
130                 135                 140

Phe Asp Gly Pro Ile Lys Val Ser Phe Gly Asn Tyr Thr Tyr Pro Thr
145                 150                 155                 160

Cys Gln Asp Phe Leu Arg Ala Ala Glu Ser Gln Gly Ile Pro Val Val
                165                 170                 175

Asp Asp Leu Glu Asp Phe Lys Thr Ser His Gly Ala Glu His Trp Leu
            180                 185                 190

Lys Trp Ile Asn Arg Asp Leu Gly Arg Arg Ser Asp Ser Ala His Ala
        195                 200                 205

Tyr Val His Pro Thr Met Arg Asn Lys Gln Ser Leu Phe Leu Ile Thr
    210                 215                 220

Ser Thr Lys Cys Asp Lys Val Ile Ile Glu Asp Gly Lys Ala Val Ala
225                 230                 235                 240

Val Arg Thr Val Pro Met Lys Pro Leu Asn Pro Lys Lys Pro Val Ser
                245                 250                 255

Arg Thr Phe Arg Ala Arg Lys Gln Ile Val Ile Ser Cys Gly Thr Ile
            260                 265                 270

Ser Ser Pro Leu Val Leu Gln Arg Ser Gly Ile Gly Ala Ala His His
        275                 280                 285

Leu Arg Ser Val Gly Val Lys Pro Ile Val Asp Leu Pro Gly Val Gly
    290                 295                 300

Glu Asn Phe Gln Asp His Tyr Cys Phe Phe Thr Pro Tyr Tyr Val Lys
305                 310                 315                 320

Pro Asp Val Pro Thr Phe Asp Phe Val Arg Gly Asp Pro Val Ala
                325                 330                 335

Gln Lys Ala Ala Phe Asp Gln Trp Tyr Ser Asn Lys Asp Gly Pro Leu
            340                 345                 350

Thr Thr Asn Gly Ile Glu Ala Gly Val Lys Ile Arg Pro Thr Glu Glu
        355                 360                 365

Glu Leu Ala Thr Ala Asp Glu Asp Phe Arg Arg Gly Tyr Ala Glu Tyr
    370                 375                 380
```

-continued

Phe Glu Asn Lys Pro Asp Lys Pro Leu Met His Tyr Ser Val Ile Ser
385                 390                 395                 400

Gly Phe Phe Gly Asp His Thr Lys Ile Pro Asn Gly Lys Phe Met Thr
            405                 410                 415

Met Phe His Phe Leu Glu Tyr Pro Phe Ser Arg Gly Phe Val Arg Ile
        420                 425                 430

Thr Ser Ala Asn Pro Tyr Asp Ala Pro Asp Phe Asp Pro Gly Phe Leu
    435                 440                 445

Asn Asp Glu Arg Asp Leu Trp Pro Met Val Trp Ala Tyr Lys Lys Ser
450                 455                 460

Arg Glu Thr Ala Arg Met Glu Ser Phe Ala Gly Glu Val Thr Ser
465                 470                 475                 480

His His Pro Leu Phe Lys Val Asp Ser Pro Ala Arg Ala Arg Asp Leu
                485                 490                 495

Asp Leu Glu Thr Cys Ser Ala Tyr Ala Gly Pro Lys His Leu Thr Ala
            500                 505                 510

Asn Leu Tyr His Gly Ser Trp Thr Val Pro Ile Asp Lys Pro Thr Pro
        515                 520                 525

Lys Asn Asp Phe His Val Thr Ser Asn Gln Val Gln Leu His Ser Asp
    530                 535                 540

Ile Glu Tyr Thr Glu Glu Asp Glu Ala Ile Val Asn Tyr Ile Lys
545                 550                 555                 560

Glu His Thr Glu Thr Thr Trp His Cys Leu Gly Thr Cys Ser Met Ala
                565                 570                 575

Pro Arg Glu Gly Ser Lys Ile Ala Pro Lys Gly Val Leu Asp Ala
            580                 585                 590

Arg Leu Asn Val Tyr Gly Val Gln Asn Leu Lys Val Ala Asp Leu Ser
        595                 600                 605

Val Cys Pro Asp Asn Val Gly Cys Asn Thr Tyr Ser Thr Ala Leu Thr
610                 615                 620

Ile Gly Glu Lys Ala Ala Thr Leu Val Ala Glu Asp Leu Gly Tyr Ser
625                 630                 635                 640

Gly Ser Asp Leu Asp Met Thr Ile Pro Asn Phe Arg Leu Gly Thr Tyr
            645                 650                 655

Glu Glu Thr Gly Leu Ala Arg Phe
            660

<210> SEQ ID NO 15
<211> LENGTH: 710
<212> TYPE: PRT
<213> ORGANISM: Pichia angusta

<400> SEQUENCE: 15

Met Ser Met Arg Ile Pro Lys Ala Ala Ser Val Asn Asp Glu Gln His
1               5                   10                  15

Gln Arg Ile Ile Lys Tyr Gly Arg Ala Leu Val Leu Asp Ile Val Glu
            20                  25                  30

Gln Tyr Gly Gly Gly His Pro Gly Ser Ala Met Gly Ala Met Ala Ile
        35                  40                  45

Gly Ile Ala Leu Trp Lys Tyr Thr Leu Lys Tyr Ala Pro Asn Asp Pro
    50                  55                  60

Asn Tyr Phe Asn Arg Asp Arg Phe Val Leu Ser Asn Gly His Val Cys
65                  70                  75                  80

Leu Phe Gln Tyr Ile Phe Gln His Leu Tyr Gly Leu Lys Ser Met Thr

```
                85                  90                  95
Met Ala Gln Leu Lys Ser Tyr His Ser Asn Asp Phe His Ser Leu Cys
            100                 105                 110

Pro Gly His Pro Glu Ile Glu His Asp Ala Val Glu Val Thr Thr Gly
            115                 120                 125

Pro Leu Gly Gln Gly Ile Ser Asn Ser Val Gly Leu Ala Ile Ala Thr
130                 135                 140

Lys Asn Leu Ala Ala Thr Tyr Asn Lys Pro Gly Phe Asp Ile Ile Thr
145                 150                 155                 160

Asn Lys Val Tyr Cys Met Val Gly Asp Ala Cys Leu Gln Glu Gly Pro
                165                 170                 175

Ala Leu Glu Ser Ile Ser Leu Ala Gly His Met Gly Leu Asp Asn Leu
            180                 185                 190

Ile Val Leu Tyr Asp Asn Asn Gln Val Cys Cys Asp Gly Ser Val Asp
            195                 200                 205

Ile Ala Asn Thr Glu Asp Ile Ser Ala Lys Phe Lys Ala Cys Asn Trp
            210                 215                 220

Asn Val Ile Glu Val Glu Asn Ala Ser Glu Asp Val Ala Thr Ile Val
225                 230                 235                 240

Lys Ala Leu Glu Tyr Ala Gln Ala Glu Lys His Arg Pro Thr Leu Ile
                245                 250                 255

Asn Cys Arg Thr Val Ile Gly Ser Gly Ala Ala Phe Glu Asn His Cys
            260                 265                 270

Ala Ala His Gly Asn Ala Leu Gly Glu Asp Gly Val Arg Glu Leu Lys
            275                 280                 285

Ile Lys Tyr Gly Met Asn Pro Ala Gln Lys Phe Tyr Ile Pro Gln Asp
290                 295                 300

Val Tyr Asp Phe Phe Lys Glu Lys Pro Ala Gly Asp Lys Leu Val
305                 310                 315                 320

Ala Glu Trp Lys Ser Leu Val Ala Lys Tyr Val Lys Ala Tyr Pro Glu
                325                 330                 335

Glu Gly Gln Glu Phe Leu Ala Arg Met Arg Gly Glu Leu Pro Lys Asn
            340                 345                 350

Trp Lys Ser Phe Leu Pro Gln Gln Glu Phe Thr Gly Asp Ala Pro Thr
            355                 360                 365

Arg Ala Ala Arg Glu Leu Val Arg Ala Leu Gly Gln Asn Cys Lys
370                 375                 380

Ser Val Ile Ala Gly Cys Ala Asp Leu Ser Val Ser Val Asn Leu Gln
385                 390                 395                 400

Trp Pro Gly Val Lys Tyr Phe Met Asp Pro Ser Leu Ser Thr Gln Cys
                405                 410                 415

Gly Leu Ser Gly Asp Tyr Ser Gly Arg Tyr Ile Glu Tyr Gly Ile Arg
            420                 425                 430

Glu His Ala Met Cys Ala Ile Ala Asn Gly Leu Ala Tyr Asn Lys
            435                 440                 445

Gly Thr Phe Leu Pro Ile Thr Ser Thr Phe Phe Met Phe Tyr Leu Tyr
            450                 455                 460

Ala Ala Pro Ala Ile Arg Met Ala Gly Leu Gln Glu Leu Lys Ala Ile
465                 470                 475                 480

His Ile Gly Thr His Asp Ser Ile Asn Glu Gly Glu Asn Gly Pro Thr
                485                 490                 495

His Gln Pro Val Glu Ser Pro Ala Leu Phe Arg Ala Met Pro Asn Ile
            500                 505                 510
```

-continued

```
Tyr Tyr Met Arg Pro Val Asp Ser Ala Glu Val Phe Gly Leu Phe Gln
            515                 520                 525

Lys Ala Val Glu Leu Pro Phe Ser Ser Ile Leu Ser Leu Ser Arg Asn
530                 535                 540

Glu Val Leu Gln Tyr Pro Gly Lys Ser Ser Ala Glu Lys Ala Gln Arg
545                 550                 555                 560

Gly Gly Tyr Ile Leu Glu Asp Ala Glu Asn Ala Glu Val Gln Ile Ile
                565                 570                 575

Gly Val Gly Ala Glu Met Glu Phe Ala Tyr Lys Ala Ala Lys Ile Leu
            580                 585                 590

Gly Arg Lys Phe Arg Thr Arg Val Leu Ser Ile Pro Cys Thr Arg Leu
            595                 600                 605

Phe Asp Glu Gln Ser Ile Gly Tyr Arg Arg Ser Val Leu Arg Lys Asp
610                 615                 620

Gly Arg Gln Val Pro Thr Val Val Asp Gly His Val Ala Phe Gly
625                 630                 635                 640

Trp Glu Arg Tyr Ala Thr Ala Ser Tyr Cys Met Asn Thr Tyr Gly Lys
                645                 650                 655

Ser Leu Pro Pro Glu Val Ile Tyr Glu Tyr Phe Gly Tyr Asn Pro Ala
            660                 665                 670

Thr Ile Ala Lys Lys Val Glu Ala Tyr Val Arg Ala Cys Gln Arg Asp
            675                 680                 685

Pro Leu Leu Leu His Asp Phe Leu Asp Leu Lys Glu Lys Pro Asn His
            690                 695                 700

Asp Lys Val Asn Lys Leu
705                 710

<210> SEQ ID NO 16
<211> LENGTH: 709
<212> TYPE: PRT
<213> ORGANISM: Pichia methanolica

<400> SEQUENCE: 16

Met Arg Ile Ala Arg Ala Val Ser Thr Ser Asp Tyr Glu His Asp Gln
1               5                  10                  15

Ile Ile Lys Tyr Gly Arg Ala Leu Val Leu Asp Ile Val Gln Gln Tyr
                20                  25                  30

Asp Gly Gly His Pro Gly Ser Ala Met Gly Met Ala Leu Gly Ile
            35                  40                  45

Ala Leu Trp Lys Tyr Thr Met Lys Tyr Ala Pro Asn Asp Pro Thr Tyr
50                  55                  60

Phe Asn Arg Asp Arg Phe Val Leu Ser Asn Gly His Val Cys Leu Leu
65                  70                  75                  80

Gln Tyr Val Phe Gln His Phe Thr Gly Leu Lys Ser Met Thr Met Asp
                85                  90                  95

Gln Leu Lys Ser Tyr His Ser Asn Asp Phe His Ser His Cys Pro Gly
            100                 105                 110

His Pro Glu Ile Glu His Asp Ala Val Glu Val Thr Thr Gly Pro Leu
            115                 120                 125

Gly Gln Gly Ile Ala Asn Ser Val Gly Leu Ala Ile Ala Thr Lys Asn
        130                 135                 140

Leu Ala Ala Thr Tyr Asn Lys Pro Gly Tyr Asn Leu Val Asp Asn Lys
145                 150                 155                 160

Thr Tyr Cys Ile Val Gly Asp Ala Cys Leu Gln Glu Gly Pro Ala Leu
```

```
                    165                 170                 175
Glu Ala Ile Ser Ile Ala Gly His Tyr Gly Leu Asn Asn Leu Ile Val
                180                 185                 190
Leu Tyr Asp Asn Asn Gln Val Cys Ala Asp Gly Ser Val Asp Ile Ala
                195                 200                 205
Asn Thr Glu Asp Ile Ser Ala Lys Phe Lys Ala Cys Asn Trp Asn Val
                210                 215                 220
Ile Glu Val Ala Asn Ala Ser Glu Asp Val Ala Thr Ile Val Lys Ala
225                 230                 235                 240
Leu Glu Tyr Ala Gln Asn Glu Val Lys Ala Pro Thr Leu Ile Asn Cys
                245                 250                 255
Arg Thr Val Ile Gly Ala Asp Ala Ala Phe Glu Asn His His Ala Asp
                260                 265                 270
His Gly Asn Ser Leu Gly Ala Asp Gly Val Arg Glu Val Lys Lys Lys
                275                 280                 285
Leu Gly Met Asn Pro Ala Gln Lys Phe His Val Pro Lys Glu Ile Tyr
                290                 295                 300
Gln Phe Phe Ser Asn Lys Ile Thr Glu Gly Asp Gln Leu Val Ala Asp
305                 310                 315                 320
Trp Lys Lys Leu Val Asp Asn Tyr Val Lys Glu Tyr Pro Glu Leu Gly
                325                 330                 335
Lys Glu Phe Leu Ala Arg Val Ser Gly Glu Leu Pro Ala Asp Trp Lys
                340                 345                 350
Ser Ser Leu Pro Val Gln Asp Tyr Ala Gly Asp Thr Pro Thr Arg Ala
                355                 360                 365
Ala Ala Arg Gly Leu Val Gln Ala Ala Gly Lys Ala Ile Pro Asn Ile
                370                 375                 380
Met Ala Gly Cys Ala Asp Leu Ser Val Ser Val Asn Leu Gln Trp Pro
385                 390                 395                 400
Gly Val Thr Tyr Phe Gln Asp Pro Ser Leu Arg Thr Asn Cys Gly Leu
                405                 410                 415
Thr Gly Asp Tyr Ser Gly Arg Tyr Leu Glu Tyr Gly Ile Arg Glu His
                420                 425                 430
Ala Met Cys Ala Ile Ala Asn Gly Met Ala Ala Phe Asn Lys Gly Thr
                435                 440                 445
Phe Ile Pro Ile Thr Ser Thr Phe Phe Met Phe Tyr Leu Tyr Ala Ala
                450                 455                 460
Pro Ala Ile Arg Met Ala Gly Leu Gln Glu Leu Lys Thr Ile His Ile
465                 470                 475                 480
Gly Thr His Asp Ser Ile Asn Glu Gly Glu Asn Gly Pro Thr His Gln
                485                 490                 495
Pro Ile Glu Ser Pro Ser Leu Phe Arg Ala Met Leu Asn Val Tyr Tyr
                500                 505                 510
Met Arg Pro Val Asp Ser Ala Glu Val Leu Gly Leu Phe Glu Lys Ala
                515                 520                 525
Ile Glu Cys Pro Tyr Thr Ser Met Leu Ser Leu Ser Arg Asn Glu Val
                530                 535                 540
Leu Gln Tyr Pro Gly Leu Ser Ser Pro Glu Lys Ala Lys Arg Gly Gly
545                 550                 555                 560
Tyr Ile Leu Glu Asp Val Glu Asn Ala Asp Val Gln Leu Ile Gly Ala
                565                 570                 575
Gly Ala Glu Met Glu Phe Ala Tyr Lys Ala Ala Lys Ile Leu Gly Arg
                580                 585                 590
```

```
Lys Gly Leu Lys Val Arg Val Leu Ser Ile Pro Cys Thr Arg Leu Phe
            595                 600                 605

Asp Glu His Ser Leu Gly Ser Arg Arg Ser Val Leu Arg Lys Asp Gly
            610                 615                 620

Ser Gln Val Pro Pro Val Ile Val Asp Gly His Val Ala Phe Gly Trp
625                 630                 635                 640

Glu Arg Tyr Ser Thr Ala Ser Tyr Cys Met Asn Thr Tyr Gly Lys Ser
            645                 650                 655

Leu Pro Pro Asp Val Ile Tyr Glu Tyr Phe Gly Tyr Asn Pro Asn Thr
            660                 665                 670

Ile Ala Lys Lys Val Glu Ala Tyr Val Lys Ala Cys Arg Ala Asp Pro
            675                 680                 685

Leu Leu Leu His Asp Tyr Val Asp Leu Lys Glu Lys Pro Lys His Asp
            690                 695                 700

Lys Val Asn Lys Leu
705

<210> SEQ ID NO 17
<211> LENGTH: 706
<212> TYPE: PRT
<213> ORGANISM: Candida boidinii

<400> SEQUENCE: 17

Met Ala Leu Ala Lys Ala Ala Ser Ile Asn Asp Asp Ile His Asp Leu
1               5                   10                  15

Thr Met Arg Ala Phe Arg Cys Tyr Val Leu Asp Leu Val Glu Gln Tyr
            20                  25                  30

Glu Gly Gly His Pro Gly Ser Ala Met Gly Met Val Ala Met Gly Ile
            35                  40                  45

Ala Leu Trp Lys Tyr Thr Met Lys Tyr Ser Thr Asn Asp Pro Thr Trp
        50                  55                  60

Phe Asn Arg Asp Arg Phe Val Leu Ser Asn Gly His Val Cys Leu Phe
65                  70                  75                  80

Gln Tyr Leu Phe Gln His Leu Ser Gly Leu Lys Ser Met Thr Glu Lys
            85                  90                  95

Gln Leu Lys Ser Tyr His Ser Ser Asp Tyr His Ser Lys Cys Pro Gly
            100                 105                 110

His Pro Glu Ile Glu Asn Glu Ala Val Glu Val Thr Thr Gly Pro Leu
        115                 120                 125

Gly Gln Gly Ile Ser Asn Ser Val Gly Leu Ala Ile Ala Ser Lys Asn
130                 135                 140

Leu Gly Ala Leu Tyr Asn Lys Pro Gly Tyr Glu Val Val Asn Asn Thr
145                 150                 155                 160

Thr Tyr Cys Ile Val Gly Asp Ala Cys Leu Gln Glu Gly Pro Ala Leu
            165                 170                 175

Glu Ser Ile Ser Phe Ala Gly His Leu Gly Leu Asp Asn Leu Val Val
            180                 185                 190

Ile Tyr Asp Asn Asn Gln Val Cys Cys Asp Gly Ser Val Asp Ile Ala
        195                 200                 205

Asn Thr Glu Asp Ile Ser Ala Lys Phe Arg Ala Cys Asn Trp Asn Val
        210                 215                 220

Ile Glu Val Glu Asp Gly Ala Arg Asp Val Ala Thr Ile Val Lys Ala
225                 230                 235                 240

Leu Glu Leu Ala Gly Ala Glu Lys Asn Arg Pro Thr Leu Ile Asn Val
```

```
                    245                 250                 255
Arg Thr Ile Ile Gly Thr Asp Ser Ala Phe Gln Asn His Cys Ala Ala
                260                 265                 270

His Gly Ser Ala Leu Gly Glu Glu Gly Ile Arg Glu Leu Lys Ile Lys
            275                 280                 285

Tyr Gly Phe Asn Pro Ser Gln Lys Phe His Phe Pro Gln Glu Val Tyr
        290                 295                 300

Asp Phe Phe Ser Asp Ile Pro Ala Lys Gly Asp Glu Tyr Val Ser Asn
305                 310                 315                 320

Trp Asn Lys Leu Val Ser Ser Tyr Val Lys Glu Phe Pro Glu Leu Gly
                325                 330                 335

Ala Glu Phe Gln Ser Arg Val Lys Gly Glu Leu Pro Lys Asn Trp Lys
            340                 345                 350

Ser Leu Leu Pro Asn Asn Leu Pro Asn Glu Asp Thr Ala Thr Arg Thr
        355                 360                 365

Ser Ala Arg Ala Met Val Arg Ala Leu Ala Lys Asp Val Pro Asn Val
    370                 375                 380

Ile Ala Gly Ser Ala Asp Leu Ser Val Ser Val Asn Leu Pro Trp Pro
385                 390                 395                 400

Gly Ser Lys Tyr Phe Glu Asn Pro Gln Leu Ala Thr Gln Cys Gly Leu
                405                 410                 415

Ala Gly Asp Tyr Ser Gly Arg Tyr Val Glu Phe Gly Ile Arg Glu His
            420                 425                 430

Cys Met Cys Ala Ile Ala Asn Gly Leu Ala Ala Phe Asn Lys Gly Thr
        435                 440                 445

Phe Leu Pro Ile Thr Ser Ser Phe Tyr Met Phe Tyr Leu Tyr Ala Ala
    450                 455                 460

Pro Ala Leu Arg Met Ala Ala Leu Gln Glu Leu Lys Ala Ile His Ile
465                 470                 475                 480

Ala Thr His Asp Ser Ile Gly Ala Gly Glu Asp Gly Pro Thr His Gln
                485                 490                 495

Pro Ile Ala Gln Ser Ala Leu Trp Arg Ala Met Pro Asn Phe Tyr Tyr
            500                 505                 510

Met Arg Pro Gly Asp Ala Ser Glu Val Arg Gly Leu Phe Glu Lys Ala
        515                 520                 525

Val Glu Leu Pro Leu Ser Thr Leu Phe Ser Leu Ser Arg His Glu Val
    530                 535                 540

Pro Gln Tyr Pro Gly Lys Ser Ser Ile Glu Leu Ala Lys Arg Gly Gly
545                 550                 555                 560

Tyr Val Phe Glu Asp Ala Lys Asp Ala Asp Ile Gln Leu Ile Gly Ala
                565                 570                 575

Gly Ser Glu Leu Glu Gln Ala Val Lys Thr Ala Arg Ile Leu Arg Ser
            580                 585                 590

Arg Gly Leu Lys Val Arg Ile Leu Ser Phe Pro Cys Gln Arg Leu Phe
        595                 600                 605

Asp Glu Gln Ser Val Gly Tyr Arg Arg Ser Val Leu Gln Arg Gly Lys
    610                 615                 620

Val Pro Thr Val Ile Glu Ala Tyr Val Ala Tyr Gly Trp Glu Arg
625                 630                 635                 640

Tyr Ala Thr Ala Gly Tyr Thr Met Asn Thr Phe Gly Lys Ser Leu Pro
                645                 650                 655

Val Glu Asp Val Tyr Glu Tyr Phe Gly Phe Asn Pro Ser Glu Ile Ser
            660                 665                 670
```

```
Lys Lys Ile Glu Gly Tyr Val Arg Ala Val Lys Ala Asn Pro Asp Leu
            675                 680                 685

Leu Tyr Glu Phe Ile Asp Leu Thr Glu Lys Pro Lys His Asp Gln Asn
            690                 695                 700

His Leu
705

<210> SEQ ID NO 18
<211> LENGTH: 705
<212> TYPE: PRT
<213> ORGANISM: Kuraishia capsulata

<400> SEQUENCE: 18

Met Arg Ile Pro Lys Ala Gln Asn Phe Asn Glu Asp Ile His Asp Leu
1               5                   10                  15

Val Ile Arg Ser Phe Arg Cys Tyr Val Leu Asp Leu Val Glu Gln Tyr
            20                  25                  30

Gly Gly Gly His Pro Gly Ser Ala Met Gly Met Val Ala Ile Gly Ile
        35                  40                  45

Ala Leu Trp Lys Tyr Thr Met Lys Tyr Ser Pro Asn Asp Pro Thr Tyr
50                  55                  60

Phe Asn Arg Asp Arg Phe Val Leu Ser Asn Gly His Thr Cys Leu Phe
65                  70                  75                  80

Gln Tyr Leu Phe Gln His Leu Thr Gly Leu Lys Ser Met Thr Val Lys
            85                  90                  95

Gln Leu Lys Ser Tyr His Ser Ser Asp Tyr His Ser Leu Thr Pro Gly
            100                 105                 110

His Pro Glu Ile Glu Asn Asp Ala Val Glu Val Thr Thr Gly Pro Leu
        115                 120                 125

Gly Gln Gly Ile Ser Asn Ser Val Gly Leu Ala Ile Ala Thr Lys Asn
130                 135                 140

Leu Ala Ala Leu Tyr Asn Arg Pro Gly Phe Asp Val Val Asn Asn Lys
145                 150                 155                 160

Thr Tyr Ala Ile Val Gly Asp Ala Cys Leu Gln Glu Gly Pro Ala Leu
            165                 170                 175

Glu Ser Ile Ser Leu Ala Gly His Leu Gly Leu Ser Asn Leu Ile Val
            180                 185                 190

Ile Tyr Asp Asn Asn Gln Val Cys Cys Asp Gly Ser Val Asp Ile Ala
        195                 200                 205

Asn Thr Glu Asp Ile Ser Ala Lys Phe Lys Ala Cys Asn Trp Asn Val
210                 215                 220

Ile Asp Val Ser Asp Ala Ala Glu Asp Val Ala Thr Leu Val Arg Ala
225                 230                 235                 240

Leu Glu Tyr Ala Gly Arg Glu Thr Ser Arg Pro Thr Leu Ile Asn Ala
            245                 250                 255

Arg Thr Val Ile Gly Ala Gly Ala Glu Phe Glu Asn His Cys Asn Ala
            260                 265                 270

His Gly Asn Ala Leu Gly Glu Ala Gly Val Arg Ala Ala Lys Val Arg
        275                 280                 285

Tyr Gly Phe Asn Pro Asn Gln Lys Phe Tyr Phe Pro Glu Glu Val Tyr
290                 295                 300

Asp Phe Phe Ser Glu Ile Pro Ala Arg Gly Asp Lys Leu Val Ser Glu
305                 310                 315                 320

Trp Lys Gln Leu Val Ser Ala Tyr Ser Lys Ala His Pro Glu Val Ala
```

```
                    325                 330                 335
Ala Glu Phe Leu Gly Arg Thr Arg Gly Glu Leu Pro Lys Asn Trp Lys
                340                 345                 350

Ser Leu Leu Pro Ser Glu Ala Pro Thr Glu Ala Thr Ala Thr Arg Thr
            355                 360                 365

Thr Ala Arg Glu Cys Val Arg Ala Phe Gly Lys Gly Val Ser Ser Val
        370                 375                 380

Ile Ala Gly Ser Ala Asp Leu Ser Val Ser Val Asp Leu Pro Trp Glu
385                 390                 395                 400

Gly Val Glu Tyr Phe Leu Ser Pro Glu Leu Ala Thr Glu Cys Gly Leu
                405                 410                 415

Ser Gly Ser Phe Arg Gly Arg Tyr Ile Glu Phe Gly Ile Arg Glu His
            420                 425                 430

Ser Met Cys Ala Ile Ala Ser Gly Leu Ala Ala Phe Asn Pro Gly Thr
        435                 440                 445

Phe Val Pro Ile Thr Ser Ser Phe Tyr Met Phe Tyr Leu Tyr Ala Ala
    450                 455                 460

Pro Ala Leu Arg Met Ala Ala Leu Gln Glu Leu Lys Ala Ile His Ile
465                 470                 475                 480

Ala Thr His Asp Ser Ile Gly Ala Gly Glu Asp Gly Pro Thr His Gln
                485                 490                 495

Pro Ile Ala Gln Ser Ala Leu Trp Arg Ala Met Pro Asn Phe Tyr Tyr
            500                 505                 510

Met Arg Pro Ala Asp Ala Thr Glu Val Arg Ala Cys Phe Glu Lys Ala
        515                 520                 525

Val Glu Leu Pro Val Ser Ser Leu Ser Leu Ser Arg His Glu Val
    530                 535                 540

Pro Gln Tyr Pro Gly Thr Ser Ser Leu Ala Lys Ala Lys Arg Gly Gly
545                 550                 555                 560

Tyr Val Phe Arg Asp Val Glu Arg Pro Asp Phe Gln Phe Ile Gly Val
                565                 570                 575

Gly Ser Glu Met Glu Trp Val Val Lys Ala Ala Asp Leu Leu Thr Lys
            580                 585                 590

Thr Lys Gly Tyr Arg Ile Arg Ile Leu Ser Phe Pro Cys Gln Arg Leu
        595                 600                 605

Phe Asp Glu Gln Ser Val Ser Tyr Arg Arg Ser Val Leu Arg Arg Gly
    610                 615                 620

Glu Leu Pro Thr Ile Val Val Glu Ala Tyr Val Ala Tyr Gly Trp Glu
625                 630                 635                 640

Arg Tyr Ala Thr Ala Gly Tyr Asn Met Asn Thr Phe Gly Lys Ser Leu
                645                 650                 655

Pro Val Asp Asp Val Tyr Gln Tyr Phe Gly Phe Thr Pro Glu Ser Ile
            660                 665                 670

Ala Asp Arg Val Asp Ser Tyr Val Lys Arg Val Lys Ala Glu Pro Gln
        675                 680                 685

Leu Leu Trp Glu Phe Gln Asp Leu Lys Thr Arg Pro Lys His Asp Lys
    690                 695                 700

Leu
705

<210> SEQ ID NO 19
<211> LENGTH: 707
<212> TYPE: PRT
<213> ORGANISM: Komagataella pastoris
```

<400> SEQUENCE: 19

```
Met Ala Arg Ile Pro Lys Ala Val Ser Thr Gln Asp Asp Ile His Glu
1               5                   10                  15

Leu Val Ile Lys Thr Phe Arg Cys Tyr Val Leu Asp Leu Val Glu Gln
                20                  25                  30

Tyr Gly Gly Gly His Pro Gly Ser Ala Met Gly Met Val Ala Ile Gly
            35                  40                  45

Ile Ala Leu Trp Lys Tyr Gln Met Lys Tyr Ala Pro Asn Asp Pro Asp
        50                  55                  60

Tyr Phe Asn Arg Asp Arg Phe Val Leu Ser Asn Gly His Val Cys Leu
65                  70                  75                  80

Phe Gln Tyr Leu Phe Gln His Leu Thr Gly Leu Lys Glu Met Thr Val
                85                  90                  95

Lys Gln Leu Gln Ser Tyr His Ser Ser Asp Tyr His Ser Leu Thr Pro
                100                 105                 110

Gly His Pro Glu Ile Glu Asn Pro Ala Val Glu Val Thr Thr Gly Pro
            115                 120                 125

Leu Gly Gln Gly Ile Ser Asn Ala Val Gly Met Ala Ile Gly Ser Lys
130                 135                 140

Asn Leu Ala Ala Thr Tyr Asn Arg Pro Gly Phe Pro Val Val Asp Asn
145                 150                 155                 160

Thr Ile Tyr Ala Ile Val Gly Asp Ala Cys Leu Gln Glu Gly Pro Ala
                165                 170                 175

Leu Glu Ser Ile Ser Leu Ala Gly His Leu Ala Leu Asp Asn Leu Ile
                180                 185                 190

Val Ile Tyr Asp Asn Asn Gln Val Cys Cys Asp Gly Ser Val Asp Val
            195                 200                 205

Asn Asn Thr Glu Asp Ile Ser Ala Lys Phe Arg Ala Gln Asn Trp Asn
210                 215                 220

Val Ile Asp Ile Val Asp Gly Ser Arg Asp Val Ala Thr Ile Val Lys
225                 230                 235                 240

Ala Ile Asp Trp Ala Lys Ala Glu Thr Glu Arg Pro Thr Leu Ile Asn
                245                 250                 255

Val Arg Thr Glu Ile Gly Gln Asp Ser Ala Phe Gly Asn His His Ala
            260                 265                 270

Ala His Gly Ser Ala Leu Gly Glu Glu Gly Ile Arg Glu Leu Lys Thr
        275                 280                 285

Lys Tyr Gly Phe Asn Pro Ala Gln Lys Phe Trp Phe Pro Lys Glu Val
290                 295                 300

Tyr Asp Phe Phe Ala Glu Lys Pro Ala Lys Gly Asp Glu Leu Val Lys
305                 310                 315                 320

Asn Trp Lys Lys Leu Val Asp Ser Tyr Val Lys Glu Tyr Pro Arg Glu
                325                 330                 335

Gly Gln Glu Phe Leu Ser Arg Val Arg Gly Leu Pro Lys Asn Trp
            340                 345                 350

Arg Thr Tyr Ile Pro Gln Asp Lys Pro Thr Glu Pro Thr Ala Thr Arg
        355                 360                 365

Thr Ser Ala Arg Glu Ile Val Arg Ala Leu Gly Lys Asn Leu Pro Gln
    370                 375                 380

Val Ile Ala Gly Ser Gly Asp Leu Ser Val Ser Ile Leu Leu Asn Trp
385                 390                 395                 400

Asp Gly Val Lys Tyr Phe Asn Pro Lys Leu Gln Thr Phe Cys Gly
```

405                 410                 415
Leu Gly Gly Asp Tyr Ser Gly Arg Tyr Ile Glu Phe Gly Ile Arg Glu
            420                 425                 430

His Ser Met Cys Ala Ile Ala Asn Gly Leu Ala Ala Tyr Asn Lys Gly
        435                 440                 445

Thr Phe Leu Pro Ile Thr Ser Thr Phe Tyr Met Phe Tyr Leu Tyr Ala
    450                 455                 460

Ala Pro Ala Leu Arg Met Ala Ala Leu Gln Glu Leu Lys Ala Ile His
465                 470                 475                 480

Ile Ala Thr His Asp Ser Ile Gly Ala Gly Glu Asp Gly Pro Thr His
                485                 490                 495

Gln Pro Ile Ala Leu Ser Ser Leu Phe Arg Ala Met Pro Asn Phe Tyr
            500                 505                 510

Tyr Met Arg Pro Ala Asp Ala Thr Glu Val Ala Ala Leu Phe Glu Val
        515                 520                 525

Ala Val Glu Leu Glu His Ser Thr Leu Leu Ser Leu Ser Arg His Glu
    530                 535                 540

Val Asp Gln Tyr Pro Gly Lys Thr Ser Ala Gln Gly Ala Lys Arg Gly
545                 550                 555                 560

Gly Tyr Val Val Glu Asp Cys Glu Gly Lys Pro Asp Val Gln Leu Ile
                565                 570                 575

Gly Thr Gly Ser Glu Leu Glu Phe Ala Ile Lys Thr Ala Arg Leu Leu
            580                 585                 590

Arg Gln Gln Lys Gly Trp Lys Val Arg Val Leu Ser Phe Pro Cys Gln
        595                 600                 605

Arg Leu Phe Asp Glu Gln Ser Ile Thr Tyr Arg Arg Ser Val Leu Arg
    610                 615                 620

Arg Gly Glu Val Pro Thr Val Val Glu Ala Tyr Val Ala Tyr Gly
625                 630                 635                 640

Trp Glu Arg Tyr Ala Thr Ala Gly Tyr Thr Met Asn Thr Phe Gly Lys
                645                 650                 655

Ser Leu Pro Val Glu Asp Val Tyr Lys Tyr Phe Gly Tyr Thr Pro Glu
            660                 665                 670

Lys Ile Gly Glu Arg Val Val Gln Tyr Val Asn Ser Ile Lys Ala Ser
        675                 680                 685

Pro Gln Ile Leu Tyr Glu Phe His Asp Leu Lys Gly Lys Pro Lys His
    690                 695                 700

Asp Lys Leu
705

<210> SEQ ID NO 20
<211> LENGTH: 743
<212> TYPE: PRT
<213> ORGANISM: Diaporthe ampelina

<400> SEQUENCE: 20

Met Ala Pro Ser Val Val Asp Val Pro Thr Asp Thr Val Ser His Leu
1               5                   10                  15

Pro Leu Lys Leu Ser Ala Asn Gly Asp Lys Thr Ser Gly Asp His Gly
            20                  25                  30

Ser Ile Ser Lys Leu Glu Leu Lys Asp Val Ala Arg Thr Asp Phe Val
        35                  40                  45

Leu Arg Thr Phe Arg Cys Leu Ile Ala Asp Leu Cys Glu Gln Phe Lys
    50                  55                  60

```
Gly Gly His Pro Gly Ser Ala Met Gly Met Ala Ile Gly Val Ala
 65                  70                  75                  80

Leu Trp Lys Tyr Val Met Arg Tyr Ser Pro Glu Asn Pro Ser Phe Phe
                 85                  90                  95

Asn Arg Asp Arg Phe Val Leu Ser Asn Gly His Cys Cys Leu Trp Gln
            100                 105                 110

Tyr Thr Phe Met His Leu Val Gly Tyr Lys Asn Met Thr Leu Asp Gln
        115                 120                 125

Leu Arg Ser Tyr His Ser Asp Arg Thr Asp Ser Ile Cys Pro Gly His
    130                 135                 140

Pro Glu Ile Glu His Glu Gly Ile Glu Val Thr Thr Gly Pro Leu Gly
145                 150                 155                 160

Gln Gly Ile Ala Asn Ala Val Gly Met Ala Ile Ala Thr Lys Gln Leu
                165                 170                 175

Ala Ala Thr Tyr Asn Lys Pro Gly Phe Pro Val Val Asp Asn Thr Thr
            180                 185                 190

Trp Cys Met Ile Gly Asp Ala Cys Leu Gln Glu Gly Val Gly Leu Glu
        195                 200                 205

Ala Ile Ser Leu Ala Gly His Phe Arg Leu Asn Asn Leu Val Val Val
    210                 215                 220

Tyr Asp Asn Asn Gln Ile Thr Cys Asp Gly Ser Val Asp Leu Thr Asn
225                 230                 235                 240

Thr Glu Asp Val Asn Ala Lys Met Thr Ala Cys Gly Trp Lys Val Ile
                245                 250                 255

Asp Val Leu Asp Gly Asn His Asp Val Glu Gly Ile Val Ser Ala Leu
            260                 265                 270

Val Glu Ala Arg Ala Ser Thr Asp Lys Pro Val Phe Ile Asn Ile Arg
        275                 280                 285

Thr Val Ile Gly Ile Gly Ser Lys Val Ala Gly Asp Ala Lys Ala His
    290                 295                 300

Gly Ala Ala Phe Gly Ala Glu Asp Val Ala Asn Ile Lys Arg Asn Ala
305                 310                 315                 320

Gly Phe Asp Pro Glu Lys His Phe Gln Ile Ser Gln Glu Val Tyr Asp
                325                 330                 335

Tyr Phe Ala Glu Ile Arg Ser Arg Gly Arg Asn Phe Glu Arg Glu Trp
            340                 345                 350

Asp Asp Leu Val Ser Ala Tyr Gly Gly Ser Tyr Pro Asp Leu Ala Lys
        355                 360                 365

Glu Phe Gly His Arg Val Arg Gly Glu Phe Pro Glu Asp Trp Thr Arg
    370                 375                 380

Leu Ile Pro Arg Lys Glu Glu Phe Pro Thr Ala Pro Thr Ala Ser Arg
385                 390                 395                 400

Lys Ser Ala Gly Leu Val Cys Asn Arg Leu Ala Ala Lys Leu Ser Asn
                405                 410                 415

Phe Met Val Gly Thr Ala Asp Leu Ser Pro Ser Val Asn Met Ile Trp
            420                 425                 430

Lys Gly Lys Thr Asp Phe Gln His Pro Asp Leu Arg Pro Thr Cys Gly
        435                 440                 445

Ile Thr Gly Asp Tyr Ser Gly Arg Tyr Ile His Trp Gly Val Arg Glu
    450                 455                 460

His Ala Met Ala Ala Ile Ser Asn Gly Leu Ala Ala Tyr Ser Lys Gly
465                 470                 475                 480

Thr Ile Leu Pro Val Thr Ser Ser Phe Phe Ile Phe Tyr Ile Tyr Ala
```

```
            485                 490                 495
Ala Pro Gly Ile Arg Met Gly Ala Leu Gln Arg Leu Gln Ala Ile His
            500                 505                 510

Ile Gly Thr His Asp Ser Ile Gly Thr Gly Glu Asp Gly Pro Thr His
            515                 520                 525

Gln Pro Val Glu Leu Ala Ala Leu Tyr Arg Ala Met Pro Asn Leu Leu
    530                 535                 540

Tyr Met Arg Pro Cys Asp Ser Glu Glu Val Ala Gly Ala Phe Val Ala
545                 550                 555                 560

Ala Leu Ser Ala Arg Asp Thr Pro Ser Ile Ile Ser Leu Ser Arg Gln
                565                 570                 575

Asn Leu Glu Gln Tyr Pro Ala His Ser Ser Arg Asp Gly Val Leu Arg
            580                 585                 590

Gly Ala Tyr Pro Phe Ile Glu Asp Gly Glu Ala Asp Val Thr Leu Ile
            595                 600                 605

Gly Val Gly Ala Glu Met Ala Phe Ala Val Arg Ala Arg Asp Ala Leu
        610                 615                 620

Arg Asp Arg His Gly Leu Arg Ala Arg Val Val Ser Phe Pro Cys Gln
625                 630                 635                 640

Arg Leu Phe Asp Ala Gln Pro Arg Gly Tyr Arg Ala Glu Thr Leu Arg
                645                 650                 655

Tyr Arg Gly Gly Ala Lys Ala Pro Pro Arg Val Val Glu Ala Tyr
            660                 665                 670

Ala Ala Asn Gly Trp Glu Arg Tyr Ala Asp Ala Gly Tyr Ser Met Ser
            675                 680                 685

Ser Phe Gly His Ser Leu Pro Gly Ala Ala Tyr Lys Tyr Phe Gly
        690                 695                 700

Tyr Asp Pro Glu Leu Ile Ala Ser Arg Val Ala Ala Phe Val Gly Glu
705                 710                 715                 720

Trp Lys Glu Arg Gly Pro Asp Glu Phe Arg Gly Glu Phe Arg Asp Leu
                725                 730                 735

Asn Leu Gly Gly Val Asp His
            740

<210> SEQ ID NO 21
<211> LENGTH: 714
<212> TYPE: PRT
<213> ORGANISM: Aspergillus fumigatus

<400> SEQUENCE: 21

Met Thr Gln Gln Leu Glu Glu Lys Lys Lys Ile Asp Leu Ala Leu Arg
1               5                   10                  15

Thr Ile Arg Cys Leu Ile Leu Asp Leu Cys Gln Gln Tyr Lys Gly Gly
            20                  25                  30

His Pro Gly Gly Ala Met Gly Met Thr Ala Ile Gly Ile Ala Leu Trp
        35                  40                  45

Lys Tyr Cys Met Arg Tyr Val Pro Thr Asn Pro Asn Phe Phe Asn Arg
    50                  55                  60

Asp Arg Phe Val Leu Ser Asn Gly His Thr Cys Leu Phe Gln Tyr Thr
65                  70                  75                  80

Phe Leu His Leu Thr Gly Tyr Lys Ala Met Thr Met Asp Gln Leu Lys
                85                  90                  95

Ser Tyr His Ser Glu Arg Ala Asp Ser Leu Cys Pro Gly His Pro Glu
            100                 105                 110
```

```
Ile Glu Ile Asp Gly Val Glu Val Thr Thr Gly Pro Leu Gly Gln Gly
            115                 120                 125

Val Ala Asn Ala Val Gly Leu Ala Met Ala Thr Lys His Leu Gly Ala
        130                 135                 140

Val Tyr Asn Arg Pro Arg Phe Ser Leu Val Asp Asn Thr Thr Trp Cys
145                 150                 155                 160

Met Val Gly Asp Ala Cys Leu Gln Glu Gly Val Ala Leu Glu Ser Ile
                165                 170                 175

Gln Leu Ala Gly His Trp Arg Leu Asn Asn Leu Val Ile Ile Tyr Asp
                180                 185                 190

Asn Asn Gln Val Thr Cys Asp Gly Ser Val Asp Ile Cys Asn Ser Glu
            195                 200                 205

Asp Ile Asn Ala Lys Met Arg Ala Cys Gly Trp Asp Val Ile Asp Val
    210                 215                 220

Glu Asp Gly Cys Tyr Asp Val Glu Gly Ile Thr Ala Ala Leu Met Arg
225                 230                 235                 240

Ala Arg Ser Ser Lys Glu Lys Pro Thr Phe Ile Asn Val Arg Thr Val
                245                 250                 255

Ile Gly Val Glu Ser Lys Phe Ala Gly Asp Ala Lys Ala His Gly Ala
                260                 265                 270

Ala Phe Gly Glu Asp Glu Val Ala Asn Ile Lys Arg Lys Leu Gly Leu
        275                 280                 285

Asn Pro Asp Glu His Phe Ala Val Pro Asp Glu Val Tyr Gln Phe Phe
        290                 295                 300

Ser Asp Ala Gly Gly Arg Gly Arg Ala Leu Glu Glu Ser Trp Asn Gln
305                 310                 315                 320

Leu Leu Leu Asn Tyr Ser Thr Glu His Pro Glu Met Tyr Glu Glu Phe
                325                 330                 335

Arg Leu Arg Met Leu Gly Arg Met Thr Gln Asp Trp Thr Lys Leu Ile
                340                 345                 350

Pro Ser Lys Glu Glu Phe Pro Ala Ser Pro Thr Ala Ser Arg Lys Ser
            355                 360                 365

Ala Gly Leu Cys Cys Asn Pro Leu Ala Ala Lys Leu Glu Asn Ile Met
    370                 375                 380

Val Gly Thr Ala Asp Leu Thr Pro Ser Val Asn Met Ala Trp Lys Gly
385                 390                 395                 400

Lys Val Asp Phe Gln His Pro Glu Leu Lys Thr Thr Cys Gly Leu Asn
                405                 410                 415

Gly Asn Tyr Thr Gly Arg Tyr Ile His Trp Gly Ile Arg Glu His Ala
                420                 425                 430

Met Ala Ser Ile Ser Asn Gly Leu Ala Ala Phe Asn Lys Gly Thr Ile
                435                 440                 445

Leu Pro Ile Thr Ser Ser Phe Phe Met Phe Tyr Ile Ser Lys Gln Trp
    450                 455                 460

Trp Leu Thr Leu Ser Lys Tyr Ala Ala Pro Gly Ile Arg Met Ala Ala
465                 470                 475                 480

Leu Gln Gly Leu Gln Gln Ile His Ile Ala Thr His Asp Ser Ile Gly
                485                 490                 495

Thr Gly Glu Asp Gly Pro Thr His Gln Pro Ile Ala Leu Ala Ala Leu
            500                 505                 510

Tyr Arg Ala Met Pro Asn Leu Leu Tyr Ile Arg Pro Cys Asp Ser Glu
    515                 520                 525

Glu Thr Ala Gly Ala Phe Ile Ala Ala Met Gln Ala Thr Ser Thr Pro
```

```
                    530                 535                 540
Thr Ile Ile Ser Leu Ser Arg Gln Asn Leu Glu Gln Tyr Pro Lys Phe
545                 550                 555                 560

Ser Ser Arg Glu Gly Val Gln Arg Gly Ala Tyr Val Phe Ile Glu Asp
                    565                 570                 575

Glu Gln Ala Gln Val Thr Leu Ile Gly Val Gly Ala Glu Met Val Phe
                    580                 585                 590

Ala Val Arg Thr Arg Gln Val Leu Arg Asp Arg Phe Asn Ile Arg Ser
                    595                 600                 605

Arg Ile Val Ser Phe Pro Cys Gln Arg Leu Phe Ala Gln Gln Ser Gln
                    610                 615                 620

Glu Tyr Arg Arg Glu Val Leu Lys Tyr Arg Ser Gly Ile Pro Arg Val
625                 630                 635                 640

Val Ile Glu Ala Tyr Ala Val Thr Gly Trp Glu Arg Tyr Ala Asp Ala
                    645                 650                 655

Gly Phe Thr Met Ser Thr Phe Gly His Ser Leu Pro Gly Ala Ala Ala
                    660                 665                 670

Tyr Lys Tyr Phe Gly Phe Asp Glu His Val Ile Ala Pro Glu Val Ala
                    675                 680                 685

Lys Leu Val Asp Glu Val Gln Arg Asp Gly Ile Glu Ser Leu Arg Gly
                    690                 695                 700

Asp Phe Arg Asp Leu Asn Pro Val Arg Arg
705                 710

<210> SEQ ID NO 22
<211> LENGTH: 707
<212> TYPE: PRT
<213> ORGANISM: Pichia methanolica

<400> SEQUENCE: 22

Met Thr Val Ser Glu Ser Ser Ala Ser Leu Ile Gln Ala Lys Gln Asp
1               5                   10                  15

Gln Thr Lys Phe Asp Phe Met Leu Lys Tyr Tyr Arg Asn Leu Ile Val
                    20                  25                  30

Asp Leu Val His Asn Tyr Lys Gly Gly His Gly Gly Gly Pro Asn Gly
                    35                  40                  45

Met Ala Ala Ile Gly Phe Ala Leu Tyr Lys Tyr Val Met Lys Tyr Asn
50                  55                  60

Pro Glu Asn Pro Ser Tyr Phe Asn Arg Asp Arg Phe Ile Leu Ser Asn
65                  70                  75                  80

Gly His Thr Cys Leu Phe Gln Tyr Ala Phe Asn His Leu Val Gly Tyr
                    85                  90                  95

Ser His Met Thr Leu Glu Glu Leu Lys Ser Tyr His Ser Ala Glu Glu
                    100                 105                 110

Glu Ser Leu Cys Pro Gly His Pro Glu Ile Glu His Pro Ala Ile Glu
                    115                 120                 125

Val Thr Thr Gly Pro Leu Gly Gln Gly Ile Ala Asn Ala Val Gly Met
                    130                 135                 140

Ala Val Ala Ser Lys Asn Leu Ala Ala Thr Tyr Asn Arg Glu Gly Phe
145                 150                 155                 160

Pro Val Val Asp Asn Thr Ile Phe Cys Met Val Gly Asp Ala Cys Leu
                    165                 170                 175

Gln Glu Gly Pro Ala Leu Glu Ala Ile Ser Phe Ala Gly Ser Met Arg
                    180                 185                 190
```

-continued

```
Leu Asn Asn Leu Val Val Thr Tyr Asp Asn Asn Gln Ile Ser Cys Asp
        195                 200                 205

Gly Ser Val Asp Ile Thr Asn Thr Glu Asp Ile Asn Ala Lys Phe Ile
        210                 215                 220

Ala Cys Asn Trp Asn Val Ile Asp Val Glu Asn Gly Ser Met Asp Ile
225                 230                 235                 240

Cys Ala Ile Val Gln Ala Leu Glu Asp Ala Lys Leu Ser Asp Lys Pro
                245                 250                 255

Thr Leu Ile Asn Ile His Thr Val Ile Gly Leu Ser Thr Pro Trp Glu
                260                 265                 270

Asn Thr Ala Ala Val His Gly Ala Asp Ile Gly Ala Ala Asn Val Leu
                275                 280                 285

Lys Phe Lys Glu Thr Val Gly Ile Glu Ala Asp Lys Thr Phe Tyr Ile
        290                 295                 300

Pro Asp Glu Met Tyr Lys Tyr Phe Ser Asp Ile Lys Pro Lys Gly Gln
305                 310                 315                 320

Ala Tyr Glu Ala Gln Trp Asn Gln Leu Ile Thr Ser Tyr Glu Ala Ala
                325                 330                 335

Tyr Pro Glu Leu Ala Ala Glu Phe Gln Ile Lys Ile Lys Gly Glu Leu
                340                 345                 350

Pro Ala Asn Trp Lys Asp Tyr Ile Pro Thr Ser Phe Pro Asn Ala Asp
        355                 360                 365

Thr Pro Ser Arg Lys Ser Gly Leu Val Leu Asn Pro Ile Ala Gln
        370                 375                 380

His Leu Asn Gln Phe Leu Val Gly Thr Ala Asp Leu Ser Pro Ser Val
385                 390                 395                 400

Asn Met Ile Trp Pro Gly Lys Val Asp Phe Gln Asp Pro Lys Lys Glu
                405                 410                 415

Thr Ala Cys Gly Leu Asn Gly Asp Tyr Thr Gly Arg Tyr Ile His Tyr
                420                 425                 430

Gly Ile Arg Glu His Ala Met Cys Ala Ile Ala Asn Gly Ile Ala Ala
        435                 440                 445

Tyr Asn Lys Gly Thr Phe Ile Pro Val Thr Ser Thr Phe Phe Met Phe
        450                 455                 460

Tyr Leu Tyr Ala Ala Pro Ala Val Arg Met Gly Ala Leu Met Asn Leu
465                 470                 475                 480

Lys Val Ile His Val Gly Thr His Asp Ser Ile Gly Thr Gly Glu Asp
                485                 490                 495

Gly Pro Thr His Gln Pro Ile Ala Leu Ala Asn Phe Tyr Arg Ala Leu
                500                 505                 510

Pro Asn Leu Tyr Tyr Ile Arg Pro Ala Asp Ser Leu Glu Thr Ala Gly
        515                 520                 525

Ala Tyr Glu Val Ala Ile Glu Ala Glu Gly Tyr Ser Ser Ile Ile Ser
        530                 535                 540

Glu Ser Arg Gln Asn Leu Val Gln Tyr Pro Glu Asn Ser Lys Arg Asp
545                 550                 555                 560

Ala Val Lys Phe Gly Ala Tyr Val Phe Asp Asp Phe Asn Ile Pro Asp
                565                 570                 575

Ala Lys Lys Asp Leu Ile Ile Gly Val Gly Ser Glu Met Cys Phe
                580                 585                 590

Ala Met Gly Ser Ala Ala Ile Leu Arg Ser Gln Gly Tyr Asn Val Arg
        595                 600                 605

Val Val Ser Phe Pro Cys Gln Arg Leu Phe Glu Gln Gln Ser Ala Glu
```

```
            610                 615                 620
Tyr Arg His Ser Val Leu Met Arg Gln Gln Met Ile Pro Thr Val Val
625                 630                 635                 640

Ile Glu Ala Tyr Ala Pro Asn Gly Trp Glu Arg Tyr Ala Thr Ala Gly
                645                 650                 655

Ile Asn Met Lys Thr Phe Gly Lys Ser Leu Pro Gly Met Val Cys Tyr
                660                 665                 670

Asp Phe Phe Gly Tyr Asn Lys Glu Lys Ile Ala Thr Lys Val Asp Ala
                675                 680                 685

Tyr Leu Lys Gln Ile Lys Asp Thr Pro Ser Val Val Tyr Glu Phe Gln
                690                 695                 700

Asp Leu Asn
705

<210> SEQ ID NO 23
<211> LENGTH: 808
<212> TYPE: PRT
<213> ORGANISM: Scedosporium apiospermum

<400> SEQUENCE: 23

Met Val Pro Ile Leu Glu Glu Lys Thr Asn Gly Val Pro Val Leu Ala
1               5                   10                  15

Asp Ile Ser Phe Glu Pro Gln Glu Lys His Asp Leu Val Leu Lys Val
                20                  25                  30

Phe Arg Ala Phe Ile Ala Asp Gln Cys Gln Gln Tyr Asn Gly Gly His
                35                  40                  45

Pro Gly Ser Ala Met Gly Met Ala Ala Ile Gly Ile Ala Leu Tyr Lys
50                  55                  60

Tyr Val Met Lys Tyr Ser Pro Arg Asn Cys Ser Tyr Phe Asn Arg Asp
65                  70                  75                  80

Arg Phe Val Leu Ser Asn Gly His Ala Cys Leu Trp Gln Tyr Leu Phe
                85                  90                  95

Met His Leu Val Gly Val Lys Ser Met Thr Leu Asp Gln Leu Lys Ser
                100                 105                 110

Tyr His Ser Ser Arg Thr Asp Ser Ile Cys Pro Gly His Pro Glu Ile
                115                 120                 125

Glu Asn Glu Gly Val Glu Val Thr Thr Gly Pro Leu Gly Gln Gly Val
130                 135                 140

Ala Asn Ala Val Gly Leu Ala Met Ala Thr Lys Asn Leu Ala Ala Thr
145                 150                 155                 160

Tyr Asn Arg Pro Gly Phe Asp Val Val Asp Asn Met Thr Trp Cys Met
                165                 170                 175

Ile Gly Asp Ala Cys Leu Gln Glu Gly Val Gly Leu Glu Ala Val Ser
                180                 185                 190

Leu Ala Gly His Trp Lys Leu Asn Asn Leu Cys Val Ile Tyr Asp Asn
                195                 200                 205

Asn Ser Ile Thr Cys Asp Gly Thr Ala Asp Val Ala Asn Thr Glu Asp
                210                 215                 220

Ile Asn Ala Lys Met His Ala Thr Gly Trp Asn Val Leu Glu Val Ser
225                 230                 235                 240

Gln Gly Asp Thr Asp Val Val Ala Ile Ala Asn Ala Leu Met Ala Ala
                245                 250                 255

Arg Lys Ser Asp Lys Pro Thr Phe Ile Asn Val Arg Thr Thr Ile Ala
                260                 265                 270
```

```
Tyr Gly Ser Gly Asn Ala Gly Asn Ala Lys Thr His Gly Ala Ala Leu
            275                 280                 285
Gly Val Glu Asp Val Arg Arg Ile Lys Glu Ser Phe Gly Leu Asn Pro
    290                 295                 300
Asp Glu Gln Phe His Ile Pro Lys Gly Val Tyr Asp Phe Phe Gln Asp
305                 310                 315                 320
Ile Leu Asp Arg Gly Glu Ala Leu Lys Lys Trp Gln Asp Thr Val
                325                 330                 335
Gln Arg Tyr Ser Lys Glu His Pro Ile Leu Ala Thr Glu Phe Gly Leu
                340                 345                 350
Arg Val Ala Gly Arg Met Pro Asp Asp Trp Thr Gln Cys Ile Leu Pro
            355                 360                 365
Glu Asp Gln Leu Pro Thr Glu Pro Thr Ala Ser Arg Lys Ser Ala Gly
370                 375                 380
Leu Ile Thr Asn Leu Leu Gly Glu Lys Ile Ser Ser Phe Val Val Gly
385                 390                 395                 400
Thr Ala Asp Leu Thr Pro Ser Cys His Val Ala Phe Asn Lys Lys Val
                405                 410                 415
Asp Phe Gln Ser Pro Asp Leu Arg Thr Ser Cys Gly Leu Asn Gly Asp
                420                 425                 430
Tyr Ser Gly Arg Tyr Val His Tyr Gly Ile Arg Glu His Ala Met Cys
            435                 440                 445
Ser Ile Ser Asn Gly Leu Ala Ala Phe His Lys Gly Thr Phe Leu Pro
        450                 455                 460
Met Thr Ser Ser Phe Phe Met Phe Tyr Leu Tyr Ala Ala Pro Ala Val
465                 470                 475                 480
Arg Met Ala Ala Leu Gln Gly Leu Gln Gln Ile His Ile Ala Thr His
                485                 490                 495
Asp Ser Ile Gly Thr Gly Glu Asp Gly Pro Thr His Gln Pro Val Glu
                500                 505                 510
Leu Ala Ala Leu Tyr Arg Ala Met Pro Asn Thr Leu Tyr Ile Arg Pro
            515                 520                 525
Cys Asp Ser Glu Glu Val Ala Gly Ala Phe Ile Ala Ile Gln Ala
530                 535                 540
Thr Glu Thr Pro Thr Ile Ile Ser Leu Ser Arg Gln Asn Leu Pro Gln
545                 550                 555                 560
Tyr Pro Lys Arg Ser Ser Arg Glu Gly Val Ala Arg Gly Ala Tyr Val
                565                 570                 575
Phe Ser Glu Val Glu Gly Glu Gln Phe Asp Val Thr Leu Ile Gly Val
            580                 585                 590
Gly Ser Glu Met Val Tyr Ala Met Glu Thr Arg Asp Leu Leu Leu Gln
        595                 600                 605
Lys Tyr Gly Ile Lys Ala Arg Val Val Ser Phe Pro Cys Gln Arg Leu
    610                 615                 620
Phe Glu Gln Gln Arg Arg Ser Tyr Lys Gln Ser Val Leu Lys Pro Gly
625                 630                 635                 640
Ser Gly Lys Pro Thr Val Val Ile Glu Ala Tyr Ala Ala Asn Gly Trp
                645                 650                 655
Glu Arg Tyr Ala Asp Ala Ser Val Ser Met Arg Arg Phe Gly Lys Ser
                660                 665                 670
Leu Pro Ser Lys Ala Ala Tyr Glu Tyr Phe Gly Tyr Glu Ala Asp Lys
            675                 680                 685
Ile Ala Leu Lys Ile Lys Asp Leu Val Glu Glu Val Arg Lys Asp Gly
```

```
                690                 695                 700
Ile Gln Val Leu Arg Gly Asp Phe Arg Asp Leu Asn Gly Tyr Leu Gly
705                 710                 715                 720

Ser Pro Ala Val Gly Asp Met Ile Asp His Leu Thr His Gly Arg Tyr
                725                 730                 735

Arg Ser Arg Thr His Arg Val Arg Arg Pro Ala Pro Gly Ser Ala Pro
            740                 745                 750

Arg Phe Ser Phe Pro Pro Phe Phe Glu Phe Ala Trp Gly Ala Glu Met
        755                 760                 765

Lys Arg Leu Pro Leu Asp His Leu Ala Pro Gln Ser Asp Lys Glu Arg
    770                 775                 780

Gln Leu Ala Lys Gln Arg Trp Ala Ala Thr Thr Phe Pro Gly Val Glu
785                 790                 795                 800

Gly Lys Leu Ser Gln Tyr Leu Leu
                805

<210> SEQ ID NO 24
<211> LENGTH: 754
<212> TYPE: PRT
<213> ORGANISM: Aspergillus terreus

<400> SEQUENCE: 24

Met Ala Pro Ser Leu Glu Pro Leu Glu Leu Leu Glu Lys Pro Ala Ala
1               5                   10                  15

Thr Leu Pro Val Lys Ala Ile Gly Asn Gly Ala Ser Leu Lys Tyr Glu
            20                  25                  30

Ser Pro Glu Lys His Gln Arg Val Met Asn Val Phe Arg Ala Phe Ile
        35                  40                  45

Ala Asp Leu Ala Gln Gln Tyr Gly Glu Gly His Ala Gly Ser Pro Met
    50                  55                  60

Gly Met Ala Ala Ile Gly Ile Ala Leu Tyr Lys Tyr Val Met Lys Tyr
65                  70                  75                  80

Ser Pro Thr Asn Cys Asn Tyr Phe Asn Arg Asp Arg Phe Val Leu Ser
                85                  90                  95

Asn Gly His Ala Cys Leu Trp Gln Tyr Leu Phe Met His Leu Val Gly
            100                 105                 110

Val Lys Ser Met Thr Leu Asp Gln Leu Lys Ser Tyr His Ser Ser Arg
        115                 120                 125

Leu Asp Ser Val Cys Pro Gly His Pro Glu Ile Glu His Glu Gly Val
    130                 135                 140

Glu Val Thr Thr Gly Pro Leu Gly Gln Gly Leu Ala Asn Ala Val Gly
145                 150                 155                 160

Leu Ala Val Ala Thr Lys Asn Leu Ala Ala Thr Tyr Asn Lys Pro Gly
                165                 170                 175

His Glu Val Val Asn Asn Met Thr Trp Cys Met Val Gly Asp Ala Cys
            180                 185                 190

Leu Gln Glu Gly Val Gly Leu Glu Ala Leu Ser Leu Ala Gly His Trp
        195                 200                 205

Lys Leu Asn Asn Leu Cys Val Ile Phe Asp Asn Asn Cys Val Thr Cys
    210                 215                 220

Asp Gly Thr Ala Asp Val Ala Asn Thr Glu Asp Ile Asn Thr Lys Met
225                 230                 235                 240

Arg Ala Thr Gly Phe Asn Val Val Asp Val His Asn Gly Asp Ser Asp
                245                 250                 255
```

```
Val Ala Ala Ile Ala Asn Ala Leu Ile Ala Ala Arg Ser Ser Asp Lys
            260                 265                 270

Pro Thr Phe Leu Asn Ile Arg Thr Thr Ile Gly Phe Gly Ala Ala Lys
        275                 280                 285

Ala Gly Thr Ala Asp Val His Gly Ala Ala Leu Gly Val Asp Glu Val
        290                 295                 300

Ala Arg Ile Lys Arg Ser Tyr Gly Leu Asn Pro Asp Glu His Phe His
305                 310                 315                 320

Ile Pro Gln Asp Val Tyr Asp Phe Phe His Asp Ile Pro Ser Arg Gly
            325                 330                 335

Glu Ala Leu Glu Val Gly Trp Gln Ala Ala Leu Val Lys Tyr His Glu
            340                 345                 350

Glu Tyr Pro Asp Leu Ala Ala Glu Phe Ala Leu Arg Val Ala Gly Lys
        355                 360                 365

Met Thr Ser Asp Trp Thr Lys Cys Ile Pro Arg Lys Glu Glu Gln Pro
        370                 375                 380

Thr Ala Ser Thr Ala Thr Arg Lys Ser Ala Gly Val Ile Thr Asn Ala
385                 390                 395                 400

Leu Gly Glu Arg Ile Asn Ser Phe Leu Val Gly Thr Ala Asp Leu Thr
            405                 410                 415

Pro Ser Cys Asn Ile Ala Tyr Lys Asn Lys Val Asp Phe Gln Ser Val
        420                 425                 430

Ser Ala His Pro Asn Ser His Thr Pro Thr Gln Ala Pro Asn Thr Asn
        435                 440                 445

Gln Pro Ser Leu Gln Thr Ala Cys Gly Leu Asn Gly Thr Tyr Ser Gly
    450                 455                 460

Arg Tyr Ile His Tyr Gly Ile Arg Glu His Ala Met Cys Ala Ile Ser
465                 470                 475                 480

Asn Gly Leu Ala Ala Phe Asn Lys Gly Thr Phe Ile Pro Leu Thr Ser
            485                 490                 495

Thr Tyr Phe Val Phe His Leu Tyr Ala Ala Ala Val Arg Met Ala
        500                 505                 510

Ala Leu Gln Gly Leu Gln Gln Ile His Ile Ala Thr His Asp Ser Ile
    515                 520                 525

Gly Val Gly Glu Asn Gly Pro Thr His Gln Pro Val Ala Val Ala Ala
    530                 535                 540

Leu Tyr Arg Ala Met Pro Asn Leu Leu Tyr Ile Arg Pro Cys Asp Ala
545                 550                 555                 560

Glu Glu Val Ala Ala Ala Tyr Thr Ala Ala Leu Arg Ala Ser His Thr
            565                 570                 575

Pro Thr Val Ile Ser Leu Ser Arg Gln Ser Leu Pro Gln Tyr Pro Gln
        580                 585                 590

His Ser Ser Arg Glu Gly Ala Leu Lys Gly Ala Tyr Val Phe Ala Glu
        595                 600                 605

Ala Glu Gly Gly Glu Phe Asp Val Thr Leu Ile Gly Val Gly Ser Glu
    610                 615                 620

Met Val Phe Ala Met Gln Thr Arg Glu Leu Leu Trp Ala Glu Tyr Gly
625                 630                 635                 640

Ile Arg Ala Arg Val Val Ser Phe Pro Cys Thr Arg Leu Phe Glu Leu
            645                 650                 655

Gln Ser Arg Glu Tyr Lys Leu Ser Val Leu Arg Pro Gly Asp Gly Lys
        660                 665                 670

Pro Thr Val Val Ile Glu Ala Tyr Pro Ala Asn Gly Trp Glu Arg Tyr
```

```
                     675                 680                 685
Ala Asp Ala Ser Val Ser Met Asn Ser Phe Gly Lys Ser Leu Pro Ser
            690                 695                 700
Lys Glu Val Tyr Glu His Phe Gly Phe Ala Pro Glu Ser Ile Ala Pro
705                 710                 715                 720
Lys Val Lys Asp Leu Val Glu Val Arg Asp Gly Ile Gly Val
                725                 730                 735
Leu Arg Gly Asp Phe Arg Asp Phe Asn Gly Gly Leu Arg Ile Gly Val
            740                 745                 750
Glu His
```

<210> SEQ ID NO 25
<211> LENGTH: 720
<212> TYPE: PRT
<213> ORGANISM: Rasamsonia emersonii

<400> SEQUENCE: 25

```
Met Thr Ile Glu Gln Ala His Leu Asn Gly Ser Thr Ala Glu Asn Asp
1               5                   10                  15
Gly Thr Asn Gln Val Ser Ser Ala Leu Pro Leu Val Lys Lys Leu
            20                  25                  30
Ser Lys Asp His Asp Leu Val Leu Lys Thr Phe Arg Leu Leu Val Ala
        35                  40                  45
Asp Leu Cys Gln Gln Phe Asn Gly Gly His Pro Gly Gly Ala Ile Gly
    50                  55                  60
Met Ala Ala Ile Gly Val Ala Leu Trp Arg Tyr Val Met Arg Tyr Ala
65              70                  75                  80
Pro His Thr Pro Asp Tyr Phe Asn Arg Asp Arg Phe Val Leu Ser Asn
                85                  90                  95
Gly His Ala Cys Leu Phe Gln Tyr Val Phe Leu His Leu Thr Gly Tyr
            100                 105                 110
Lys Ala Met Thr Phe Asp Gln Leu Lys Ser Tyr His Ser Asp Arg Val
        115                 120                 125
Asp Ala Leu Cys Pro Gly His Pro Glu Ile Glu His Glu Gly Ile Glu
    130                 135                 140
Val Thr Thr Gly Pro Leu Gly Gln Gly Val Ala Asn Ala Val Gly Leu
145                 150                 155                 160
Ala Met Ala Thr Lys His Leu Thr Ala Thr Tyr Asn Arg Pro Gly Tyr
                165                 170                 175
Glu Val Val Ser Asn His Thr Trp Cys Met Val Gly Asp Ala Cys Leu
            180                 185                 190
Gln Glu Gly Val Ala Leu Glu Ala Ile Ser Phe Ala Gly His Leu Arg
        195                 200                 205
Leu Asn Asn Leu Thr Val Ile Tyr Asp Asn Asn Gln Ile Thr Cys Asp
    210                 215                 220
Gly Ser Val Asp Leu Thr Asn Thr Glu Asp Val Asn Ala Lys Met Arg
225                 230                 235                 240
Ala Cys Gly Trp Asp Val Ile Asp Val Glu Asp Gly Cys Phe Asp Val
                245                 250                 255
Glu Gly Ile Val Gln Ala Leu Glu Gln Ala Arg Ala Ser Ser Asp Lys
            260                 265                 270
Pro Thr Phe Ile Asn Val Arg Thr Ile Ile Gly Leu Gly Ser Lys Val
        275                 280                 285
Ala Gly Thr Ala Asp Ala His Gly Val Ala Phe Glu Ala Glu Asp Val
```

```
            290                 295                 300
Ala Ala Gln Lys Lys Ala Tyr Gly Phe Asn Pro Asp Glu Leu Phe Val
305                 310                 315                 320

Ile Ser Asp Thr Val Arg Glu Phe Phe Ala Asp Leu Pro Ala Arg Gly
                325                 330                 335

Glu Ala Leu Val Gln Glu Trp Asn Lys Leu Val Asp Glu Tyr Ser Ala
                340                 345                 350

Lys Tyr Pro Asp Leu Gly Ala Glu Phe Arg Arg Ile Arg Gly Glu
                355                 360                 365

Leu Pro Ala Asn Trp Lys Asp Leu Ile Pro Thr Ser Phe Pro Asp Lys
    370                 375                 380

Pro Thr Pro Ser Arg Ala Ser Ser Gly Leu Val Phe Asn Pro Val Ala
385                 390                 395                 400

Lys Glu Ile Asn Ser Phe Val Val Gly Thr Ala Asp Leu Ser Pro Ser
                405                 410                 415

Val Asn Met Ala Trp Pro Gly Lys Val Asp Phe Gln His Pro Asp Leu
                420                 425                 430

Arg Thr Thr Cys Gly Leu Asn Gly Asn Tyr Ser Gly Arg Tyr Ile His
                435                 440                 445

Tyr Gly Val Arg Glu His Ala Met Cys Ala Ile Ala Asn Gly Leu Ala
    450                 455                 460

Ala Phe Ala Pro Asn Thr Ile Ile Pro Val Thr Ser Ser Phe Phe Met
465                 470                 475                 480

Phe Tyr Leu Tyr Ala Ala Pro Ala Val Arg Met Gly Ala Leu Gln Gln
                485                 490                 495

Leu Gln Ile Ile His Ala Ala Thr His Asp Ser Ile Gly Met Gly Glu
                500                 505                 510

Asp Gly Pro Thr His Gln Pro Ile Glu Leu Ala Ser Leu Phe Arg Ser
                515                 520                 525

Met Pro Asn Leu Leu Tyr Ile Arg Pro Gly Asp Ser Glu Glu Thr Ala
    530                 535                 540

Gly Ala Trp Ile Val Ala Ile Glu Ala Lys Arg Thr Pro Thr Ile Ile
545                 550                 555                 560

Ser Thr Ser Arg His Ala Val Pro Gln Leu Lys Gln Thr Arg Arg Glu
                565                 570                 575

Gly Val Ala Arg Gly Ala Tyr Val Leu Glu Glu Val Ala Asp Lys Arg
                580                 585                 590

Ala Asp Val Thr Leu Ile Gly Val Gly Ala Glu Leu Ser Phe Ala Val
                595                 600                 605

Glu Val Ala Gln Gln Leu Lys Lys Arg Asn Ile Ala Ala Arg Val Val
    610                 615                 620

Ser Phe Pro Cys Gln Arg Leu Phe Glu Gln Pro Val Glu Tyr Arg
625                 630                 635                 640

Arg Glu Thr Leu Gln Arg His Arg Gly Ile Pro Ala Val Val Ile Glu
                645                 650                 655

Pro Tyr Thr Pro Asn Gly Trp Glu Arg Tyr Ala Asp Ala Gly Ile Cys
                660                 665                 670

Leu Lys Arg Phe Gly His Ser Leu Pro Gly Lys Ala Ala Tyr Lys Phe
                675                 680                 685

Phe Gly Tyr Glu Ile Asp Val Leu Thr Gly Lys Val Val Asp Tyr Leu
    690                 695                 700

Glu Arg Ile Arg Glu Asp Glu Leu Leu Arg Arg Glu Phe Val Glu Leu
705                 710                 715                 720
```

<210> SEQ ID NO 26
<211> LENGTH: 741
<212> TYPE: PRT
<213> ORGANISM: Exophiala aquamarina

<400> SEQUENCE: 26

```
Met Ala Pro Ser Leu Glu Tyr Tyr Glu Ala Val Ser Gly Gly Glu Leu
1               5                   10                  15

Pro Val Lys Ala Ile Pro Thr Lys Thr Asn Gly Val Glu Ala Val Ser
            20                  25                  30

Gly Leu Gln Leu Asp Gln Ser Glu Lys His Glu Ile Ile Leu Lys Thr
        35                  40                  45

Phe Arg Ala Phe Ile Ala Asp Leu Cys Gln Gln Phe Gly Gly His
    50                  55                  60

Pro Gly Gly Ala Met Gly Met Ala Ala Ile Gly Ile Ala Leu Tyr Lys
65                  70                  75                  80

Tyr Val Met Lys Tyr Ser Pro Thr Asn Val Gly Phe Phe Asn Arg Asp
                85                  90                  95

Arg Phe Val Leu Ser Asn Gly His Thr Cys Leu Phe Gln Tyr Leu Phe
            100                 105                 110

Met His Leu Val Gly Phe Lys Ser Met Thr Met Glu Gln Leu Lys Ser
        115                 120                 125

Tyr His Ser Asp Arg Thr Asp Ser Leu Ala Pro Gly His Pro Glu Ile
    130                 135                 140

Glu Asn Glu Gly Val Glu Val Thr Thr Gly Pro Leu Gly Gln Gly Val
145                 150                 155                 160

Ala Asn Ala Val Gly Leu Ala Met Ala Thr Lys His Leu Gly Ala Thr
                165                 170                 175

Tyr Asn Arg Pro Gly His Thr Val Val Asp Asn Met Thr Trp Cys Met
            180                 185                 190

Ile Gly Asp Ala Cys Leu Gln Glu Gly Val Ala Leu Glu Ala Val Ala
        195                 200                 205

Leu Ala Gly His Trp Lys Leu Asn Asn Leu Ala Ile Leu Tyr Asp Asn
    210                 215                 220

Asn Asn Ile Thr Cys Asp Gly Ser Ala Asp Val Ala Cys Thr Glu Asp
225                 230                 235                 240

Ile Asp Ala Lys Met Gln Ala Cys Gly Trp Asn Val Ile Asp Val Tyr
                245                 250                 255

Asp Gly Asp His Asn Val Thr Gly Ile Val Gln Ala Leu Leu Thr Ala
            260                 265                 270

Arg Ile Ser Gln Lys Pro Thr Phe Ile Asn Ile Arg Thr Ile Ile Gly
        275                 280                 285

Ile Gly Ser Ala Ala Thr Asn Asn Ala Lys Ala His Gly Ala Ala Phe
    290                 295                 300

Gly Val Asp Asp Val Ala Gln Ile Lys Arg Asn Phe Gly Leu Asp Pro
305                 310                 315                 320

Glu Lys His Phe Glu Ile Ser Lys Asp Ile Tyr Gly Phe Phe Glu Asp
                325                 330                 335

Val Lys His Arg Gly Glu Ser Leu Glu Ala Glu Trp Ser Ala Thr Val
            340                 345                 350

Lys Asp Tyr Glu Ala Gln Tyr Pro Glu Leu Ala Ala Glu Phe Lys Leu
        355                 360                 365

Arg Val Gln Gly Lys Met Pro Val Asp Trp Thr Lys Phe Ile Pro Ser
```

```
            370                 375                 380
Lys Asp Gln Leu Pro Thr Lys Pro Thr Ala Ser Arg Lys Ser Ala Gly
385                 390                 395                 400

Ile Val Cys Asn Ser Leu Ala Glu Asn Met Ser Asn Phe Leu Val Gly
                405                 410                 415

Thr Ala Asp Leu Thr Pro Ser Val Asn Leu Ser Tyr Lys Gln Gln Val
                420                 425                 430

Asp Phe Gln Ser Pro Asp Phe Val Ala Ala Cys Gly Met Thr Gly Ala
                435                 440                 445

Tyr Ser Gly Arg Tyr Ile His Tyr Gly Ile Arg Glu His Ala Met Cys
                450                 455                 460

Ala Ile Ser Asn Gly Leu Val Ala Phe Asn Arg Gly Thr Phe Leu Pro
465                 470                 475                 480

Val Thr Ser Thr Phe Phe Met Phe Tyr Ile Tyr Ala Ala Pro Ala Val
                485                 490                 495

Arg Met Gly Ala Leu Gln Gly Leu Gln Gln Ile His Ile Ala Thr His
                500                 505                 510

Asp Ser Ile Gly Thr Gly Glu Asp Gly Pro Thr His Gln Pro Ile Ala
                515                 520                 525

Leu Pro Ala Leu Tyr Arg Ala Met Pro Asn Leu Leu Tyr Ile Arg Pro
530                 535                 540

Cys Asp Ser Glu Glu Val Ala Gly Ala Phe Ile Thr Ala Ile Lys Ala
545                 550                 555                 560

Thr Ser Thr Pro Ser Ile Ile Ser Leu Ser Arg Gln Asn Leu Thr Gln
                565                 570                 575

Phe Pro Glu Tyr Ser His Arg Asp Gly Val Gln Arg Gly Ala Tyr Val
                580                 585                 590

Phe Ile Glu Asp Ala Ala Ala Asp Ile Thr Leu Ile Gly Ile Gly Ser
                595                 600                 605

Glu Met Gly Phe Ala Val Ser Thr Arg Thr Leu Leu Lys Glu Arg Tyr
                610                 615                 620

Asn Ile Asn Ala Arg Ile Val Ser Phe Pro Cys Gln Arg Leu Phe Glu
625                 630                 635                 640

Gln Gln Ser Arg Asp Tyr Lys Glu Ser Val Leu Arg Tyr Lys Ser Ser
                645                 650                 655

Cys Pro Ile Val Val Ile Glu Ala Tyr Ala Val Asn Gly Trp Glu Arg
                660                 665                 670

Tyr Ala Asp Ala Gly Val Ser Met Lys Ser Phe Gly Lys Ser Leu Pro
                675                 680                 685

Gly Asp Val Ala Tyr Arg His Phe Gly Phe Glu Pro Ser Val Met Ser
                690                 695                 700

Gln Lys Ile Lys Gly Phe Val Glu Glu Val Arg Ala Met Asp Gly Gly
705                 710                 715                 720

Val Arg Ala Leu Arg Gly Glu Phe Arg Asp Leu Asn Gly Val Met Gly
                725                 730                 735

Phe Gly Phe Glu His
                740

<210> SEQ ID NO 27
<211> LENGTH: 730
<212> TYPE: PRT
<213> ORGANISM: Magnaporthe oryzae

<400> SEQUENCE:

-continued

```
Met Ala Ser Ser Glu Gln Ser Ser Thr Ala Leu Ser Ser Gln Arg Lys
1               5                   10                  15

Pro Leu Asp Leu Pro Gln Leu Lys Ser Glu Glu Asp His Asp Val Val
                20                  25                  30

Leu Lys Thr Ile Arg Met Leu Val Ala Asp Leu Cys Gln Gln Phe Gly
            35                  40                  45

Gly Gly His Pro Gly Gly Ala Ile Gly Met Ala Ala Ile Gly Val Ala
        50                  55                  60

Leu Trp Lys Tyr Val Met Arg Tyr Ser Pro Glu Pro Glu Tyr Phe
65                  70                  75                  80

Asn Arg Asp Arg Phe Val Leu Ser Asn Val Gly Ala Ser Val Lys Leu
                85                  90                  95

Thr Leu Gly Leu Ser Thr Gly His Thr Cys Leu Phe Gln Tyr Val Phe
            100                 105                 110

Leu His Leu Ser Gly Tyr Lys Ala Met Thr Phe Asp Gln Leu Lys Ser
        115                 120                 125

Tyr His Ser Lys Arg Thr Asp Ala Leu Cys Pro Gly His Pro Glu Ile
    130                 135                 140

Glu His Glu Gly Val Glu Val Thr Thr Gly Pro Leu Gly Gln Gly Val
145                 150                 155                 160

Ala Asn Ala Val Gly Leu Ala Met Ala Thr Lys Asn Leu Ala Ser Thr
                165                 170                 175

Tyr Asn Arg Pro Gly Phe Pro Val Val Asp Asn His Thr Trp Cys Met
            180                 185                 190

Ile Gly Asp Ala Cys Leu Gln Glu Gly Val Ala Leu Glu Ala Ile Ser
        195                 200                 205

Leu Ala Gly His Leu Ala Leu Asp Asn Leu Thr Ile Ile Tyr Asp Asn
    210                 215                 220

Asn Gln Ile Thr Cys Asp Gly Ser Val Asp Leu Thr Asn Thr Glu Asp
225                 230                 235                 240

Val Asn Ala Lys Met Arg Ala Cys Gly Trp His Thr Val Asp Val Glu
                245                 250                 255

Asp Gly Cys Phe Asp Ile Gly Gly Ile Val Arg Ala Leu Ala Glu Ala
            260                 265                 270

Arg Gln Ala Ala His Gly Lys Pro Thr Phe Ile Asn Val Arg Thr Val
        275                 280                 285

Ile Gly Leu Gly Ser Ala Val Ala Gly Lys Ala Glu Ala His Gly Ala
    290                 295                 300

Ala Phe Gly Ala Ala Asp Val Ala Asn Met Lys Arg Ser Val Gly Phe
305                 310                 315                 320

Asp Pro Glu Gln His Phe Val Ile Gly Asp Lys Val Arg Asp Phe Phe
                325                 330                 335

Ala Asp Ile Pro Lys Arg Gly His Asn Leu Val Ala Asp Trp Lys Gly
            340                 345                 350

Leu Val Ser Lys Tyr Ala Glu Ala His Pro Glu Val Ala Ser Glu Phe
        355                 360                 365

Asp Arg Arg Thr Lys Gly Glu Leu Pro Glu Asn Trp Arg Glu Leu Ile
    370                 375                 380

Pro Lys Ser Phe Ser Asp Lys Pro Thr Ala Thr Arg Ala Ser Ser Gly
385                 390                 395                 400

Leu Val Leu Asn Pro Ile Ala Lys Asp Val Lys Ser Phe Met Val Gly
                405                 410                 415

Thr Ala Asp Leu Thr Pro Ser Val His Met Thr Trp Asp Gly Met Glu
```

```
                    420                 425                 430
Asp Phe Gln Asn Pro Asn Ile Arg Pro Thr Cys Gly Ile Asn Gly Ser
                435                 440                 445

Tyr Thr Gly Arg Tyr Ile His Tyr Gly Val Arg Glu His Ala Met Cys
            450                 455                 460

Ala Ile Ser Asn Gly Leu Ala Ala Phe Asn Pro Gly Thr Phe Val Pro
465                 470                 475                 480

Val Thr Ser Ser Phe Phe Met Phe Tyr Leu Tyr Ala Ala Pro Ala Val
                485                 490                 495

Arg Met Gly Ala Leu Gln Lys Leu Gln Val Ile His Ala Ala Thr His
            500                 505                 510

Asp Ser Ile Gly Met Gly Glu Asp Gly Pro Thr His Gln Pro Ile Glu
            515                 520                 525

Leu Ala Thr Leu Phe Arg Ala Met Pro Asn Leu Leu Tyr Met Arg Pro
            530                 535                 540

Ala Asp Ser Glu Glu Thr Ala Gly Ala Trp Glu Val Ala Ile Ala Glu
545                 550                 555                 560

Arg Thr Arg Pro Ser Ile Val Ser Thr Ser Arg His Lys Leu Pro Gln
                565                 570                 575

Leu Val Gly Lys Ser Ser Arg Lys Gly Val Ala Lys Gly Ala Tyr Val
                580                 585                 590

Val Ser Glu Pro Ala Asp Gly Lys Ala Asp Val Thr Ile Leu Gly Val
            595                 600                 605

Gly Ala Glu Leu Cys Leu Ala Leu Asp Val Ala Glu Ala Leu Ala Gly
            610                 615                 620

Lys Asn Ile Lys Val Arg Val Val Ser Phe Pro Cys Trp Arg Leu Phe
625                 630                 635                 640

Asp Glu Gln Pro Val Ala Tyr Arg Arg Glu Thr Leu Arg Arg His Glu
                645                 650                 655

Gly Ile Pro Ala Val Val Glu Pro Tyr Ala Pro Asn Gly Trp Glu
            660                 665                 670

Arg Tyr Ala Asp Ala Gly Val Cys Leu Arg Arg Phe Gly His Ser Leu
            675                 680                 685

Pro Gly Pro Glu Ala Tyr Lys Tyr Phe Glu Tyr Glu Thr Pro Lys Val
            690                 695                 700

Thr Glu Lys Ile Glu Gly Tyr Leu Lys Gly Leu Glu Thr Gly Glu Trp
705                 710                 715                 720

Leu Arg Gly Glu Phe Ala Asp Leu Gln Ile
                725                 730

<210> SEQ ID NO 28
<211> LENGTH: 721
<212> TYPE: PRT
<213> ORGANISM: Verruconis gallopava

<400> SEQUENCE: 28

Met Ala Pro Gly Leu Val Phe Ala Pro Val Val Asp Gly Gln Pro Ala
1               5                   10                  15

Ala Lys Ser Val Leu Pro Glu Gly Ser Phe Pro Thr Gly Asn Glu Leu
            20                  25                  30

Ile Ser Lys His Asp Ile Val Leu Lys Thr Phe Arg Leu Leu Ile Ala
        35                  40                  45

Asp Leu Cys Glu Gln Phe Lys Gly Gly His Pro Gly Gly Ala Ile Gly
    50                  55                  60
```

-continued

```
Met Ala Ala Ile Gly Val Ala Leu Trp Arg Tyr Val Met Gln Tyr Ala
 65                  70                  75                  80

Pro His Thr Pro Asp Phe Phe Asn Arg Asp Arg Phe Val Leu Ser Asn
                 85                  90                  95

Gly His Thr Cys Leu Phe Gln Tyr Thr Phe Leu His Leu Thr Gly Tyr
                100                 105                 110

Lys Ala Met Asn Phe Asp Gln Leu Lys Ser Tyr His Ser Gln Arg Thr
                115                 120                 125

Asp Ser Leu Cys Pro Gly His Pro Glu Ile Glu Ile Glu Gly Ile Glu
130                 135                 140

Val Thr Thr Gly Pro Leu Gly Gln Gly Val Ala Asn Ser Val Gly Leu
145                 150                 155                 160

Ala Met Ala Ser Lys His Leu Gly Thr Lys Phe Asn Arg Pro Gly Phe
                165                 170                 175

Pro Val Val Ser Asn His Ile Trp Cys Met Ile Gly Asp Ala Cys Leu
                180                 185                 190

Gln Glu Gly Val Ala Leu Glu Ala Ile Ser Phe Ala Gly His Leu Arg
                195                 200                 205

Leu Asn Asn Leu Thr Ile Ile Tyr Asp Asn Asn Gln Ile Thr Cys Asp
210                 215                 220

Gly Ser Val Asp Leu Thr Asn Thr Glu Asp Val Asn Ala Lys Met Arg
225                 230                 235                 240

Ala Cys Gly Trp Asp Val Ile Asp Val Glu Asp Ala Asn Phe Glu Val
                245                 250                 255

Met Ala Ile Val Glu Ala Leu Glu Lys Ala Lys Ser Ser Ala His Lys
                260                 265                 270

Pro Thr Phe Ile Asn Cys Arg Thr Val Ile Gly Leu Gly Ser Ala Val
                275                 280                 285

Ala Gly Gln Ala Gln Ala His Gly Ala Ala Phe Gly Glu Lys Asp Val
                290                 295                 300

Glu Ala Met Lys Thr Ala Ala Gly Phe Asp Pro Lys Gln Lys Phe Val
305                 310                 315                 320

Val Pro Asp Val Val Arg Glu Phe Phe Ala Asp Leu Pro Glu Arg Gly
                325                 330                 335

Gln Lys Ile Val Glu Gln Trp Asn Asp Leu Val Lys Arg Tyr Ala Thr
                340                 345                 350

Glu Tyr Pro Ser Leu Ala Ala Glu Phe Gln Ser Arg Phe Arg Gly Glu
                355                 360                 365

Leu Pro Ser Asn Trp Glu Asp Leu Val Pro Asn Ser Phe Pro Glu Lys
                370                 375                 380

Pro Thr Pro Ser Arg Ala Ser Ser Gly Leu Val Leu Asn Pro Ile Ala
385                 390                 395                 400

Lys Asn Val Asp Ala Phe Met Val Gly Thr Ala Asp Leu Ser Pro Ser
                405                 410                 415

Val His Met Thr Trp Pro Gly Lys Val Asp Phe Gln His Pro Asp Leu
                420                 425                 430

Arg Thr Ser Cys Gly Ile Asn Gly Asp Tyr Thr Gly Arg Tyr Ile His
                435                 440                 445

Tyr Gly Val Arg Glu His Ala Met Cys Ala Ile Ser Asn Gly Leu Ala
                450                 455                 460

Ala Tyr Ala Pro Asn Thr Ile Ile Pro Val Thr Ser Ser Phe Phe Met
465                 470                 475                 480

Phe Tyr Leu Tyr Ala Ala Pro Ala Val Arg Met Gly Ala Leu Gln Arg
```

```
            485                 490                 495
Leu Gln Val Ile His Ala Ala Thr His Asp Ser Ile Gly Met Gly Glu
            500                 505                 510

Asp Gly Pro Thr His Gln Pro Ile Glu Leu Ala Thr Leu Tyr Arg Ala
            515                 520                 525

Met Pro Asn Leu Leu Tyr Ile Arg Pro Ala Asp Ser Glu Glu Thr Ala
        530                 535                 540

Gly Ala Trp Ile Thr Ala Ile Lys Ala Lys Asn Thr Pro Ser Ile Ile
545                 550                 555                 560

Ser Thr Ser Arg His Ala Val Pro Gln Leu Lys Gln Thr Arg Arg Glu
                565                 570                 575

Lys Val Ala Leu Gly Ala Tyr Val Leu Glu Val Asp Asp Glu Lys
            580                 585                 590

Pro Asp Leu Thr Leu Ile Gly Val Gly Ala Glu Leu Ser His Ala Leu
            595                 600                 605

Ala Val Ala Glu Asn Leu Arg Arg Asp Arg Asn Leu Arg Val Arg Val
        610                 615                 620

Val Ser Phe Pro Cys Trp Arg Leu Phe Glu Gln Gln Pro Val Glu Tyr
625                 630                 635                 640

Lys Arg Ser Val Leu Lys Arg His Leu Ser Ile Pro Ala Val Ala Ile
                645                 650                 655

Glu Pro Tyr Ala Pro Asn Gly Trp Glu Arg Tyr Ala Asn Ala Ala Ala
            660                 665                 670

Ser Met Thr Arg Phe Gly His Ser Leu Pro Gly Thr Ala Ala Tyr Lys
        675                 680                 685

Tyr Phe Gly Phe Asp Val Asp Gly Leu Thr Val Lys Val Gly Asn Tyr
690                 695                 700

Leu Asp Ala Ile Glu Arg Asp Pro Val Leu Arg Thr Glu Phe Val Glu
705                 710                 715                 720

Leu

<210> SEQ ID NO 29
<211> LENGTH: 703
<212> TYPE: PRT
<213> ORGANISM: Debaryomyces hansenii

<400> SEQUENCE: 29

Met Asn Gln Ile Glu Asp Leu Ser Leu Lys Thr Ile Arg Cys Leu Val
1               5                   10                  15

Ser Asp Leu Val Gln Gln Tyr Asn Gly Gly His Pro Gly Gly Ala Met
            20                  25                  30

Gly Met Ala Ala Ile Gly Ile Ala Leu Trp Lys Tyr Ile Leu Lys Tyr
        35                  40                  45

Asn Pro Lys Asn Ala Asn Trp Phe Asn Arg Asp Arg Phe Val Leu Ser
    50                  55                  60

Asn Gly His Thr Cys Leu Phe Gln Tyr Val Phe Leu His Leu Val Gly
65                  70                  75                  80

Tyr Glu Ser Phe Thr Met Asn Gln Leu Lys Lys Tyr His Ala Pro Glu
                85                  90                  95

Val Ser Gln Cys Ala Gly His Pro Glu Ile Glu Phe Glu Gly Ile Glu
            100                 105                 110

Val Thr Thr Gly Pro Leu Gly Gln Gly Ile Ala Asn Ala Val Gly Leu
        115                 120                 125

Ala Ile Ala Ser Lys Asn Leu Ala Ala Asn Tyr Asn Lys Pro Asp Leu
```

```
            130                 135                 140
Asp Leu Val Asp Asn Lys Ile Tyr Cys Met Val Gly Asp Ala Cys Ile
145                 150                 155                 160

Gln Glu Gly Val Gly Leu Glu Ala Ile Ser Leu Ala Gly His Leu Gly
                165                 170                 175

Leu Asp Asn Leu Ile Val Ile Tyr Asp Asn Asn Gln Ile Thr Cys Asp
                180                 185                 190

Gly Ser Val Asp Leu Ala Asn Ser Glu Asp Ile Asn Ala Lys Phe Met
            195                 200                 205

Ala Gln Lys Trp His Val Leu Thr Val Asp Asp Gly Ser Phe Asp Leu
        210                 215                 220

Arg Ser Ile Leu Ala Ala Ile Glu Gln Ala Lys Ser Val Lys Gly Ser
225                 230                 235                 240

Pro Ile Leu Ile Asn Ile Arg Thr Ile Ile Gly Val Asp Thr Asn Val
                245                 250                 255

Ala Asn Asn Ala Lys Ala His Gly Ala Ala Tyr Gly Val Glu Glu Gly
            260                 265                 270

Arg Arg Leu Lys Ala Leu Tyr Gly Phe Asp Pro Asp Gln Phe Ile Glu
        275                 280                 285

Val Pro Lys Leu Val Tyr Asp Phe Phe Arg Glu Gly Asn Glu Gly Ala
290                 295                 300

Ile Ser Lys Gly Val Phe His Gln Glu Gln Trp Glu Lys Lys Leu Glu
305                 310                 315                 320

Ala Tyr Ser Lys Lys Tyr Pro Gln Leu Tyr Glu Glu Val Val Ser Arg
                325                 330                 335

Ile Asn Gly Lys Leu Pro Thr Asp Trp Lys Glu Ser Leu Pro His Ser
            340                 345                 350

Leu Pro Thr Asp Ala Thr Ala Ser Arg Lys Ala Ser Gly Leu Val Phe
        355                 360                 365

Thr Pro Leu Ala Ala Lys Tyr Pro Gln Phe Leu Val Gly Thr Ala Asp
        370                 375                 380

Leu Ser Pro Ser Val Asn Leu Leu Trp Pro His Lys Lys Asp Phe Gln
385                 390                 395                 400

Asn Pro Glu Ile Lys Thr Asp Cys Gly Ile Asn Gly Asp Tyr Ser Gly
                405                 410                 415

Arg Tyr Leu His Tyr Gly Ile Arg Glu His Ala Met Cys Ala Ile Ser
            420                 425                 430

Asn Gly Ile Ser Ala Tyr Ser Lys Gly Ala Phe Ile Pro Ile Thr Ser
        435                 440                 445

Ser Phe Phe Met Phe Tyr Leu Tyr Ser Ala Pro Ala Val Arg Met Gly
    450                 455                 460

Ala Leu Gln Asn Leu Gln Val Ile His Val Ala Thr His Asp Ser Ile
465                 470                 475                 480

Gly Thr Gly Glu Asp Gly Pro Thr His Gln Pro Ile Ala Leu Ala Ser
                485                 490                 495

Phe Tyr Arg Ser Leu Pro Asn Cys Leu Tyr Val Arg Pro Ala Asp Asn
            500                 505                 510

Glu Glu Val Ala Gly Ala Trp Glu Leu Ala Ile Glu Thr Thr Asn Lys
        515                 520                 525

Pro Thr Ile Ile Ser Leu Ser Arg Gln Asn Leu Lys Gln Tyr Pro Gly
530                 535                 540

Ile Thr Asp Arg Asn Lys Val Lys Phe Gly Ala Tyr Val Leu Lys Glu
545                 550                 555                 560
```

-continued

```
Phe Asp Ser Ser Ser Asp Ser Gln Lys Leu Gln Ile Ile Ser Val Gly
            565                 570                 575

Ala Glu Ser Gln Phe Ala Ile Asp Ala Ala Glu Ile Leu Ile Glu Ser
        580                 585                 590

Asn Ile Asn Val Lys Ile Ile Ser Phe Pro Cys Gln Arg Leu Phe Glu
    595                 600                 605

Cys Gln Ser Thr Glu Tyr Lys Arg Ser Val Leu Asp Pro Gln Ile Val
610                 615                 620

Thr Val Ala Ile Glu Ala Tyr Ala Ser Asn Gly Trp Glu Arg Tyr Ala
625                 630                 635                 640

Asn Ala Gly Phe His Leu Asn Glu Phe Gly Ile Ser Leu Pro Gly Lys
            645                 650                 655

Asn Ala Tyr Glu His Phe Gly Phe Asn Gly Ala Tyr Ile Ala Ser Lys
        660                 665                 670

Ile Gln Lys Tyr Leu Asp Asp Leu Gln Lys Asp Asp Ile Met Lys Phe
    675                 680                 685

Glu Tyr Gln Glu Leu Asn Ile Thr Lys Asn His His Ser Ser Ser
690                 695                 700
```

<210> SEQ ID NO 30
<211> LENGTH: 735
<212> TYPE: PRT
<213> ORGANISM: Fonsecaea erecta

<400> SEQUENCE: 30

```
Met Ser Pro Ile Ala Val Pro Val Glu Gly Gln Ser Met Gln Leu Pro
1               5                   10                  15

Asp Ala Asp Tyr Lys Leu Ala Asn Ser Val Lys Lys Gly Gln Thr Thr
            20                  25                  30

Ser Thr Thr Asn Ala Ser Thr Gln Leu Ser Pro Glu Glu Glu Leu Val
        35                  40                  45

Leu Lys Ser Phe Arg Val Leu Ile Ala Asp Leu Cys Gln Gln Phe Lys
    50                  55                  60

Gly Gly His Pro Gly Gly Ala Met Gly Met Ala Ala Ile Gly Val Ala
65                  70                  75                  80

Leu Trp Lys Tyr Val Met His Tyr Ala Pro His Ser Pro Asp Trp Ile
            85                  90                  95

Asn Arg Asp Arg Phe Val Leu Ser Asn Gly His Thr Cys Leu Phe Gln
            100                 105                 110

Tyr Cys Phe Leu His Leu Thr Gly Tyr Lys Ala Met Thr Leu Glu Gln
        115                 120                 125

Leu Lys Ser Tyr His Ser Asp Arg Thr Asp Ser Leu Cys Pro Gly His
    130                 135                 140

Pro Glu Ile Glu His Glu Gly Ile Glu Val Thr Thr Gly Pro Leu Gly
145                 150                 155                 160

Gln Gly Ile Ala Asn Ala Val Gly Met Ala Met Ala Ser Lys His Leu
            165                 170                 175

Ala Ala Lys Phe Asn Arg Pro Gly Phe Asp Ile Val Ser Asp His Val
        180                 185                 190

Trp Cys Met Val Gly Asp Ala Cys Leu Gln Glu Gly Val Gly Leu Glu
    195                 200                 205

Ala Ile Ser Phe Ala Gly His Met Arg Leu Gly Asn Leu Thr Val Ile
210                 215                 220

Tyr Asp Asn Asn Gln Ile Thr Cys Asp Gly Pro Val Ser Leu Thr Asn
```

```
                225                 230                 235                 240
Thr Glu Asp Ile Asn Ala Lys Met Arg Ala Cys Gly Trp Asn Val Ile
                    245                 250                 255
Glu Ile Ala Asp Gly Cys Trp Asp Val Arg Gly Ile Val Lys Ala Leu
                260                 265                 270
Glu Ala Ser Arg Val Ser Asp Arg Pro Thr Phe Val Asn Cys His Thr
            275                 280                 285
Val Ile Gly Val Asp Thr Ala Val Ala Gly Asp Ala Val Ala His Gly
        290                 295                 300
Ala Ala Leu Gly Val Asp Thr Val Met Ala Leu Lys Arg Leu Tyr Gly
305                 310                 315                 320
Phe Asp Pro Glu Gln Arg Tyr Val Ile Pro Asp Thr Val Arg Glu Phe
                325                 330                 335
Phe Ser Gly Leu Pro Ser Arg Gly Gln Ser Leu Val Thr Glu Trp Asn
            340                 345                 350
His Met Leu Gln Glu Tyr Ser Gln Val Tyr Pro Asp Leu Ala Glu Glu
        355                 360                 365
Tyr Ala Thr Arg Ile Ser Gly His Leu Pro Asp Ser Trp Glu Ser Leu
    370                 375                 380
Ile Pro His Pro Leu Pro Ser Lys Pro Thr Ala Thr Arg Ala Ala Ser
385                 390                 395                 400
Gly Leu Val Phe Asn Pro Leu Ala Glu Arg Leu Asp Arg Phe Met Val
                405                 410                 415
Gly Thr Ala Asp Leu Ser Pro Ser Val Tyr Met Ser Trp Lys Thr Lys
            420                 425                 430
Glu Asp Phe Glu Pro Pro Ser Leu Gly Thr Gly Ser Tyr Ser Gly Arg
        435                 440                 445
Phe Ile His Tyr Gly Val Arg Glu His Ala Met Ala Ala Ile Ser Asn
    450                 455                 460
Gly Leu Ala Ala Tyr His Pro Gly Met Phe Ile Pro Val Thr Ser Ser
465                 470                 475                 480
Phe Phe Met Phe Tyr Leu Tyr Ala Ala Pro Ala Val Arg Met Gly Ala
                485                 490                 495
Leu Gln His Leu Gln Val Ile His Ala Ala Thr His Asp Ser Ile Gly
            500                 505                 510
Met Gly Glu Asp Gly Pro Thr His Gln Pro Ile Glu Leu Ala Ala Leu
        515                 520                 525
Tyr Arg Ala Met Pro Asn Leu Leu Tyr Ile Arg Pro Gly Asp Ser Glu
    530                 535                 540
Glu Thr Ala Gly Ala Trp Ile Glu Ala Ile Lys Ala Arg His Met Ser
545                 550                 555                 560
Ser Ile Ile Ser Thr Ser Arg His Ala Leu Pro Gln Leu Thr Gly Leu
                565                 570                 575
Thr Lys Arg Thr Glu Val Ala Lys Gly Ala Tyr Val Leu Glu Glu Val
            580                 585                 590
Val Ser Gly Thr Ala Asp Leu Thr Leu Ile Gly Val Gly Ala Glu Leu
        595                 600                 605
Asn Leu Ala Val Arg Val Ala Ala Glu Leu Arg Ser Ser Ser His Gly
    610                 615                 620
Leu Lys Val Arg Thr Val Ser Phe Pro Cys Gln Arg Leu Phe Asp Ala
625                 630                 635                 640
Gln Pro Arg Ala Tyr Gln Arg His Val Leu Gln Arg Gln Ser Gly Val
                645                 650                 655
```

```
Pro Val Val Ile Glu Ala Tyr Ala Ala Asn Gly Trp Glu Arg Tyr
            660                 665                 670

Ala His Ala Ala Val Cys Met Ser Thr Lys Arg Phe Gly Lys Ser Leu
        675                 680                 685

Pro Gly Pro Lys Ala Tyr Glu Tyr Phe Gly Phe Asp Val Pro Ser Met
690                 695                 700

Val Ala Arg Ile Ala Gly Tyr Leu Asp Asp Trp Lys Ala Asp Pro Asp
705                 710                 715                 720

Leu Arg His Asp Phe Val Glu Leu Thr Cys Ala Lys Thr Asp Ala
                725                 730                 735

<210> SEQ ID NO 31
<211> LENGTH: 715
<212> TYPE: PRT
<213> ORGANISM: Baudoina compniacensis

<400> SEQUENCE: 31

Met Glu Pro Asn Asp Arg Thr Gln Tyr Val Val Arg Cys Tyr Arg Ala
1               5                   10                  15

Leu Ile Ala Asp Leu Cys Gln Gln Phe Asn Met Gly His Pro Gly Ser
            20                  25                  30

Ala Met Gly Met Ala Ala Ile Gly Val Ala Leu Trp Lys Tyr Val Met
        35                  40                  45

Lys Tyr Ser Pro Lys Asn Ala Asp Phe Phe Asn Arg Asp Arg Phe Val
    50                  55                  60

Leu Ser Asn Gly His Ala Cys Leu Phe Gln Tyr Thr Phe Leu His Leu
65                  70                  75                  80

Thr Gly Tyr Gln Ala Met Thr Phe Glu Gln Leu Ser Ser Tyr His Ser
                85                  90                  95

Glu Arg Trp Asp Ser Tyr Thr Pro Gly His Pro Glu Ile Glu His Glu
            100                 105                 110

Gly Ile Glu Val Thr Thr Gly Pro Leu Gly Gln Gly Ile Ala Asn Ala
        115                 120                 125

Val Gly Leu Ala Met Ala Thr Lys His Leu Gly Ala Val Tyr Asn Arg
130                 135                 140

Pro Gly Phe Glu Met Val Asn Asn Met Thr Trp Val Thr Ile Gly Asp
145                 150                 155                 160

Ala Cys Leu Gln Glu Gly Val Gly Met Glu Ala Ile Gln Leu Ala Gly
                165                 170                 175

His Trp Arg Leu Asp Asn Leu Cys Val Ile Tyr Asp Asn Asn Gln Ile
            180                 185                 190

Thr Cys Asp Gly Ser Val Asp Ile Cys Met Ala Glu Asp Val Asn Met
        195                 200                 205

Lys Met Arg Ala Ser Gly Phe Glu Val Leu Glu Val Glu Asp Gly Asn
210                 215                 220

His Asp Val Glu Ser Ile Val Lys Ala Leu Val Ala Ala Arg Ala Asn
225                 230                 235                 240

Lys Lys Arg Pro Thr Phe Ile Asn Ile Lys Thr Thr Ile Gly Val Gly
                245                 250                 255

Ser Lys Lys Gln Gly Ile Ala Asp Val His Gly Ala Pro Leu Gly Lys
            260                 265                 270

Glu Asp Val Ala His Ile Lys Glu Ser Phe Gly Leu Asp Ser Ser Lys
        275                 280                 285

Ile Leu Glu Val Pro Gln Glu Val Tyr Asp Phe Phe Arg Glu Ala Val
```

```
                  290                 295                 300
Pro Arg Gly Gln Gln Leu Glu Lys Asp Trp Asn Gly Leu Leu Ser Lys
305                 310                 315                 320

Tyr Ser Lys Glu His Pro Asp Leu Ala Ala Asp Leu Lys Lys Arg Met
                    325                 330                 335

Asn Gly Glu Met Leu Asp Asp Trp Thr Lys Tyr Ile Pro Lys Lys Glu
                340                 345                 350

Asp Phe Pro Thr Glu Pro Thr Pro Ser Arg Lys Ser Ala Gly Ala Val
            355                 360                 365

Cys Asn Pro Leu Ala Lys Asn Val Gly Asn Phe Met Val Gly Thr Ala
        370                 375                 380

Asp Leu Thr Pro Ser Val Asn Met Ala Trp Lys Gly Lys Val Asp Phe
385                 390                 395                 400

Gln His Pro Asp Leu Arg Thr Ala Cys Gly Ile Asn Gly Asp Tyr Thr
                    405                 410                 415

Gly Arg Tyr Leu His Trp Gly Ile Arg Glu His Ala Met Ala Ser Val
                420                 425                 430

Ser Asn Gly Met Ala Ala Phe Lys Lys Gly Cys Ile Leu Pro Val Thr
            435                 440                 445

Ser Ser Phe Phe Met Phe Tyr Ile Tyr Ala Ala Pro Gly Val Arg Met
        450                 455                 460

Gly Ala Leu Gln Ser Leu Gln Val Ile His Ile Ala Thr His Asp Ser
465                 470                 475                 480

Ile Gly Thr Gly Glu Asp Gly Pro Thr His Gln Pro Ile Glu Leu Ala
                    485                 490                 495

Ala Leu Tyr Arg Ala Met Pro Asn Phe Leu Tyr Ile Arg Pro Cys Asp
                500                 505                 510

Gly Glu Glu Ala Ala Gly Ala Phe Ile Ala Ala Val Gly Ala Lys Asn
            515                 520                 525

Thr Pro Ser Met Ile Ser Val Ala Arg Gln Asn Val Glu Gln Phe Pro
        530                 535                 540

Lys Tyr Ser Ser Arg Glu Gly Val Gln Lys Gly Ala Tyr Val Phe Ile
545                 550                 555                 560

Glu Glu Gln Asp Ala Asp Val Thr Leu Ile Gly Val Gly Ala Glu Met
                    565                 570                 575

Thr Phe Ala Val Gly Ala Ala Lys Val Leu Lys Asp Lys His Gly Ile
                580                 585                 590

Lys Ala Arg Ile Val Ser Phe Pro Ser Gln Arg Leu Phe Glu Glu Gln
            595                 600                 605

Pro Ile Glu Tyr Lys Arg Glu Val Leu Gln Tyr Arg Ser Asn Ala Pro
        610                 615                 620

Arg Val Ile Ile Glu Ala Tyr Thr Val Asn Gly Trp Glu Arg Tyr Ala
625                 630                 635                 640

Asp Ala Gly Tyr Ser Met His Thr Phe Gly His Ser Leu Pro Arg Gln
                    645                 650                 655

Tyr Val Tyr Gly Arg Phe Asn Phe Asp Asn Asp Lys Ile Ala Ala Lys
                660                 665                 670

Ile Gln Pro Leu Val Gln Glu Val Lys Lys Asn Gly Ile Glu Ser Leu
            675                 680                 685

Arg Gly Glu Phe Arg Asp Leu Asn Thr Asp Tyr Pro Arg Asp Val Phe
        690                 695                 700

His Ser Ala Phe Gly Thr Ser His Val Val Ser
705                 710                 715
```

<210> SEQ ID NO 32
<211> LENGTH: 730
<212> TYPE: PRT
<213> ORGANISM: Mycobacterium

<400> SEQUENCE: 32

```
Met Arg Pro Pro Glu Ala Asp Glu Pro Lys Gly Arg Asn Arg Asp Ser
1               5                   10                  15

Asp Ser Arg Cys Asp Pro Cys Arg Ala Gln Phe Asp Thr Val Gly Val
            20                  25                  30

Glu Leu Asp Asn Arg Gly Pro Ala Cys Arg Gly His Arg Pro Gly Ala
        35                  40                  45

Gly Arg Gly Cys Val Glu Lys Val Gly Asn Gly His Pro Gly Thr Ala
    50                  55                  60

Met Ser Leu Ala Pro Ala Ala Tyr Leu Leu Phe Gln Lys Leu Met Arg
65                  70                  75                  80

His Asp Pro Arg Asp Pro Asp Trp Val Gly Gly Asp Arg Phe Ile Leu
                85                  90                  95

Ser Pro Gly His Ser Ser Val Thr Leu Tyr Ile Gln Leu Phe Leu Ala
            100                 105                 110

Gly Tyr Gly Leu Glu Leu Glu Asp Leu Lys Ser Phe Arg Thr Trp Gly
        115                 120                 125

Ser Leu Thr Pro Gly His Pro Glu Tyr Lys His Thr Lys Gly Val Glu
    130                 135                 140

Ile Thr Thr Gly Pro Leu Gly Gln Gly Leu Ala Ser Ser Val Gly Phe
145                 150                 155                 160

Ala Tyr Ser Gln Arg Arg Met Arg Gly Leu Leu Asp Pro Asp Ala Ala
                165                 170                 175

Pro Gly Thr Ser Pro Phe Asp His Thr Ile Trp Val Ile Ala Ser Asp
            180                 185                 190

Gly Asp Leu Gln Glu Gly Val Thr Ser Glu Ala Ser Ser Leu Ala Gly
        195                 200                 205

His Gln Glu Leu Gly Asn Leu Val Val Val Tyr Asp Glu Asn His Ile
    210                 215                 220

Ser Ile Glu Asp Asp Thr Asp Ile Ser Phe Thr Glu Asp Val Leu Gly
225                 230                 235                 240

Arg Tyr Glu Ser Tyr Gly Trp His Val Gln Arg Val Asp Trp Thr Arg
                245                 250                 255

Thr Gly Glu Tyr Arg Glu Asp Val Glu Glu Leu Phe Ala Ala Leu Leu
            260                 265                 270

Ala Arg Arg Arg Lys Pro Arg Ser Arg Pro Ser Phe Val Arg Thr Ile
        275                 280                 285

Ile Gly Tyr Pro Ala Pro Lys Lys Gln Asn Thr Gly Lys Ile His Gly
    290                 295                 300

Ser Ala Leu Gly Ala Glu Val Ala Ala Val Lys Glu Val Leu Gly
305                 310                 315                 320

Phe Asp Pro Ala Lys Ser Phe Asp Val Asp Pro Ala Ile Leu Ala His
                325                 330                 335

Ala Arg Ala Ala Ile Asp Arg Gly Ala Ala Arg Ser Glu Trp Asp
            340                 345                 350

Glu Ser Phe Gln Ser Trp Gln Ala Ala Asn Pro Asp Ala Ala Ala Leu
        355                 360                 365

Leu Arg Arg Ile Glu Ala Arg Gln Leu Pro Asp Gly Val Asp Ala Val
```

Leu Pro Val Phe Glu Ala Gly Lys Asp Val Ser Thr Arg Ala Ala Ser
385                 390                 395                 400

Gly Lys Val Leu Asn Ala Leu Gly Pro Val Leu Pro Glu Leu Trp Gly
            405                 410                 415

Gly Ser Ala Asp Leu Ala Glu Ser Asn Thr Thr Ile Glu Gly Ser
            420                 425                 430

Pro Ser Phe Ile Pro Val Ser Arg Ser Ala Asn Ala Trp Lys Gly Asn
            435                 440                 445

Pro Tyr Gly Arg Val Leu His Phe Gly Ile Arg Glu Gln Leu Pro Arg
450                 455                 460

Ser Ile Val Asn Gly Ile Ser Leu His Gly Pro Thr Arg Ala Phe Ser
465                 470                 475                 480

Gly Thr Phe Leu Ile Phe Ser Asp Tyr Gln Arg Pro Ala Ile Arg Leu
            485                 490                 495

Ser Ala Leu Met Gly Val Pro Ser Val Tyr Val Trp Ser His Asp Ser
            500                 505                 510

Ile Gly Leu Gly Glu Asp Gly Pro Thr His Gln Pro Val Glu Gln Leu
            515                 520                 525

Ser Thr Leu Arg Ala Ile Pro Gly Leu Asp Val Val Gly Pro Gly Asp
530                 535                 540

Ala Asn Glu Val Gly Ile Ala Trp Lys Thr Ile Leu Glu Asn His Glu
545                 550                 555                 560

Asn Pro Ala Gly Val Val Leu Thr Arg Gln Asn Ile Pro Thr Phe Ala
            565                 570                 575

Arg Gly Glu Gly Ala Ala Glu Gly Asp Thr Phe Ala Ser Ala Ala Gly
            580                 585                 590

Val Ala Lys Gly Gly Tyr Val Leu Ala Glu Ala Ser Arg Asp Gly Ala
            595                 600                 605

Thr Val Pro Ala Gln Val Leu Leu Ile Ala Thr Gly Ser Glu Val Gln
610                 615                 620

Leu Ala Val Gln Ala Arg Glu Ala Leu Gln Ala Glu Gly Ile Pro Thr
625                 630                 635                 640

Arg Val Ile Ser Met Pro Cys Val Glu Trp Phe Asn Lys Gln Asp Ala
            645                 650                 655

Ala Tyr Arg Glu Ser Val Leu Pro Ala Ala Val Thr Ala Arg Val Ser
            660                 665                 670

Val Glu Ala Gly Leu Ala Leu Gly Trp Lys Glu Phe Val Gly Asp Ala
            675                 680                 685

Gly Arg Ser Val Ser Leu Glu His Phe Gly Ala Ser Ala Asp Tyr Lys
690                 695                 700

Arg Leu Phe Gln Glu Phe Gly Ile Thr Ala Asp Ala Val Val Ala Ala
705                 710                 715                 720

Ala Lys Asp Ser Ile Thr Ala Ala Gly Asn
            725                 730

<210> SEQ ID NO 33
<211> LENGTH: 1158
<212> TYPE: DNA
<213> ORGANISM: Bacillus methanolicus

<400> SEQUENCE: 33
atgacaaaca ctcaaagtgc attttttatg ccttcagtca atctatttgg tgcaggatca    60
gttaatgagg ttggaactcg attagctgat cttggtgtga aaaaagcttt attagttaca   120

```
gatgctggtc ttcacggttt aggtctttct gaaaaaattt ccagtattat tcgtgcagct      180
ggtgtggaag tatccatttt tccaaaagcc gaaccaaatc caaccgataa aaacgtcgca      240
gaaggtttag aagcgtataa cgctgaaaac tgtgacagca ttgtcactct gggcggcgga      300
agttcacatg atgccggaaa agccattgca ttagtagctg ctaatggtgg aaaaattcac      360
gattatgaag gtgtcgatgt atcaaaagaa ccaatggtcc cgctaattgc gattaataca      420
acagctggta caggcagtga attaactaaa ttcacaatca tcacagatac tgaacgcaaa      480
gtgaaaatgg ccattgtgga taaacatgta acacctacac tttcaatcaa cgacccagag      540
ctaatggttg gaatgcctcc gtccttaact gctgctactg gattagatgc attaactcat      600
gcaattgaag catatgtttc aactggtgct actccaatta cagatgcact tgcaattcag      660
gcgatcaaaa tcatttctaa atacttgccg cgtgcagttg caaatggaaa agacattgaa      720
gcacgtgaac aaatggcctt cgctcaatca ttagctggca tggcattcaa taacgcgggt      780
ttaggctatt tcatgcgat tgcacaccaa ttaggaggat tctacaactt ccctcatggc       840
gtttgcaatg cggtccttct gccatatgta tgtcgattta acttaatttc taaagtggaa      900
cgttatgcag aaatcgctgc ttttcttggt gaaaatgtcg acggtctaag tacgtacgat      960
gcagctgaaa aagctattaa agcgatcgaa agaatggcta aagaccttaa cattccaaaa     1020
ggctttaaag aactaggtgc taagaagaa gacattgaga ctttagctaa gaatgcgatg      1080
aaagatgcat gtgcattaac aaatcctcgt aaacctaagt tagaagaagt catccaaatt     1140
attaaaaatg cgatgtaa                                                    1158
```

<210> SEQ ID NO 34
<211> LENGTH: 1161
<212> TYPE: DNA
<213> ORGANISM: Bacillus coagulans

<400> SEQUENCE: 34

```
atgttaacag gattacgtac tgattttcaa atgccttccg taaacttgtt tggacagggg       60
acggcagaag aaattggaaa caggctgaaa atcttgggt gtcgcagacc gctgattgta      120
accgatgaag ggctccacca actggggtat tccgaaaaaa ttgcagccta tataaaagaa      180
gccggcctgg aagtgcgat ctatccgaag gctgaaccaa atccgacaga caaaaatgtg      240
gaagacgggt taaaaaccta tcatgaagaa aattgcgatt caatcgtttc acttggcggc      300
gggagcgcgc atgactgtgc aaaagggatc gggctcgttg cggccaatgg gggcaaaatc      360
catgattatg aagggctgga ccgttctgaa aaaccaatgg tgccgctcgt tgcaattaat      420
acaacagccg ggactgccag cgaaatgaca aaatttacga ttattaccga tacgagtcgg      480
aaagtgaaaa tggcgattgt agataaacat gtgacaccgg ttttgtccat taatgatcca      540
ttattaatgg tcgggatgcc gccgtctta actgcggcaa cggggcttga cgctttgacc      600
catgcagtga agcgtatgt ttcaactgcg gccacaccgg taacagatgc atgcgccatt      660
aaagcgatcc aaattattcc gcaatatttg ccaaaggctg ttgcaaacgg caatgatatg      720
gaagcgcgtg aacaaatggt atatgcgcag tatttggcag gcatggcgtt taataatgca      780
tctttgggct atgtccacgc gattgcgcac cagttcggcg gtttctataa cttgccgcac      840 ggcgttgtgca atgcgatttt gctcccgcat gtgtgccgtt tcaatctgat tgcgcggaaa      900
gaaagatttg cagaaattgc cgttgcactg ggtgagaaga cggatggcct gagcgtcgac      960
gaagcggcgg aaaaagccat tacagcaatt gaaaggctgg cagcacagct gaacattccg     1020
```

```
aaaggctttta aagaactcgg ggctaaagaa gaagatatcg aaatcctcgc ccagcatgcg    1080
atgcaggacg cgtgcgcagc cacaaacccg cgcaaaccaa cacaaaaaga agtggaagcg    1140
attataaaag cagcgatgta a                                              1161
```

<210> SEQ ID NO 35
<211> LENGTH: 1173
<212> TYPE: DNA
<213> ORGANISM: Burkholderia

<400> SEQUENCE: 35

```
atgagctacc tgaacatcgc tgagcgcact gacagctttt tcatgccctg cgtcaccctc      60
atcggcccag gctgcgcgcg ggaaaccgga acgcgcgcca atcgctcgg cgcgaaaaaa      120 gtcctgatcg tcactgacgc gggcctgcac aagatggggt tgtcggaaat catcgcgggc     180
tacctgcgcg aagccggcct tcaagcgacg atcttcgcgg gcgccgaacc caatccgacc    240
gatctcaacg ttcacgacgg cgtcgcgctg ttcgagcagc acgggtgcga tttcatcgtg    300
tcgctcggcg gcggctcgtc tcacgactgc gcaaaaggca tcgggctcgt aagcgccggc    360
ggcggccata tccgcgatta cgagggcatc gaccgctcca gcgtgccgat gacgccgctg    420
atttcgatca atacgacggc cggcaccgcg gcggagatga cgcgcttttg catcatcacg    480
aattccagca accacgtgaa gatggccatt gtcgactggc gctccacgcc gctcgtcgca    540
atcgacgatc cgcgcctgat ggtgcgatg ccgccggcgt tgaccgccgc gaccggcatg    600
gacgcgttga cgcatgcggt ggaagcctac gtgtccaccg cggcgacgcc gatcaccgac    660
gcctgtgccg aaaaggcgat cgcgctgatc ggccagtggc tgccgaaggc tgtcgcgaac    720
ggcgaatcga tggaggcacg cgcggcgatg tgctacgcgc aatatctcgc cggcatggcg    780
ttcaacaatg cgtcgctcgg ctatgtgcat gcgatggcgc atcagctcgg cggcttctac    840
aacttaccgc atggcgtgtg caatgcgatc ttgctgccgc acgtgtgcga gttcaatctc    900
atcgccgcgc ccgagcgctt tgccgccatc gcttcgctgc tcggcgcgag cacgccgggg    960
ttgagcacca ccgaagctgc ccgggccgct atcgcggcca tccggagcct gtccgcgtcg    1020
atcggcattc cgtcgggcct ggccggcctc ggcgtcaaag ccgacgatca cgaagtgatg    1080
gcgcacaacg cgcagaagga tgcttgcatg ctgacgaatc cgcgcaaggc aagcgtggcc    1140
caggtcatcg ctattttcga agcggccatg taa                                1173
```

<210> SEQ ID NO 36
<211> LENGTH: 1173
<212> TYPE: DNA
<213> ORGANISM: Acinetobacter gerneri

<400> SEQUENCE: 36

```
atggctttta aaaatcttgc agaccaaaca aatggcttttt atatcccttg cgtatcgctt    60
ttcggtcctg gttgtgccaa agaagttggc gcgaaagcac agaatttagg tgcaaaaaaa    120
gcattaatcg taacagatgc tggcttatttt aaatttgggg ttgctgacat tattgttggt    180
tatttaaaag atgctggcgt tgacagtcac gtgttccctg gtgctgaacc aaacccgact    240
gatatcaacg tattaaatgg cgtgcaagca tataacgata tggttgtga ttttatcgtt    300 tcacttggtg gtggttcatc acatgactgc gctaaaggta ttggtttagt gactgctggt    360
ggcggtaata tccgtgacta cgaaggcatt gacaagagtt ctgtaccaat gactccgctt    420
attgcgatca atacaactgc gggtactgct tcagaaatga cacgtttctg tatcattacc    480
aatacagata cacacgttaa aatggcgatt gtagactggc gttgtactcc gcttgtagcg    540
```

```
attgatgatc ctaaactgat gattgcaaag cctgcagcat taaccgcagc tacaggtatg      600
gatgcattga ctcacgcagt tgaagcttat gtttctacag cagcaaaccc gattaccgat      660
gcatgtgctg aaaaagcaat tagcatgatc agtgaatggt taagctctgc agttgcaaat      720
ggcgaaaaca tcgaagctcg tgatgcaatg gcttatgcac aatatcttgc aggtatggca      780
tttaacaacg catctctcgg ctatgttcat gcaatggcac accaattagg tggtttctat      840
aacttgccac acggcgtttg taatgcaatc ttacttccgc acgtatgtga gtttaacctc      900
atcgcatgtc cagatcgctt tgcaaaaatt gctcaactca tgggtgttga cacaacaggc      960
atgacagtaa ctgaagcagg ctacgaagca attgctgcaa tccgtgaatt atctgcgtct     1020
atcggtatcc cttcaggttt aactgagctt ggtgtgaaag cagctgatca tgctgtaatg     1080
acatcgaatg cacaaaaaga tgcttgtatg ttgactaacc cacgtaaagc aacagatgca     1140
caagtgattg cgattttga agctgcaatg taa                                   1173

<210> SEQ ID NO 37
<211> LENGTH: 1170
<212> TYPE: DNA
<213> ORGANISM: Herbaspirillum rubrisubalbicans

<400> SEQUENCE: 37
atggcaatgg caaatcagac ctttggcttc tacatgccaa cgtatcgct catgggcgtg        60
ggttgcgccg aggaagtcgg cctgcaagcc aaggcattgg gagcacgacg cgtgttcctg      120
tgtaccgacg tcggcatggt caagctcggc atggcgaaca agatcaaggc catcctcgag      180
agcgcggact tggccgtcac cgtctatgac ggttccgatc cgaatccgac tgacaagaac      240
gtagaactgg gggtgcagct ataccgcgcc gccgattgcg atgctatcgt ctcgctcggc      300
ggcggcagtg cccacgactg tgccaagggc atcggcatgg tggtcagcaa cggtggcaat      360
atccgtgact acgaaggtct gaacaagacc agcaagccca tgccgccctt cctggccatc      420
aacaccacgg ccggcacggc cagtgagatg accgttttt gcatcatcac caataccgac      480
aaccacgtga agatggccct ggtggactgg cgctgcacgc caatgtggc catcaacgat      540
ccgctgctga tgaaggacat gccggcctcc ctcaccgctg ccaccggcat ggacgccctc      600
acccacgcca tcgaagccta cgtttccacg gccgccacgc cgattaccga tgcgtgcgcc      660
ctgcaggcga tccgcctcat ctcgcaatgg ctgcgtccgg ccgtgccaa tgcccagcag      720
atggaagccc gtgacaagat ggcctatgcc gaatacctgg ccggcatggc gttcaataac      780
gcctcgctcg gctacgtcca cgcgatggcc caccaactgg tggtttccta caacctgccc      840
catggcgtgt gcaacgccat cctgctgccc gaggtgtgca gcttcaacct catcgcctgc      900
ccacaacgct acgccgacat cgccgaggcg atgggtgaaa agatcgccaa cctgtcggtg      960
atggatgccg ccgacaaggc catcaaggcg atccggcaac tggcccgcga cgtcgccatc     1020
ccgcccaatc tggcggtact gggtgtcaag gagagcgact cgagctgat ggccaccaat     1080
gccaagaaag acgcctgcca gctcaccaac ccgcgcacgg cgacgctgga acaggtggtg     1140
ggcatcttcc gtcaagccca tcagggctga                                     1170

<210> SEQ ID NO 38
<211> LENGTH: 1149
<212> TYPE: DNA
<213> ORGANISM: Wohlfahrtiimonas chitiniclastica

<400> SEQUENCE: 38
```

| | |
|---|---:|
| atggccacac aattcttaat gccttctaaa aacattatgg gtgcaggtgc actcgatctc | 60 |
| gcgtatgacg acattaaagc ccaaggcttt aaaaaaatct taatcgtgag tgatgaaggc | 120 |
| ttaaaaggcg caggtatcat tgacttagtt gtaaaaggtt tgaaagataa aggcattgaa | 180 |
| tctgccgttt actcaggcac taagccaaac ccaaccacaa aaaacgtgga agagggtttg | 240 |
| gcaattttaa aagcagaaca ttgtgatgcc atcatctctt taggtggcgg ttctccgcat | 300 |
| gactgtgcta aaggcattgc tttagtggca gcgaatggcg gtaaaatcaa cgattatgaa | 360 |
| ggcatcaata aatcagcaaa acctcagttg ccattgattg ccattaacac aactgcgggt | 420 |
| accgcttctg aaatgaccta tttctgtatc attacagatg aatcacgcca cattaaaatg | 480 |
| gcgattgtag atgcgcacac cacaccatta ttatccgtga atgatcctga attgatgaaa | 540 |
| ggcatgccaa atcattaac agctgccaca gggatggatg cattgacgca tgcggttgaa | 600 |
| gcttatgtat caacggccgc aacaccgatc acagatgcat gtgccgttaa agcggtggcg | 660 |
| ctcattcata aaaatttacg cgatgcggtg aatgatggcg caaatatgca tgcccgtgaa | 720 |
| caaatggcgt acgcacaatt tttagcaggg atggcattta acaacgcatc tttaggttat | 780 |
| gtgcatgcaa tggcgcatca actgggcggt ttttatgact taccacatgg cgtatgtaac | 840 |
| gcagtcttat tgccacatgt acaagaatac aatgcgaaag tggcggcagg cgcttaaaa | 900 |
| gatttagccg catgctttga catcgacact cgtgcgatga gtgatgaaga aggtgcaaaa | 960 |
| gcgttaattg cagcgattcg tacattaagt caagatgtgg gcattcctgc aggcttaaaa | 1020 |
| gatttaggtg cgaaagaaga agatttcaca atcttggcag aaaatgcatt gaaagatgct | 1080 |
| tgctccttca cgaacccacg taaaggcgat gaagcagaag tgatcgcaat tttcaaagcg | 1140 |
| gcattctaa | 1149 |

<210> SEQ ID NO 39
<211> LENGTH: 1149
<212> TYPE: DNA
<213> ORGANISM: Pseudomonas lini

<400> SEQUENCE: 39

| | |
|---|---:|
| atgagcagta cgttcttcat tcccgctgtg aacatcatgg gcaccggttg ccttgacgaa | 60 |
| gccatggacg ccattcgcaa gtatggttttt cgcaaggcgc tgatcgtcac cgacaccggg | 120 |
| ctggccaagg ctggcgtggc gacgatgatt gccggaaaac tggcgttgca ggacatcgac | 180 |
| tcggtgatct tcgacggtgc caagccgaat ccaagcatcg ccaacgtcga gctaggcctg | 240 |
| ggtctgctca aggaaagtcg ctgtgatttc gtggtgtcgc tgggcggcgg ttcgcctcac | 300 |
| gactgcgcca agggcatcgc gttgtgcgcc acaaacggtg ggacgattcg tgactacgaa | 360 |
| ggtgtcgatc agtcggccaa accgcaaatg ccgttgatcg cgatcaacac caccgccggt | 420 |
| accgccagcg agatgacccg ttttttgcatc atcaccgacg agtcccgtca cgtgaaaatg | 480 |
| gccatcgtcg atcgcaacgt cacaccgctg ctgtcagtca cgatccggc gctgatggtc | 540 |
| gccatgccca agggcctgac tgccgccact ggcatggacg cactgaccca cgccatcgaa | 600 |
| gcctacgtct ccaccgcggc caacccgatt accgatgcct gtgcgctgaa agccatcacc | 660 |
| ttgatcagca ataacctgcg cctggctgta cgcgacggca gtgacatgat cgcgcgggaa | 720 |
| aacatggctt acgcgcagtt cctcgctggt atggcgttca acaatgcgtc cttgggatat | 780 |
| gtccacgcca tggcccacca gttgggcggg ttctacgact tgcccatgg tgtgtgcaat | 840 |
| gcggtgctac tgcctcatgt gcaaagtttc aacgcgctgg tctgcgccga ccgcctgacc | 900 |
| gatgttgccc gcgcgatggg cgccgacatt cgcgggttca gccccggaaga gggcgctcag | 960 |

```
gcagccatcg cggccattcg caacctggcc aaggacgtgg aaattcccgc cggtttacgt    1020
gagctcggta ccaagctcac cgacatcccg gttctcgcca gcaatgccat gaaagacgcc    1080
tgtggactga ccaatccacg gaaggcggat cagcggcaga tcgaggagat tttccgcagc    1140
gcgttttaa                                                             1149

<210> SEQ ID NO 40
<211> LENGTH: 1155
<212> TYPE: DNA
<213> ORGANISM: Paenibacillus

<400> SEQUENCE: 40
atgacgggaa cttccaaatt catgatgccg ggtatgagtc ttatgggctc aggcgcactg      60
gcggatgcag gtacagaaat cggaaaattg ggctttaaaa atgcattgat cgtaaccgat    120
aagcctttag ttgatattgg gattgtggaa aaagtaacaa ccatgctgga agtcataaac    180
gtaaaatccg tcgtatacag cggcacacag ccgaatccca cggtttccaa tgtcaacgag    240
ggcttggcgc tgctgaaaca atccgggtgt gattttatta tttcgctcgg aggcgggtca    300
ccgcatgact gtgccaaggg aatcgctctt ttggcctcca acggcggaca gatcggcgac    360
tacgaaggcg tggataaatc cgggaagcct tccttcccac tgattgccat taacactacg    420
gcaggaacag ctagtgaaat gactatgttt tgtattatta cggatgaaga gcgtcatatc    480
aaaatggcga ttgtcgacaa gcacacgaca ccactcattg ccgtcaatga tcctgatcta    540
atgatggcta tgcccaaatc attaactgcc gcaacgggga tggatgcgct cactcactct    600
attgaagctt atgtttccac aaatgccaca ccgatcacag atgcttgcgc gcttaaagca    660
attgagctga ttcgggatca tctggtcaaa gccgtcgatg acggaaatga tgtggaagcc    720
cgtagccaaa tggcctacgc cgagttcctc gcagggatgg cgttcaataa cgccggatta    780
ggctttgttc acgccatggc gcatcaactg ggtggcttct ataatctgcc gcacggggtc    840
tgtaacgcca ttttgctgcc gcatgtagag cgctataatg ccaaggcttc cgccgaacga    900
ctcaccgaca ttgcccgtac acttggcgaa aaaacggacg tgttacaccg gaacaaggt     960 gccaacctcg ccctgcacgc tatcgaaaag ctggctaaac gggtcaacat cccttccggg   1020
ctggaagaac tcggcgtcaa acgcgaagat ttcgctgttc tcgccgctaa cgcactcaaa   1080
gatgcctgcg gtgcaacgaa tccgattcag cctacgcaac aagaagtgat cgacattttt   1140
gaacaggcga tgtaa                                                      1155

<210> SEQ ID NO 41
<211> LENGTH: 1149
<212> TYPE: DNA
<213> ORGANISM: Photobacterium damselae

<400> SEQUENCE: 41
atgagcagtg cattctatat tcctactgtt aactttatgg gcgcaggctg tttgactcaa     60
gcggctgatg cgattaaatc tcacggcttt aaaaaagcac tcattgttac cgataaagta    120
ttgaaccaaa ttggtgtggt tactcaagtt gctgtattgc tcactgagcg tgatattgac    180
tctgtggttt acgacggcac tcaaccaaac ccaaccatta aaacgttga tgaaggttta     240 gcgttactaa agaaaaccaa atgtgatttt gtgatttcat gggtggtgg ttctccacac     300 gactgcgcga aagtattgc gctattggct gccaacggtg gccacattgg tgattacgaa    360
ggtgttgacc gttctgcaaa agcacagcta cctgtggttg ctattaatac cactgctggt    420
```

```
accgcttctg agatgacacg tttctgtatc atcactgatg aagaacgtca tattaagatg    480
gcgattgtcg ataaaaatac gaccccatta atatctgtaa atgatcctca gttaatgttg    540
gcaaaacctg catcattaac cgctgcaaca ggtatggatg cattaactca cgctatcgaa    600
gcgtatgttt caacagccgc aacaccaatt actgatgcag tggcaattaa agcgattgag    660
ttaattcaac aaaacctacg taccgcagtg aaagatggtc aaaaccttaa tgctcgtgag    720
caaatggcgt atgcacagtt catggctggt atggctttta caacgcgtc actcggttat     780 gtacatgcga tggcgcacca gttaggcggt tactacaatc ttcctcatgg tgtatgtaat    840
gcggttttac tgccacatgt tcagcgttat aacgcgcaag tatcagctga gcgtttacgt    900
gatgttgcta aagcaatggg tgttgatgtt gaaggtatga cagcagagca gggcgctaat    960
gcagcacttg aagcgattgt cgcgctatct aaagatgttg gcattccact tggtttaaaa    1020
gaacttggtg tgaaagaaga agatatcgca ttacttgctg ataatgcatt gaaagatgct    1080
tgtggtttca ctaaccctaa acaagcaacc catgaagaaa tttcacagat ctttatggct    1140
gcaatgtaa                                                           1149

<210> SEQ ID NO 42
<211> LENGTH: 1149
<212> TYPE: DNA
<213> ORGANISM: Vibrio

<400> SEQUENCE: 42
atgtctaacg ctttctatat tccatcatta aacctaatgg gtgtcggctg tcttgaagaa     60
gcggtaaacg ctatcaaatc acatggcttt actaaagctc ttatcgttac cgacaaggtt    120
ttaaacgagc tgggcgcagt aagtaaactc actagtttgc ttgatagtgc aaacgtagca    180
gcggttgtgt tttacgagac taaaccaaac ccaactatcg agaacgtgaa cgatggctta    240
gcgctactaa aaggcaatca gtgtgattgt gtgatttcat tcggtggcgg ctcccctcat    300
gattgcgcaa aaggtatcgc attgcttgcg actaacggcg gagaaatcaa agactacgaa    360
ggtgttgatg tatcagcgaa gcctcagtta ccgctgatct caatcaatac aacggcaggc    420
actgcttctg aaatgacacg tttctgcatc atcacagatg aggctcgcca catcaaaatg    480
gcaattgtag acaagaatgt gacgccaatt atctctgtaa acgaccctga gttgatgctg    540
gctaagcccg cgtctcttac agcggcaact gggatggacg cacttacgca cgcgattgaa    600
gcttatgtgt ctatcgcagc tacaccagtc acggatgccg ttgcgatcaa agctatcgaa    660
atggtgcaag caaaccttcg tgaggcggtg caaaacggtg acaatctaac tgcacgtgac    720
aacatggctt atgcgcagtt tatggcaggt atggcgttta caatgcttc actgggctat     780 gttcacgcta tcgctcacca acttggtggc ttctacgatc ttcctcatgg tgtatgtaac    840
gcaatcttgc taccacacgt tcagcaatat aacgctaagg tagtacctgc acgcctagct    900
gacgtcgcgc gcgccatggg tgttgatact aatggcatga ctgatgagca agccgcgaat    960
gctggtcttg atgctattcg tcagctatct aaagatgtga acattccggc tggtcttgaa    1020
cagcttggtg taaagcgcga cgacttcgat gtacttgcag agaacgcgct aaaagacgct    1080
tgtggtttca ccaaccctaa acaagcaagc cacgaagaaa tcgtagccat cttagattca    1140
gcgctgtaa                                                           1149

<210> SEQ ID NO 43
<211> LENGTH: 1149
<212> TYPE: DNA
<213> ORGANISM: Vibrio
```

<400> SEQUENCE: 43

```
atgagcagtt ctattatcct tccctctacc aatttattag gcagtgggtg tttatctcaa        60
gccgtagata ccattcacca acaaggcttt agcaaagcgc tgatagtgac ggatgccgtt       120
ttaactcaaa ttggcctcgt agcaacgatt actgagcaac ttgccgccaa aggcatgtct       180
tttgctattt acgatggaac acagcctaac cctaccatcg acaatgtaga acaaggtctc       240
tctacgttag tagacaatga ttgtgatctt attatctctg ttggtggtgg ctcacctcat       300
gactgtgcaa aaggcatcgc cttagtcgca actaatggcg aaaaatcac cgactatgaa        360
gggatcaaca aagcgagtaa atcacccttc cccttagttg cgattaatac acagctggc        420
accgcttctg agatgacgat gttcagcgtc atcacggacg aaagcagaca atcaaaatg        480
gcgatcgttg accaaaaggt aaccccattg atttcagtca acgaccctca gttaatgctt       540
gccatgccga gctcactgag tgctgcaaca ggcatggatg cacttactca tgctattgaa       600
gcttatgtct cagttgccgc gaacccgatc acagacacgg ttgcattaaa agcaattgag       660
ctaattacta aacatttgcc aacgtgtgtc agcaacggaa gtaacctcga agctcgggag       720
caaatggctt acgctcagtt tatggcaggt atggcattta acaacgcgct tcttggctac       780
gtacatgcga tggctcatca gttaggcgca acttatcacc ttccacatgg tatttgtaat       840
gctgtactcc ttcctcatgt acaacgtttt aatctcacgg ctaaccctga aaaattcgtc       900
gatattgcac aagcaatggg caaagaggtt catggattaa caacagaaga agcttctcag       960
ctggcaattg aagcgatgaa tgagcttgca agaaaggtaa acattcctgc gacgttagca      1020
gaattaggtg ttaaccaagg tgatattgat aaactatcag aaagtacact gaatgatgtt      1080
tgctgtttaa ccaatcctcg tcaggcaact aaacaagaaa tcgcggaaat attccaagcg      1140
gcttggtag                                                             1149
```

<210> SEQ ID NO 44
<211> LENGTH: 1149
<212> TYPE: DNA
<213> ORGANISM: Virgibacillus pantothenticus

<400> SEQUENCE: 44

```
atgtcaaagg ttttatatgt accaagtatt aatttaatag gtagaggctg cttagctgaa        60
gttggaccat ttattgaaga gttagggttt aagaaagcct tattagtaac agacaaattt       120
ttaaatgaaa gtggaattgc tcaagggta ttagatcaat tagacaaaat tggtgttttcc       180
tatgttgttt atgatgaagt aaagccaaat ccaacaacta aaaatgttca tgatggggtg       240
gaagtgttta agaataacaa ttgtgatttt ataatttctg ttggtggtgg atcacctcaa       300
gatgccgcca aaggaatagg actagttgta acaaatggtg acatgtgcg tgattatgaa        360
ggagtcggaa agacaaaata taaagcggtt ccaacaattg cagtgaatac aactgcgggt       420
acttctgctg aatacacgat taattatgtt attactgacg aagatcgaga gtaaagatg        480
gttatggtag ataaaaatag cttggttact attacagtga atgaccctga attaatgatg       540
ggaaaaccaa aagaccttac tgctgctaca ggaatggatg cgttaacaca tgctatggaa       600
gctattgtta ctcctggtgc atatccaatt acagatgcaa cagcactggc tgcagtagaa       660
ataatctttg aatacttacc gcgcgcagta aaagattcca ctgatattga agctcgagag       720
caaatggttt atgttatgtt tttagctggt gtcgcattta ataatgctgg attagggtat       780
gtgcatgcaa tggcgcatca acttggaggt gtttatgatc tgcctcatgg ggtgtgtaat       840
```

| | |
|---|---|
| gcgatgcttt taccaattgt agagcgagaa aatgctaaaa gagatcctag taagtttcgt | 900 |
| gcaattgcaa aggctgcagg tattgatatt acagataaaa cagatgaaca gtgtgcaagt | 960 |
| gcagtgatta aagcgattaa gaaattgtct aatgaagttg gtatcccaag caagctttca | 1020 |
| gaactgggtg ttaaagaagt agatcttgaa aaattagcca ataatgctat gaaggatgct | 1080 |
| tgtgcacctg gaaatccatt tcaaccaact aaagatgaag ttatctccat gtttaaagaa | 1140 |
| atattgtga | 1149 |

<210> SEQ ID NO 45
<211> LENGTH: 1020
<212> TYPE: DNA
<213> ORGANISM: Bacillus stearothermophilus

<400> SEQUENCE: 45

| | |
|---|---|
| atgaaagcag cggttgtcaa tgaatttaag aaagccctgg aaatcaaaga gtggaacgc | 60 |
| ccgaaactgg aagaaggtga agtcctggtg aaaattgaag cgtgcggcgt ttgtcatacc | 120 |
| gatctgcatg cggcccacgg tgactggccg attaaaccga aactgccgct gatcccgggt | 180 |
| cacgaaggcg tgggtatcgt ggttgaagtg gccaaaggtg ttaaatcaat taaagtcggc | 240 |
| gatcgtgtgg gtatcccgtg gctgtattcg gcatgcggcg aatgtgaata ctgcctgacc | 300 |
| ggtcaggaaa cgctgtgtcc gcatcaactg aacggcggtt attccgttga tggcggttat | 360 |
| gcagaatact gcaaagcacc ggctgattac gtggctaaaa ttccggataa tctgacccg | 420 |
| gttgaagtcg caccgatcct gtgtgctggc gtcaccacgt ataaagcact gaaagtgagc | 480 |
| ggtgcacgtc cgggtgaatg ggttgcgatt tatggcatcg gcggtctggg tcacattgcc | 540 |
| ctgcagtacg cgaaagccat gggtctgaac gtcgtggcag tggatatcag cgacgaaaaa | 600 |
| tctaaactgg ctaagatct gggcgcagac attgctatca atggtctgaa agaagatccg | 660 |
| gttaaagcga ttcatgacca agttggcggt gtccacgcag ctatcagcgt ggccgttaac | 720 |
| aagaaagcgt tgaacaggc ctaccaatct gtgaaacgtg gcggtacccct ggttgtcgtg | 780 |
| ggtctgccga acgcagatct gccgattccg atctttgaca ccgttctgaa tggtgtcagt | 840 |
| gtgaaaggct ccattgtcgg tacgcgcaaa gatatgcagg aagcactgga cttcgcggcc | 900 |
| cgtggcaaag ttcgcccgat tgtcgaaacg gcggaactgg aagaaatcaa tgaagtgttt | 960 |
| gaacgtatgg aaaaaggtaa atcaacggt cgtatcgtgc tgaaactgaa agaagattaa | 1020 |

<210> SEQ ID NO 46
<211> LENGTH: 1995
<212> TYPE: DNA
<213> ORGANISM: Pichia angusta

<400> SEQUENCE: 46

| | |
|---|---|
| atggccattc ctgacgaatt cgatatcatt gttgttggtg gaggttccac cggctgctgc | 60 |
| attgcgggca gactcgcaaa cctcgacgac caaaacctca cagttgccct gatcgagggt | 120 |
| ggtgagaaca acatcaacaa cccttgggtc taccttcccg gagtgtatcc tagaaacatg | 180 |
| agactcgact ccaagacggc caccttctac tcgtccagac catcgaaggc tctgaacggc | 240 |
| agaagagcga tcgttccttg cgccaacatc cttggaggcg ctcgtcgat caactttctg | 300 |
| atgtacacca gagcctctgc ttccgactac gacgactggg agtccgaggg atggagcacc | 360 |
| gacgagttgc tacctctgat caaaaaaatc gaaacttacc agcgtccttg caacaacaga | 420 |
| gatctgcacg gctttgacgg cccaatcaag gtttcctttg gaaactacac gtatcctacg | 480 |
| tgccaggact tcctgagagc agcagagtcg cagggaattc ctgttgtgga cgacctggag | 540 |

```
gacttcaaga catcgcatgg tgcagagcac tggctgaagt ggattaacag agacctgggc    600
agaagatcgg attctgcgca cgcctacgtc cacccaacta tgagaaacaa gcagagcctg    660
ttcctcatca cctccaccaa gtgtgacaag gtgatcatcg aggacggcaa ggctgtggcc    720
gtgagaacag tgccaatgaa gcctctgaac cctaagaagc tgtgtccag aaccttcaga     780 gccagaaagc agattgtgat ctcctgcgga accatctcgt ctcctctggt gctccagaga    840
tctggtattg tgcagctca ccacttgaga tccgtggggg tcaagccaat cgtcgacctg     900
ccaggtgtgg gtgagaattt ccaggaccac tactgtttct tcactccata ctacgtcaag    960
cctgacgttc ctacgttcga cgactttgtc aggggcgacc cagttgccca gaaggccgct   1020
ttcgaccagt ggtactccaa caaggacggt ccattgacca ccaacggtat tgaagccgga   1080
gtcaagatca gacctaccga gaggagctg gctaccgcgg acgaggactt cagacgcggc    1140
tacgcagagt acttcgagaa caagccagac aagcctctga tgcactactc tgtcatctcc   1200
ggcttctttg gagaccacac caagattcct aacggcaagt tcatgaccat gttccacttc   1260
ctggagtatc cattctccag aggatttgtt agaatcacct cggcaaaccc atacgacgct   1320
cctgacttcg atcccggctt cctcaatgac gaaagagacc tgtggcctat ggtctgggca   1380
tacaagaagt ccagagagac ggccagaaga atggagagct ttgcaggaga ggtcacctcg   1440
caccacccat tgttcaaggt tgactcgcca gccagagcca gagacctgga cctcgagaca   1500
tgcagtgcat atgccggtcc taagcacctc actgccaacc tgtaccacgg ctcgtggacc   1560
gttcctatcg acaagccaac gcctaagaac gatttccacg tgacctccaa ccaagtccaa   1620
ctgcactccg acatcgagta caccgaggag gacgacgagg ccatcgtcaa ctacattaag   1680
gaacacaccg agaccacttg gcactgtctg ggtacctgct cgatggcccc aagagagggt   1740
agtaagattg ctcctaaggg aggtgtcttg gacgccagac tgaacgttta cggagtccag   1800
aacctcaagg ttgcggacct ttctgttttgt cccgacaacg ttggatgcaa cacctactct   1860
actgcattga ccatcggtga aaggctgcc actcttgttg ctgaagatct tggctactca    1920
ggctccgacc tggacatgac gattccaaac ttcagactcg gaacttacga ggagaccgga   1980
cttgccagat tctaa                                                    1995

<210> SEQ ID NO 47
<211> LENGTH: 2133
<212> TYPE: DNA
<213> ORGANISM: Pichia angusta

<400> SEQUENCE: 47
atgagtatga gaatccctaa gcagcgtcg gtcaacgacg acaacacca gagaatcatc      60 aagtacggtc gtgctcttgt cctggacatt gtcgagcagt acgaggagg ccacccgggc    120 tcggccatgg gcgccatggc tatcggaatt gctctgtgga atacaccct gaaatatgct    180 cccaacgacc ctaactactt caacagagac aggtttgtcc tgtcgaacgg tcacgtgtgt   240
ctgttccagt atatcttcca gcacctgtac ggtctcaagt cgatgaccat ggcgcagctg    300
aagtcctacc actcgaatga cttccactcg ctgtgtcccg gtcacccaga atcgagcac    360 gacgccgtcg aggtcacaac gggcccgctc ggccagggta tctcgaactc tgttggtctg    420
gccatagcca ccaaaaacct ggctgccacg tacaacaagc cgggctttga tatcatcacc    480
aacaaggtgt actgcatggt tggcgatgcg tgcttgcagg agggccctgc tctcgagtcg    540
atctcgctgg ccggccacat ggggctggac aatctgattg tgctctacga caacaaccag   600
```

```
gtctgctgtg acggcagtgt tgacattgcc aacacggagg acatcagtgc caagttcaag      660
gcctgcaact ggaacgtgat cgaggtcgag aacgcttccg aggacgtggc taccattgtc      720
aaggccttgg agtacgcgca ggccgagaag cacagaccaa cacttatcaa ctgcagaact      780
gtgattggat cgggtgctgc gttcgagaac cactgtgctg cgcacggtaa cgctctgggc      840
gaggacggtg tgcgcgagct caaaatcaag tacggcatga acccggccca gaagttctac      900
attccgcagg acgtgtacga cttcttcaag gagaagccgg ccgagggcga caagctggtg      960
gccgaatgga gagtctcgt ggccaagtac gtcaaggcgt accctgagga gggccaggag     1020
ttttttggcgc ggatgagagg cgagctgcca agaactggaa agtcgttcct gccgcagcag     1080
gaattcaccg gcgacgctcc tacaagggcc gctgccagag agcttgtgag agccctgggg     1140
cagaactgca agtcggtgat tgccggttgc gcagacctgt ctgtgtctgt caatttgcag     1200
tggccagggg tgaaatattt catggacccc tcgctgtcca cgcagtgtgg cctgagcggc     1260
gactactccg gcagatacat tgagtacgga atcagagaac acgccatgtg tgctatcgcc     1320
aatggccttg ccgcctacaa caagggcacg ttcctgccga tcacgtcgac tttcttcatg     1380
ttctacctgt acgctgcccc agccatcaga tggccggcc tgcaggagct caaggcgatc     1440
cacatcggca cccacgactc gatcaatgag ggtgagaacg ccctacgca ccagccggtc     1500
gagtcgccag cattgttccg ggccatgcca acatttact acatgagacc ggtcgactct     1560
gcagaagtgt ttggcctgtt ccaaaaagcc gtcgagctgc cattcagctc gattctgtcg     1620
ctctcgagaa cgaggtgct gcaatacccct ggcaagtcga gcgcagagaa ggcgcaacgc     1680
ggcggctata ttctggagga tgcggagaac gccgaggtgc agattattgg agttggtgca     1740
gagatggagt ttgcatacaa ggccgccaag atcttgggca gaaagttcag gaccagagtt     1800
ctctccatcc catgcacgcg gctgtttgac gagcagtcga tcggctatag acgctcggtt     1860
ttgagaaagg acggcagaca ggtgccaacg gtggtggtgg acggccacgt tgcgttcggc     1920
tgggagagat acgctacggc gtcctactgt atgaacacgt acggcaagtc tctgcctcca     1980
gaagtgatct acgagtactt tggatacaac ccggcaacga ttgccaagaa ggtcgaagcg     2040
tacgtccggg cgtgccaaag agacccttttg ctgctccacg acttcctgga cctgaaggaa     2100
aagcctaacc acgataaagt aaataagctc tga                                  2133

<210> SEQ ID NO 48
<211> LENGTH: 2130
<212> TYPE: DNA
<213> ORGANISM: Pichia methanolica

<400> SEQUENCE: 48
atgagaattg caagagccgt ttcaacaagc gattacgaac atgatcaaat cattaagtat       60
ggtagagctt tggttctaga tatcgttcag caatacgacg gtggtcaccc aggttctgct      120
atgggtggta tggccttagg tatcgctcta tggaaataca caatgaagta tgctccaaat      180
gatccgacat attttaacag agatagattt gttttatcta acggtcacgt tgcttatta       240
caatatgtct tccaacattt cactggtttg aaatctatga ctatggacca attaaaatct      300
tatcactcta tgacttcca ctcacactgt ccaggtcacc cagaaattga acacgatgct      360
gttgaagtta ctaccggtcc attaggtcaa ggtattgcta actctgtcgg tttagccatt      420
gctaccaaga acttggctgc aacttacaac aaaccaggtt acaacttggt tgataacaag      480
acctattgta ttgttggtga tgcttgtttg caagagggtc cagctttaga agccatttca      540
attgcgggtc attatggttt aaacaacttg attgttctgt atgataacaa tcaagttttgt      600
```

```
gctgatggtt ccgttgatat tgccaacact gaagatattt ctgccaagtt caaagcctgt    660
aactggaatg ttattgaagt tgccaatgct tctgaagatg ttgccacaat tgttaaggcc    720
ctagaatacg cccaaaacga agtcaaagca ccaactttaa ttaactgtag aacagttatt    780
ggtgctgacg ctgcattcga aaaccaccac gccgaccacg taactctttt aggtgcagat    840
ggtgttagag aagttaaaaa aaagttgggt atgaacccag ctcagaaatt ccatgttcca    900
aaggaaattt accaattctt ttccaacaag attactgagg tgatcaatt agttgctgac    960 tggaagaaac ttgttgacaa ctatgtcaag gaatacccgg aattaggtaa agagttttta   1020
gcaagagtta gcggtgaact accagctgac tggaaatctt cattaccagt tcaagactac   1080
gctggtgaca cgccaaccag agctgctgct agaggcttgg ttcaagctgc aggtaaagct   1140
attccaaaca tcatggctgg ttgtgctgat ttatcagttt ccgttaactt acaatggcct   1200
ggtgttactt acttccaaga tccaagttta agaactaact gtggtttgac cggtgattac   1260
tctggtagat atctggaata tggtattaga gaacatgcta tgtgtgctat cgctaatggt   1320
atggctgcct ttaacaaggg tacttttatt ccaatcacct caacattctt tatgttctac   1380
ttgtacgctg ctccagctat tagaatggct ggtttacaag aattgaagac gattcacatt   1440
ggtactcacg attctatcaa tgaaggtgaa atggtccaa cacatcaacc tattgaatct   1500
ccatctttgt tcagagctat gcttaacgtt tactacatga accagttga ttctgctgaa   1560 gttttaggtt tgtttgaaaa agctatcgaa tgtccataca cttccatgct tcattatca   1620 agaaatgaag ttttacaata cccaggtcta tcgtctccag aaaaggccaa gagaggtggt   1680 tacatttag aagatgttga aaatgctgat gttcaactca ttggtgctgg tgctgaaatg   1740
gagttcgctt acaaagctgc taagatttta ggtagaaagg gtttgaaggt tagagttcta   1800
tccattccat gtactagatt gtttgatgag cattcattag gttccagaag atctgttttg   1860
agaaaagatg gtagccaagt tccaccagtt attgttgatg gtcatgttgc attcggttgg   1920
gagagataca gtactgcttc gtactgtatg aacacttacg gtaagtcatt accacctgat   1980
gttatttacg agtactttgg ttacaaccca aatactattg ctaagaaggt tgaagcatat   2040
gttaaggctt gtagagctga tccattatta ttacatgatt atgttgattt aaaggaaaaa   2100 ccaaaagcatg ataaggtgaa caagttataa                                    2130
```

<210> SEQ ID NO 49  
<211> LENGTH: 2121  
<212> TYPE: DNA  
<213> ORGANISM: Candida boidinii

<400> SEQUENCE: 49

```
atggctctcg caaaagctgc ttcaattaac gatgatatcc atgatttaac aatgagagca     60
ttccgttgtt atgtcttgga tttagttgaa caatatgaag gtggtcatcc tggttctgct    120
atgggtatgg ttgccatggg tattgcatta tggaaatata caatgaaata ttctacaaat    180
gatccaacat ggttcaatcg tgatagattt gttttatcaa atggtcatgt tgtttatt     240 caatatttat ttcaacattt atcaggtttg aaatctatga ctgaaaagca attaaaatct    300
tatcattcat cagattacca ttctaaatgt cctggacatc agaaattga aaatgaagct    360 gttgaagtta ctactggtcc attaggtcaa ggtattttcta attctgttgg tttagctatt    420
gcatctaaaa atttgggtgc attatataac aagccaggat atgaagttgt taataatact    480
acatattgta ttgttggtga tgcttgttta caagaaggtc cagcattaga atctattca     540
```

```
tttgcaggtc atttaggatt agataattta gttgttatt t atgataacaa tcaagtttgt    600
tgtgatggtt ctgttgatat tgctaatact gaagatattt cagctaagtt tagagcttgt    660
aattggaatg ttattgaagt tgaagatggt gctagagatg ttgctactat tgtcaaggca    720
ttggaactag ctggtgctga aaagaataga ccaacattaa ttaatgttcg tactattatt    780
ggtactgatt cagctttcca aaatcattgt gctgctcatg gtagtgcttt aggtgaagaa    840
ggtattagag aattgaaaat caaatatggt tttaatccat ctcaaaaatt ccattttcca    900
caagaagttt atgatttctt tagtgatatt ccagctaaag gtgacgaata tgtttctaat    960
tggaataaat tagttagtag ttatgttaaa gaatttcctg aattaggagc tgaatttcaa   1020
tcaagagtta aggtgaatt  accaaagaat tggaaatcat tattaccaaa taatttacca   1080
aatgaagata cagcaacaag aacatcagct agagctatgg ttagagcatt agctaaagat   1140
gttccaaatg ttattgctgg ttcagcagat ttatcagttt cggttaattt accatggcct   1200
ggatctaaat attttgaaaa tccacaatta gcaacacaat gtggattagc tggtgattat   1260
tctggtagat atgttgaatt tggtattaga gaacattgta tgtgtgctat tgctaatggt   1320
ttagctgctt ttaacaaagg tacattttta ccaattactt catcatttta tatgttttat   1380
ctctatgcag ccccagcatt aagaatggct gcattacaag aattaaaggc aattcatatt   1440
gctacacatg attctattgg tgctggtgaa gatggaccaa cacatcaacc tattgcacaa   1500
tctgctttat ggagagcaat gcctaatttc tattatatga ccaggtga   tgctagtgaa   1560
gtacgtggat tatttgaaaa agctgttgaa ttaccattat ctacattatt ttcattatct   1620
agacatgaag ttccacaata tccaggtaaa tcaagtattg aattagctaa agaggtggt    1680
tatgtatttg aagatgctaa agatgctgat attcaattaa ttggtgctgg ttcagaatta   1740
gaacaagctg ttaaaactgc tagaatttta agatctagag gattaaaagt tcgtatttta   1800
tctttcccat gtcaacgttt atttgatgaa caatctgttg gatatagaag atctgtttta   1860
caaaggggta agttccaac  tgttgttatt gaagcttatg ttgcttatgg ttgggaaaga   1920
tatgctacag caggttatac tatgaataca tttggtaaat cattacctgt tgaagatgtt   1980
tatgaatatt ttggtttttaa cccatctgaa atttctaaaa aaattgaagg ttatgttaga   2040
gcagttaaag ctaatcctga tttattatat gaatttattg atttaaccga aaaaccaaaa   2100
catgatcaaa atcatttata a                                             2121
```

<210> SEQ ID NO 50
<211> LENGTH: 2126
<212> TYPE: DNA
<213> ORGANISM: Kuraishia capsulata

<400> SEQUENCE: 50

```
atgagaattc caaaagctca gaactttaac gaagatatcc acgacttggt gattcggtct     60
ttccgctgct atgtccttga tctggtcgag caatatggag tggtcatcc  tggttctgcc    120
atgggaatgg tagccatagg tattgctctg tggaagtaca ccatgaagta ctcgccaaac    180
gacccaactt acttcaaccg tgatcgtttt gtccttttcta acggtcatac ttgtttgttt    240
cagtacctgt ttcagcactt gactggtctc aagtctatga cggtcaagca attgaagtcg    300
taccattcct cggactacca ctcattgact ccaggtcatc ccgagattga aacgatgcc     360
gttgaagtaa ccaccggtcc tttgggtcag ggaatttcca actcggttgg acttgccatt    420
gccacaaaga acttggctgc tctctacaac aggcctggtt ttgacgttgt taacaacaag    480
acatacgcca tcgttggtga tgcctgtctc caggaaggtc cagccttgga gtcgatctct    540
```

```
cttgcaggcc atctcggtct cagtaaccta atcgtgatct acgataacaa ccaggtttgt    600
tgtgacggat ctgttgatat cgccaacact gaggatatca gtgccaagtt caaggcttgc    660
aactggaacg tgattgacgt ttctgatgcg gctgaggacg ttgctactct ggtgcgtgct    720
ctggagtacg ccggccgcga aacttctaga ccaaccttga tcaatgcaag aactgttatt    780
ggtgctggtg ctgagtttga aaccattgc aatgctcacg gtaatgcatt gggtgaggca    840
ggtgttcgtg ctgccaaggt tcgctacgga ttcaaccccca accaaaagtt ctatttcccc    900
gaggaagttt acgatttctt tagtgaaatc cctgccagag gtgacaagct tgtttctgag    960
tggaaacaac ttgtttctgc ttactccaaa gcccatccgg aagtggctgc cgagttcctc   1020
ggccgtacta gaggtgagct gcccaagaac tggaagagtc ttttgccctc tgaagcacct   1080
acagaggcta ctgccactag aactactgcc cgtgaatgtg ttcgtgcctt tggcaaaggc   1140
gtttccagtg ttattgctgg gtctgccgat tgtcagtttt ctgtcgatct accatgggag   1200
ggcgtggagt acttcctcag tccagagctt gctacagaat gtggccttag tggttctttc   1260
agaggtcgtt acattgaatt tggtattcgt gagcattcta tgtgtgcaat gctagtgga    1320 ttggctgctt tcaatcctgg tacttttgtc ccaatcacat cctcatttta catgttctat   1380
ctatacgcag ccccagcatt gcgtatggct gcccttcagg aattgaaggc cattcacatt   1440
gcaactcatg attccattgg tgctggagaa gatggaccaa ctcaccagcc tattgcacag   1500
agtgctttgt ggagagccat gcctaacttc tattacatgc gtccagccga cgctactgaa   1560
gttcgtgcat gttttgagaa ggccgttgag cttcctgtct cgtcgttatt gtctctgtcc   1620
agacacgaag ttccacagta tcccggaaca tcttctcttg ccaaagcaaa gcgtggtggt   1680 tacgtctttta gagatgttga acgtccagac ttccagttca ttggtgttgg ctccgagatg   1740
gagtgggttg tcaaggctgc agaccttttg accaagacta agggataccg tatcaggatt   1800
ctgtctttcc catgtcaacg tttgttttgac gagcagagtg tgagctatcg tcgctcagtt   1860
ctgcgcagag gtgaacttcc aaccatcgta gtcgaagcat atgtggctta cggatgggag   1920
agatatgcca cggctggcta caatatgaac cctttggaa agtctctacc tgtggatgat   1980
gtttaccaat actttggttt cactccagag tcaattgccg acagagttga cagttatgtc   2040
aagcgtgtca aggccgagcc tcaattgctt tgggagttcc aggacttaaa gactcgtcct   2100
aagcacgaca agttgtaaac tagtaa                                        2126
```

<210> SEQ ID NO 51
<211> LENGTH: 2124
<212> TYPE: DNA
<213> ORGANISM: Komagataella pastoris

<400> SEQUENCE: 51

```
atggctagaa ttcccaaagc agtttcttac aatgatgaca tccatgactt ggtcatcaaa     60
accttccgtt gttacgttct cgacttagtc gaacagtatg gtggtggtca ccctggttct    120
gccatgggta tggtcgccat tggtatcgct ctgtggaagt accagatgaa gtacgctcca    180
aatgatccag actacttcaa cagagatcgt tttgtcttgt caaacggtca cgtctgtttg    240
ttccaatact tgttccagca cttaactggt ttgaaggaga tgactgtcaa gcaacttcaa    300
tcttaccact cttccgatta tcactcattg actcctggac accctgaaat tgagaaccct    360
gctgttgagg ttaccactgg tccccctggga caaggtatct ctaacgctgt cggtatggcc    420
attggttcaa agaacctggc cgctacttac aacagacctg gcttccctgt cgttgacaac    480
```

-continued

| | |
|---|---|
| actatctatg ctattgttgg tgatgcttgt ttgcaagagg gacctgcttt ggaatcgatt | 540 |
| tccttagccg gtcacttggc cttggacaac cttattgtga tctacgacaa caaccaggtt | 600 |
| tgttgtgatg gttccgtcga tgttaacaac accgaagaca tctccgcaaa gttcagagct | 660 |
| cagaactgga atgttatcga cattgtagac ggttctagag atgtcgctac cattgtcaag | 720 |
| gctatcgatt gggccaaggc tgagactgag agaccaactc tgatcaacgt tagaactgaa | 780 |
| attggacagg attctgcttt cggtaaccac cacgctgctc acggttctgc tctaggtgag | 840 |
| gaaggtatcc gggagttgaa gactaagtac ggttttaacc ctgcccaaaa gttctggttc | 900 |
| cctaaagaag tatacgactt ctttgctgag aaaccagcta aggtgacga gttagtaaag | 960 |
| aactggaaaa agttagttga tagctatgtc aaagagtacc ctcgtgaggg acaagagttc | 1020 |
| ctttctcgtg ttagaggtga gcttccaaag aactggagaa cttacattcc tcaagacaag | 1080 |
| cctaccgaac caaccgccac cagaacctct gctagagaaa ttgttagggc ccttggaaag | 1140 |
| aaccttcctc aagttattgc cggttccggt gacttatctg tctcaattct tttgaactgg | 1200 |
| gacggagtga agtacttctt caaccctaag ttacagactt tctgtggatt aggtggtgac | 1260 |
| tactctggta gatatattga gtttggtatc agagaacact ctatgtgtgc tattgccaac | 1320 |
| ggtttggctg catacaacaa gggtactttc ttgcctatta cctctacctt ctacatgttc | 1380 |
| tacctgtatg cagcacctgc cttgcgtatg gctgctcttc aagagttgaa agcgattcac | 1440 |
| attgctacac acgactctat ggagctggt gaagatggtc caacccacca gcctattgct | 1500 |
| ttgtcttcat tattcagagc tatgcccaac ttctactaca tgagaccagc cgatgctacc | 1560 |
| gaagttgcag ctctgtttga agtggctgtt gagcttgaac actccacatt gctttctctg | 1620 |
| tccagacacg aggttgacca ataccaggt aagacttctg cccaaggagc caaagaggt | 1680 |
| ggttacgttg ttgaagactg cgaaggaaag ccagatgtgc aactgatcgg aactggttcc | 1740 |
| gagttggaat cgctattaa gactgctcgt ttgctaagac aacagaaggg atggaaggtc | 1800 |
| agagttctgt cattcccatg tcagagattg tttgacgagc agtctattac ttacagacgt | 1860 |
| tccgtcctta agaggagaa agttccaact gtcgttgttg aggcctatgt cgcatacgga | 1920 |
| tgggagagat acgccactgc tggttacacc atgaacacct tcggtaagtc tcttcctgtt | 1980 |
| gaggatgtct acaaatactt cggatacact cctgagaaga ttggtgagag agtggttcaa | 2040 |
| tatgtcaact ctatcaaggc tagtcctcaa atcctttacg aattccacga cttgaaggga | 2100 |
| aaaccaaagc atgacaagtt gtaa | 2124 |

<210> SEQ ID NO 52
<211> LENGTH: 2240
<212> TYPE: DNA
<213> ORGANISM: Diaporthe ampelina

<400> SEQUENCE: 52

| | |
|---|---|
| atggctcctt ccgtagtaga tgtccccacg gacacagtct cccatctgcc gctgaaactc | 60 |
| tcagccaacg gcgacaagac gagtgggagac catggcagca tctcaaaact tgagctcaaa | 120 |
| gatgtcgcaa ggacggattt cgtcctgcgg accttcaggt gtctgattgc gaccttttgt | 180 |
| gagcagttca agggcggcca ccctgggagt gccatgggaa tggcagccat cggtgtcgcg | 240 |
| ttgtggaagt atgtgatgcg ttactcgcca gagaacccca gcttcttcaa ccgagacaga | 300 |
| tttgttctct caaatggcca ctgttgctta tggcagtata ccttcatgca ccttgtcggc | 360 |
| tacaagaaca tgacgcttga ccagctcagg tcctatcact ccgaccggac cgactcgatc | 420 |
| tgcccaggcc accctgagat cgaacacgag ggcatcgagg tgacgacggg acccctcggc | 480 |

```
cagggcatcg cgaacgccgt gggcatggcc atagccacca agcagctggg ggccacatac    540
aacaagcccg gcttccccgt ggtagacaac acaacgtggt gcatgatcgg cgacgcgtgc    600
ctgcaggagg gcgtcgggct cgaggccatc tcgctggccg gccacttcag gctgaacaac    660
ctcgtcgtgg tctacgacaa caaccagatc acctgtgacg ggtcggtgga cctgaccaac    720
accgaggacg tcaacgccaa gatgacggcg tgcggctgga aggtcatcga cgtcctggac    780
ggcaaccacg acgtcgaggg catcgtctct gccctggtgg aggcgcgcgc gagcaccgac    840
aagcccgtct tcatcaacat ccgcaccgtc atcggaatcg gcagcaaggt cgccggcgac    900
gcaaaggcgc acggtgccgc cttcggcgcg aagacgtcg ccaacatcaa gaggaacgcg     960
ggtttcgacc ccgagaaaca cttccagatc tcacaagagg tgtacgacta tttcgccgag   1020
atcaggagca ggggccgtaa tttcgagagg gagtgggacg acctcgtctc agcgtacggg   1080
ggctcgtacc cagacctggc caaggagttt gggcatcgcg tccgcggcga gttcccagag   1140
gactggacaa ggctcatccc caggaaggag gaattcccca cggcaccaac ggcctcgagg   1200
aaatccgcag gacttgtctg caaccgcctg ccgccaagc tgagcaactt catggtcggg    1260
acggcggacc tgagcccttc ggtcaacatg atctggaagg gcaagacaga cttccaacat   1320
cccgacctcc ggcccacgtg cggcatcacc ggcgactact cgggccgcta catccactgg   1380
ggcgtccgcg agcacgccat ggccgccatc tccaacggcc tcgccgccta cagcaagggc   1440
accatcctgc ccgtgacgtc gtccttcttc atcttctaca tctacgcggc gccggggatc   1500
cgcatgggcg ccctgcagcg cctgcaggcc atccacatcg gcacgcacga cagcatcggc   1560
acgggcgagg acggccccac ccaccagccc gtcgagctcg ccgccctgta ccgcgccatg   1620
cccaacctgc tgtacatgcg cccctgcgac agcgaggagg tcgccggcgc cttcgtcgcc   1680
gccctgtccg cccgcgacac cccctccatc atctcgctgt cccgccagaa cctcgagcag   1740
tacccggccc actcgtcgcg cgacggcgtc ctccgcggcg catacccctt catcgaggac   1800
ggcgaggcgg acgtgaccct catcggcgtc ggcgccgaga tggcctttgc cgtgcgcgcc   1860
cgcgacgccc tccgcgaccg ccacggcctg cgcgcccgcg tcgtcagctt cccgtgccag   1920
cgcctgttcg acgccagcc gcgcgggtac agggccgaga cgcttcggta ccgcggtggc   1980
gcaaaggccc ctccccgcgt cgtcgtcgag gcctacgccg caaacggctg ggagcgctac   2040
gccgacgccg gctactccat gagctccttc ggccactcgc tgcccggcgc cgccgcctac   2100
aagtacttcg gctacgaccc ggagctgatt gcgtcgcgcg tcgccgcctt tgtcggcgag   2160
tggaaggagc gcgggcccga cgagttccgc ggcgagttca gggatctcaa cctcggcggt   2220
gtggaccact agactagtaa                                                2240

<210> SEQ ID NO 53
<211> LENGTH: 2153
<212> TYPE: DNA
<213> ORGANISM: Aspergillus fumigatus

<400> SEQUENCE: 53
atgacgcaac aacttgaaga gaaaagaag attgatctcg cattgcgaac aatccgatgc      60
ctgatcttag acctttgcca acagtacaag gcgggcacc cgggggggcgc catgggaatg    120 actgcgattg gcattgcatt gtggaagtat tgcatgagat acgtcccaac gaaccccaac    180
ttcttcaacc gggatcgctt tgtgctctcc aacggccaca cttgcctctt tcagtacacc    240
ttcctgcatc tcacgggcta caaggccatg acgatggacc agttaaaatc gtaccactct    300
```

| | |
|---|---|
| gagcgggcag attccttgtg cccaggccac ccggaaattg aaattgacgg agttgaagtg | 360 |
| accacaggcc ccctgggcca aggtgtcgca aacgcggtgg gcctggccat ggcaacgaag | 420 |
| catctcggtg ctgtctacaa cagaccgaga ttctcacttg tggacaatac gacatggtgc | 480 |
| atggtcggtg acgcctgcct gcaggaaggc gttgcattgg agtcaatcca gctcgctggc | 540 |
| cactggagac tcaacaattt ggtcatcatc tacgataaca accaggtgac gtgtgatggc | 600 |
| agtgtggaca tctgcaactc cgaggacatc aacgccaaga tgagagcatg tggctgggat | 660 |
| gtgatcgatg ttgaagatgg ctgttatgat gtagaaggga tcactgctgc cctcatgcgt | 720 |
| gctcgctcca gcaaagagaa accgaccttt atcaacgtac gtaccgtgat tggcgtcgag | 780 |
| agcaaattcg ccggcgacgc caaggcgcac ggtgccgcct cggcgagga cgaggtcgcg | 840 |
| aacatcaagc ggaaacttgg attgaaccca gatgagcatt tcgctgtccc tgacgaggta | 900 |
| tatcagttttt tcagtgacgc tgggggaaga ggccgagccc tggaggagag ctggaatcag | 960 |
| ctcctactca attactcgac ggagcacccg gagatgtacg aggagttcag gttgagaatg | 1020 |
| ctcggaagga tgacacagga ctggacaaag ctcatcccgt caaaagaaga attccccgcg | 1080 |
| tctccaacag cctccagaaa gtctgccggc ctctgttgca atcccctggc ggcgaagctc | 1140 |
| gagaacatca tggtgggcac tgccgatctg actccttcgg taaacatggc atggaagggc | 1200 |
| aaggtcgatt tccagcatcc ggagctcaag accacttgtg gcctaaatgg caactacact | 1260 |
| gggcgatata tccactgggg tattcgggaa catgccatgg cttcaatctc aaacggacta | 1320 |
| gcagccttca caaaggaac tatcctgccc ataacctcca gtttctttat gttctacatt | 1380 |
| tccaagcagt ggtggctaac actgagcaag tatgcggccc cgggtatccg aatggcggca | 1440 |
| cttcagggcc tgcagcagat ccatatcgcg actcacgact cgattggcac cggcgaggat | 1500 |
| gggccgacgc accagcccat tgcattggca gcgctgtacc gtgcaatgcc aaatcttctc | 1560 |
| tacatacggc cctgtgatag tgaagagacg gctggggcgt ttatcgcagc aatgcaagca | 1620 |
| acatccaccc cgacaatcat ctcgctgtcc cggcagaact tggagcaata cccgaaattt | 1680 |
| tcctcgcgag aaggggtcca gcggggtgca tatgtttttca tcgaagatga gcaggctcaa | 1740 |
| gttacgttga ttggtgtggg tgctgagatg gtctttgcag tccgtacgcg acaggtgctg | 1800 |
| cgggaccgtt ttaacatcag atctcgcatt gtgagtttcc catgtcagcg tctttttgca | 1860 |
| cagcagagcc aagaatacag gagggaggtc ttgaaatatc ggtcaggaat cccccgtgtc | 1920 |
| gttattgagg catatgcggt caccgggtgg agagatacg ccgatgcggg cttcacaatg | 1980 |
| agcacatttg gacattccct acctggtgct gcagcatata gtactttggg attcgacgag | 2040 |
| catgtgattg caccagaggt ggcaaagctc gtggacgagg ttcagcggga cggcatcgaa | 2100 |
| agcttgcgag gtgacttcag ggacttgaat ccggtgcgcc gttagactag taa | 2153 |

<210> SEQ ID NO 54
<211> LENGTH: 2132
<212> TYPE: DNA
<213> ORGANISM: Pichia methanolica

<400> SEQUENCE: 54

| | |
|---|---|
| atgactgttt cagaatcctc tgcttctttg attcaagcta agcaagatca aacaaagttt | 60 |
| gatttcatgc taaatactaa cagaaacctt atcgttgacc ttgttcacaa ttacaaaggt | 120 |
| ggtcacggtg gtggaccaaa cggtatggcc gctattggtt tgcccttta caagtatgtt | 180 |
| atgaaataca acccagaaaa cccatcatac ttcaacagag atagatttat tctatcaaat | 240 |
| ggtcacacgt gtttattcca atacgctttc aatcatcttg ttggttactc tcacatgact | 300 |

```
ctcgaagaat taaaatctta ccactcagct gaagaagaat cactgtgccc tggccaccca      360
gaaattgagc accctgctat tgaggttacc actggtccat taggtcaagg tattgctaat      420
gccgtcggga tggctgttgc ctccaagaac ttggctgcaa cttacaacag agagggttc       480 cctgttgttg ataacactat cttctgtatg gtcggagatg cttgtttaca agaaggtcca      540
gctttagagg ccatttcgtt tgctggttct atgagattga acaacttggt tgtcacttac      600
gataacaacc aaatcagttg tgatggttca gttgatataa caaacactga agatatcaat      660
gctaagttta ttgcttgtaa ctggaatgtt attgatgttg aaaatggctc catggatatt      720
tgtgctattg ttcaggcttt ggaagatgcc aagttgtctg ataaaccgac tttaatcaat      780
attcacactg ttattggttt gagcactcca tgggaaaaca ccgccgctgt tcatggtgct      840
gatattggtc tgcaaatgt gttgaaattc aaagagaccg ttggtattga agccgataaa      900
actttctaca ttcctgatga aatgtacaaa tatttctcag atatcaaacc aaagggtcaa      960
gcgtatgaag cccaatggaa tcaattgatt acttcttatg aagccgcata cccagaattg     1020
gcagctgaat tccaaatcaa gattaaaggt gaactaccag caaactggaa agactacatt     1080
ccaacttcat tcccaaatgc tgacactcca tctagaaaat ctggtggttt agtcttgaac     1140
ccaatcgctc agcatttgaa ccaattcttg gttggtactg ctgatttatc tccatcagtc     1200
aacatgatat ggccaggaaa agttgatttc caagatccaa agaaggaaac tgcatgtggc     1260
ttgaatggtg attatactgg gcgttacatc cattatggta ttagagaaca tgccatgtgt     1320
gctatcgcca acgtattgc tgcttataac aaaggcactt ttattccagt tacttcaaca     1380
ttcttcatgt tctacttata tgccgctcct gccgttagaa tgggtgcttt aatgaacttg     1440
aaggttattc acgtcggtac tcacgattct attggtactg gtgaagatgg tccaacccat     1500
cagcctattg ccctagctaa cttctataga gctttaccaa acctatacta cattagacca     1560
gctgattcat tagaaactgc tggtgcttat gaagttgcca ttgaagctga aggctactct     1620
tcaattatct ctgaatcaag acaaaacttg gttcagtatc cagaaaactc aaagagagat     1680
gccgttaagt tcggtgccta cgtctttgat gactttaaca tcccggatgc caagaaggat     1740
ttaattatca ttggtgttgg ttcagagatg tgcttcgcca tgggttcggc tgctatctta     1800
agatcccaag gttacaacgt cagagtagtt tcattcccat gtcaaagatt gtttgaacaa     1860
caatcagctg aatacagaca ttctgtctta atgagacaac aaatgattcc aaccgttgtg     1920
atcgaagctt atgctccaaa cggctgggaa agatacgcca ccgctggtat taatatgaag     1980
acgttcggta agtccttacc aggtatggtc tgttacgact tcttcggtta caacaaggaa     2040
aagattgcta ctaaagtcga tgcttacttg aaacaaatta aggatactcc gtctgttgtc     2100
tatgagttcc aagatttgaa ctaaaactagt aa                                 2132
```

<210> SEQ ID NO 55  
<211> LENGTH: 2165  
<212> TYPE: DNA  
<213> ORGANISM: Scedosporium apiospermum

<400> SEQUENCE: 55

```
atggctcctg gtgataccgt agaagaagct gccctggccg acggcgtcac gaagtcgaca       60
tgcgtggact tgaggcaacg tgtcaaggac gagaaagcct cccacgatct ggttctcaag      120
acgttccgtc tgttaatcgc tgatctctgt caacagtata atggcggaca tcctggaggt      180
gcgattggaa tggcggcaat cggtgttgcg ctgtggaaat atgtgatgcg atatgcccct      240
```

| | |
|---|---:|
| cattctcccg actttttcaa ccgcgaccgg tttgtgctct ccaacggcca cacttgtctc | 300 |
| ttccagtacg ccttcctcca tctcacggga tataaggcca tgacctttga gcaactcaaa | 360 |
| tcctatcatt cggaccgata cgacgcactt tgcccgggcc atcccgagat cgaacacgaa | 420 |
| ggtatcgagg tcactacagg gcctctcggc cagggagtcg ctaactctgt tgggcttgct | 480 |
| ttggctacga agcacctcgg tgcgacttac aacaggcccg gttttgaggg tcttgtgtcc | 540 |
| aaccatacct ggtgcatggt cggcgatgct tgtctacaag agggcgtcgc gcttgaagcc | 600 |
| atttcccttg ctgggcactt taggttgaac aacctcacta taatctacga taacaaccaa | 660 |
| attacgtgcg acgtaccgt tgatctcaca aacacgaaaa acgttaatga aaagatgcaa | 720 |
| gcctgtggtt ggaacgtcat tgacatcgag gacggctgct tcgacgtcac cgggattgtc | 780 |
| gacgctctct tggcggcaaa gaaggccgat aaacccacct tcatcaacgt aaagacagtt | 840 |
| attggcgtcg gtagcaaagc cgccgggact gctgatgcac acggggcggc ctttggcgct | 900 |
| gccgatgttg ctagcatgaa acgcgcctac aattttgacc ccgagctgca tttcgtcatt | 960 |
| ggtgacgagg ttaggcagtt cttcgctggt attcctgctc gtggtgaggc ctacgtcgag | 1020 |
| gaatggaaca gtcttgtagc taggtatgag caggcttacc ccgagctcgg ggctaaattt | 1080 |
| cgtgaccgag tgacggggaa gctccctcct cggtggaagg agcttgttcc cgctcctgga | 1140 |
| acgttcccta ccgccccaac ggccagtcgt gctgcttccg gtttggtatt aaaccctatt | 1200 |
| gccaaagagc ttgaaaactt catggtgggg actgctgatc tatctccgtc ggtccatatg | 1260 |
| atttggcctg gcaaggttga cttccagcac cccgatctca agactggctg cggaatcaac | 1320 |
| ggaaactata ctggacgata tatacactat ggtatccggg agcatgccat gtgcgccatt | 1380 |
| gctaacggcc tcgcagctta ctctcccagc acaatcatcc ccgtcacttc atccttcttc | 1440 |
| atgttctatc tctatgcggc accggccgtc cgcatgggcg cccttcaacg tctcaaggtg | 1500 |
| attcacgccg cgactcatga ctccatcggt ctcggggagg acggccccac ccaccagccg | 1560 |
| attgagctgg ccactctcta ccgcgccatg cctaatatac tgtatatacg gcccggagat | 1620 |
| agtgaagaaa ccgctggtgc ctggatcgcc gctatcgaag cagaagggat gcccgccatc | 1680 |
| gtttccacca gccgccacaa gctccctcaa cttgcgcaga cgaagcgtga gggtgtcctc | 1740 |
| aggggcgcat atattcttca ggaaaacgaa aaggctgtcc tcactctcat cggcgtaggt | 1800 |
| gccgagttat gtcaagccgt cggtgtctcg gacaagctcc gggagcaggg tatcgagact | 1860 |
| cgcgtcgtca gtttcccttc atggaggttg ttcgagatac agcccctcga atacaagcgt | 1920 |
| gaggtgcttc gccgcagcca gattcccgcc gtagttatcg agccgtatgc cgctactggc | 1980 |
| tgggagcgct acgcggatgc gggtatttct atgaagactt ttggtcatag tctgcccgga | 2040 |
| ccggctgctt acaagtactt tggatttgac gtggactctc ttgccaggaa agtaacgggc | 2100 |
| tatcttcaga aactcaagca ggatgagctg cttaagcatg agtttgttga gctatgaact | 2160 |
| agtaa | 2165 |

<210> SEQ ID NO 56
<211> LENGTH: 2273
<212> TYPE: DNA
<213> ORGANISM: Aspergillus terreus

<400> SEQUENCE: 56

| | |
|---|---:|
| atggcaccct cactggaacc gttggaactc ctcgagaaac ccgccgcaac cctgccggtc | 60 |
| aaggcaatcg gcaacggggc ttcgctcaaa tacgaaagcc cagagaagca tcagcgagtg | 120 |
| atgaacgtct ttcgagcctt tatcgctgat ctcgcacagc aatatggcga aggccatgct | 180 |

```
ggatctccca tgggtatggc tgccatcggc attgccctgt acaagtatgt catgaaatac    240
tctcctacaa actgcaacta cttcaaccgg gaccgcttcg ttctctcgaa tggccacgcc    300
tgcttgtggc agtacctctt catgcacctt gtcggcgtca aaagcatgac tctcgaccag    360
ctcaagtcct accactcatc gaggctcgac tccgtttgcc cggggcaccc cgaaattgaa    420
cacgaaggcg tggaggtcac cactggtccc ctcggccagg gcctcgccaa tgcggttggt    480
cttgccgtgg ccacgaaaaa cctagccgca acatacaaca agcccggcca tgaggtggtg    540
aacaacatga catggtgcat ggtcggcgat gcatgccttc aggagggagt cgggcttgag    600
gcgctctccc tcgccggcca ctggaagctc aacaatctct gcgttatctt cgacaacaac    660
tgcgttacgt gtgacggcac tgcagacgtt gccaacaccg aggatatcaa caccaagatg    720
cgggctaccg ggttcaacgt ggtagacgtg cacaacggag actcggacgt tgccgccatc    780
gccaacgccc ttatcgccgc tcgatcgagc gacaagccca ccttcctcaa catccgcacc    840
acgattggct ttggagctgc aaaggccggc accgccgacg tgcacggcgc tgctcttgga    900
gtcgacgaag tggccaggat caagcggtcg tacggtctca acccagacga gcactttcac    960
atcccccagg acgtctacga cttttttccat gacattccca gccggggtga ggccctcgag   1020
gtgggctggc aagcggccct ggtaaagtat cacgaggaat accccgacct ggcggctgaa   1080
ttcgccctcc gcgtcgcggg caagatgact tcagactgga cgaaatgcat tcctcgcaag   1140
gaagagcagc cgactgcgtc gacggcgacg cgcaagtccg ccggcgtcat caccaacgcc   1200
cttggcgagc gcatcaactc attcctcgtc ggcactgcag acctcacacc ctcgtgcaac   1260
atcgcctaca agaacaaggt cgacttccaa tccgtgagtg cacatccaaa ctcccatacc   1320
ccaacccaag cccctaacac caaccagccc tccctccaaa ccgcctgcgg cctcaacggc   1380
acctacagcg gccgctacat ccactacggc atccgcgagc acgccatgtg cgccatctcc   1440
aacgggctcg ccgccttcaa caaaggcacc ttcatcccgc tgacaagcac ctacttcgtc   1500
ttccacctgt acgccgcggc cgcggtgcgc atggccgcgc tgcagggcct acagcagatc   1560
cacatcgcca cgcacgacag catcggcgtc ggcgagaacg gccccacgca ccagcccgtc   1620
gccgtcgccg cgctctaccg cgccatgccc aacctcctct acatccgccc ctgcgacgcc   1680
gaagaagtcg ccgccgccta caccgccgcc ctgcgcgcct cgcacacgcc cacggtcatc   1740
tcgctctcgc gccagagcct gccgcagtac ccgcagcact cgtcgcgcga gggcgcactg   1800
aaaggcgcgt acgtctttgc ggaggctgag ggtggcgagt ttgacgtgac cctgatcggg   1860 gtgggtcga agatggtctt tgcgatgcag acgcgcgagt tgctatgggc ggagtatggg   1920
attcgagcgc gcgtggtttc gttccgtgc acgaggctct ttgagctgca gtcgcgcgag   1980
tataagctgt cggtgctgag gcccgggat ggaaagccca ccgttgtgat tgaggcgtac   2040
ccggctaacg ggtgggagcg ctatgctgat gcgtcggtgt cgatgaatag ctttggaaag   2100
agtctgccct ccaaggaggt gtatgagcac tttggctttg cgccgagag catcgcgccg   2160 aaggttaagg atttggtgga ggaggtcagg cgcgatggga ttgggtcttt gagggggat   2220 tttagggatt tcaatggtgg tctgcggatt ggagttgagc attagactag taa          2273
```

<210> SEQ ID NO 57
<211> LENGTH: 2171
<212> TYPE: DNA
<213> ORGANISM: Rasamsonia emersonii

<400> SEQUENCE: 57

-continued

```
atgaccatcg aacaagccca tttaaacggc tctacagctg aaaacgatgg caccaatcag      60
gtttccagct ccgcccttcc tctcgtaaaa aagctgtcca aagaccacga tctggtcctc     120
aagacattcc gcctgctcgt cgcggatctg tgccagcagt tcaatggggg gcatcctggc     180
ggagcaattg gcatggcggc catcggggtg gccttgtgga ggtatgtgat gcgatacgcg     240
ccgcatacgc cggattactt taatcgcgat cggtttgtgc tgtcgaatgg ccatgcatgc     300
ctcttccagt acgtcttcct ccacctcacc ggctacaagg ccatgacctt cgaccagctc     360
aagtcctacc actcggaccg cgtcgatgcc ctctgtcccg acacccggag atcgagcac     420
gaaggtatcg aagtgacgac cggccctctc ggccagggcg tcgccaacgc tgtcggcctg     480
gccatggcca cgaaacacct cacggcgaca tacaaccggc cgggctacga ggtcgtctcc     540
aaccacacgt ggtgcatggt cggcgatgcc tgcctgcagg aaggcgtcgc gctggaggcc     600
atctctttcg ctggtcatct ccgcctgaac aacctgactg tcatctacga caacaaccag     660
atcacctgcg acggctccgt cgacctgacc aacaccgagg atgtcaacgc caagatgcgc     720
gcttgcggct gggacgtgat cgatgttgaa gacggatgct cgacgtcga aggaattgtc      780
caggctttgg agcaggcgcg cgcatcgagc gacaagccga cgttcatcaa cgtccggacg     840
atcatcggcc tggggagcaa agtcgcaggc acagctgatg cccacggagt ggcctttgag     900
gccgaagacg tcgctgcgca gaagaaggcc tacggattca acccggacga gttgtttgtc     960
atttccgaca ccgtgcgcga gttcttcgcc gacctccctg cccggggaga ggctctggtg    1020
caggaatgga acaagctggt cgatgaatac tcggcgaaat accccgacct gggcgccgag    1080
ttccgcagac gcatacgcgg agagctccct gccaactgga aggacttgat tccgaccagc    1140
ttccccgaca aaccgactcc ttcgcgcgcg tcgtccggac tcgtgttcaa tcccgtcgca    1200
aaggagatca attccttcgt cgtggggacg gccgatctgt cgccgtcggt gaatatggcc    1260
tggcctggca aggtggactt ccagcatccc gacctgcgaa cgacctgcgg cctcaacggc    1320
aactactccg ggcgatacat ccactacggc gtgcgcgagc atgccatgtg cgcgattgcc    1380
aacggtctgg cggcgtttgc ccccaacacc atcatccccg tcacatcctc cttcttcatg    1440
ttctatctgt acgctgctcc cgccgtgcgg atgggcgcgc tacagcagct ccagatcatc    1500
cacgccgcga cacgactc catcggcatg gcgaggacg ggcccacgca ccagcccatc    1560
gagctggcca gtctgttccg ctccatgccc aatctgctgt acatccggcc cggcgacagc    1620
gaggaaacgg ccggcgcgtg gatcgtcgcc atcgaggcga agcgcacgcc caccatcatc    1680
tcgacgtcgc gacatgcggt gccgcagctc aagcagacgc gacgggaggg cgtcgcccga    1740
ggcgcctatg tgctggaaga agtcgccgac aagagagcgg acgtgacgct gatcggcgtc    1800
ggggcggagc tttccttcgc ggtcgaagtc gcgcagcagc tgaagaagag gaacatcgca    1860
gcccgcgtcg tgagcttccc ctgccagcgt ctgtttgagc aacagcccgt cgagtacagg    1920
cgggagacgc tgcagcgaca ccgcggcatc ccggcggtcg tgattgagcc ttacaccccg    1980
aacggatggg agcggtatgc ggacgcgggg atttgtctga agcggtttgg acacagtctg    2040
ccggggaagg cggcgtacaa gttctttggg tatgagattg atgtgctgac gggcaaggtg    2100
gtggattatc tggagagaat acgggaagat gagttgttga ggagggagtt tgtggagctg    2160
taaactagta a                                                         2171
```

<210> SEQ ID NO 58
<211> LENGTH: 2234
<212> TYPE: DNA
<213> ORGANISM: Exophiala aquamarina

<400> SEQUENCE: 58

```
atggcgcctt ctttggaata ctatgaagct gtctcgggag gggaactccc ggttaaagct        60
atcccgacca aaaccaatgg agtcgaagct gttagcggcc tgcaactaga tcagagtgag       120
aaacatgaga ttattcttaa gactttccga gcgtttatcg ccgatctatg tcagcaattc       180
ggaggcgggc atcctggcgg tgcaatggga atggctgcta ttggaatcgc gctatacaaa       240
tatgtcatga agtattctcc tacaaacgta gggttcttca atcgagatcg tttcgtccta       300
tcaaatggac acacatgctt gtttcagtat ctgtttatgc accttgtggg cttcaaatcc       360
atgacgatgg agcaactcaa gagctatcac tccgaccgaa ccgactctct ggctcctggc       420
catccagaga tcgagaatga aggcgtggaa gtgacgacgg tccactcgg acagggtgta        480
gcgaatgcag ttggcctcgc catggccaca aaacaccttg gtgcgacata caaccgccca       540
ggccacaccg tcgtcgacaa tatgacgtgg tgtatgattg gcgacgcatg tcttcaagaa       600
ggcgttgctc ttgaggccgt tgcgctagct gggcattgga agctcaacaa tttagcgatt       660
ctctacgaca acaacaatat cacttgcgat ggctccgcag atgtggcttg tacggaggat       720
atcgatgcga agatgcaagc atgtggttgg aatgtgatcg atgtctacga cggagaccac       780
aatgtcacag ggatcgtaca agcattgctg accgcacgaa tcagccagaa accaacctt       840
atcaacatca gaaccatcat cggaatcggg agcgctgcaa ctaacaacgc caaagctcat       900
ggtgctgctt tcggagttga cgacgtcgcc cagatcaaga ggaattttgg ccttgaccca       960
gagaagcact ttgaaatctc gaaagacatc tacggcttct ttgaggatgt taaacatcgc      1020
ggtgagagcc tcgaggctga gtggagcgcc acggtcaagg attacgaagc gcagtatccc      1080
gagcttgcag ctgaattcaa gcttcgagtc caagggaaga tgcccgtcga ctggactaag      1140
ttcattcctt caaaggacca attgcccacc aaaccaacgg catcacgcaa gtctgcaggc      1200
attgtctgca actctctcgc ggaaaacatg tcgaactttc tcgtcggaac ggccgacctc      1260
acgccttcgg tgaacttgag ctacaaacaa caggtggatt ccaatcacc cgacttcgta       1320
gcggcatgcg ggatgacggg agcctactcc ggccgctata tccactacgg gatccgggag      1380
cacgcgatgt gcgcgatctc gaacggactc gtggccttca cagggggaac cttccttccc      1440
gtgacgagca cattcttcat gttctacatc tacgcagccc cagcggtacg tatgggcgcg      1500
ctgcaagggc tccaacaaat ccacatcgca acgcacgaca gtatcggtac aggcgaagac      1560
gggccgacgc atcagcccat cgccctaccc gcactctacc gcgcgatgcc caacctgctg      1620
tacatccgcc cgtgcgatag tgaggaagta gccggggcgt tcatcaccgc gattaaggca      1680
acgtccaccc cgagcatcat ttccctctcc cgccagaact tgacgcagtt cccggaatac      1740
tcgcaccgcg acgcgtcca gagggcgcc tacgtcttca tcgaagacgc ggctgcagat        1800
atcacgctca tcggcatcgg ctcggagatg ggcttcgccg tctcaacacg caccctcctc      1860
aaggagagat ataacatcaa cgcccgaatt gtcagcttcc cttgccagcg gctcttcgag      1920
cagcaatcgc gcgactacaa ggaatccgtg ctgcgctaca atcttcgtg tccgatcgtc       1980
gtcatcgaag cctacgccgt aaacggctgg gagcggtacg cagacgcagg agtaagcatg      2040
aaatcctttg ggaagtcgct tcccggagat gtcgcgtata ggcatttcgg gtttgagccg      2100
agtgttatgt cgcagaagat taaggggttc gtcgaggagg tgagggcgat ggacggtggg      2160
gtgcgcgctc tgagaggtga gtttagggat ctgaatggcg tgatgggttt tggcttcgag      2220
cattgaacta gtaa                                                        2234
```

<210> SEQ ID NO 59
<211> LENGTH: 2201
<212> TYPE: DNA
<213> ORGANISM: Magnaporthe oryzae

<400> SEQUENCE: 59
atggcgtcgt ctgagcaaag ctctacggct ctatccagcc agagaaagcc cctggatctg 60
cctcagctca agtcagaaga agaccatgat gttgttctca agaccatccg gatgttggta 120
gcggatctat gccagcagtt tggtggcggt cacccaggtg gcgctattgg tatggcagcg 180
atcggggttg ctttatggaa atacgttatg cggtactcgc ccgaagagcc ggaatatttt 240
aaccgcgacc gcttcgttct ctcaaatgta ggagcttccg taaagcttac cctcggcttg 300
tccacaggac atacctgcct tttccaatac gtcttcttgc acttgagcgg ctacaaagcc 360
atgacctttg accagctcaa gtcataccac tcgaaacgta cagatgccct ttgcccaggt 420
caccccgaga ttgagcacga gggcgtcgag gttaccacag gtccactggg acagggcgtg 480
gccaacgccg tcggccttgc catggcgacc aagaacctcg cctccaccta caaccgacct 540
ggttttcccg tcgtcgacaa ccacacttgg tgcatgattg gcgacgcctg tctgcaggaa 600
ggcgtggccc tcgaggccat atccctggcc ggtcacctgg cgctcgacaa cctgactatc 660
atctacgaca acaatcagat tacctgcgac gggtccgtgg acctgacgaa taccgaggat 720
gtcaacgcca agatgagggc gtgcgggtgg catacagtgg atgttgaaga cggctgcttc 780
gacattgggg gcatcgtcag ggccctggct gaggcgcgac aggccgcgca tgggaaaccc 840
acgttcataa acgtccggac cgtcatcggg ttgggcagcg ccgtcgctgg caaggctgag 900
gcgcatggcg cagcgttcgg ggctgccgac gtcgcaaata tgaagcgcag cgttgggttc 960
gacccggaac agcactttgt catcggcgac aaggtacgcg acttctttgc cgacattccc 1020
aagaggggcc acaatcttgt cgccgattgg aagggtcttg ttagcaagta cgccgaagcg 1080
caccccgagg tggctagtga gtttgatagg agaacgaagg gcgagctccc ggagaactgg 1140
agggaactta ttcccaagag cttttctgac aagcccacgg caacgcgggc ttcttccgga 1200
ttggtgctca acccgattgc caaggatgta aaatccttca tggttgggac tgcagacctg 1260
acgccgtctg ttcacatgac atgggatggg atggaggact tccagaaccc caacatccgg 1320
ccaacctgcg gcatcaacgg ttcctacaca ggacgctaca ttcactacgg cgtccgcgag 1380
catgccatgt gcgccatctc caacgggctc gctgccttca atccgggcac ctttgtgccg 1440
gtgacttcgt cctttttcat gttctaccta tacgcggcac ccgcggtgcg catgggcgcc 1500
ctccagaagt tgcaggtaat ccacgctgcg acgcatgaca gcattggcat gggcgaggat 1560
ggacctactc accagcccat tgagctggcg acgcttttcc gcgcaatgcc gaacctgctg 1620
tacatgcgac cagccgacag cgaggagact gcgggtgcct gggaggtcgc catcgccgag 1680
aggaccaggc cgagcatcgt cagcacaagc agacacaagc taccgcagtt ggttggcaag 1740
tcgagccgta aaggcgtggc caagggcgcc tacgtcgtgt cggagccggc ggacggcaag 1800
gcggacgtga caatcctggg tgttggggca gaactttgcc tggcgctgga cgtggccgaa 1860
gccttggcgg ggaagaatat caaggtccgc gttgtaagct ttccttgctg gcggctgttt 1920
gacgagcagc cagttgcata taggcgggag acgcttcggc ggcatgaggg cattcctgcc 1980
gtcgtcgtgg agccctacgc gccgaacggg tgggagcggt atgctgacgc cggcgtgtgt 2040
ctacggcgat ttggacactc actgccggga ccagaagcgt acaagtactt tgagtatgaa 2100
acgccaaagg ttactgaaaa gattgagggg tatctaaagg gcctggagac gggagagtgg 2160

```
ttgaggggggg agtttgcgga cttgcaaatt tgaactagta a                 2201
```

<210> SEQ ID NO 60
<211> LENGTH: 2174
<212> TYPE: DNA
<213> ORGANISM: Verruconis gallopava

<400> SEQUENCE: 60

```
atggctccag gacttgtttt tgcgcccgtt gttgacggcc agcccgcagc gaagtcggtg   60
ttgccagaag gatcattccc tacaggcaat gagctgattt caaaacatga tatagttttg  120
aagaccttca gacttttgat tgctgacttg tgcgagcaat tcaaaggagg tcatcctggc  180
ggggctatcg gcatggcagc aatcggagtt gcgttgtgga gatacgtaat gcagtatgcg  240
ccgcacactc cagacttctt caacagagac agatttgttt tgtcgaacgg tcatacgtgc  300
cttttccagt acacgttcct gcacctcacg ggctacaaag ccatgaattt tgatcagctc  360
aagtcatacc actctcaaag aacggactct ctgtgcccag tcatcccga aatagaaatt   420
gagggcatag aggttaccac tgggccgttg gccagggcg tcgcgaactc agttggtttg   480
gctatggcta gcaagcacct tgggacaaag tttaaccgtc cggggtttcc tgtggtctca  540
aatcatatct ggtgcatgat tggcgacgcg tgtcttcagg agggcgttgc gttggaagcc  600
atttcattcg ccggtcatct tcgtttgaac aacttgacga tcattatga caataatcag  660
ataacatgtg acggctcagt cgatctgacc aataccgaag atgtcaacgc gaagatgcgt  720
gcatgtggtt gggacgtcat cgatgttgaa gacgcaaact ttgaagtcat ggccatagtt  780
gaagctctag agaaggccaa atcatctgcg cataagccca ctttcatcaa ctgtagaacg  840
gtcattggtc ttggaagcgc agtagccggc caggcgcaag ctcatggggc agctttcggt  900
gagaaggatg tggaagcaat gaaaacggcg gcaggattcg atccgaagca aagttcgtt   960
gttcccgacg ttgttcgcga gttcttcgca gatctgccag aaaggggcca gagatcgtg  1020
gaacagtgga atgacctggt taaaagatac gccacggagt atccctccct tgccgccgag 1080
ttccaatcgc ggttccgcgg cgaattgcca tctaactggg aagatctcgt cccaaactcc 1140
tttcccgaaa agccgacgcc atcacgcgca tcctcaggcc ttgtgttgaa tcccatagcc 1200
aagaatgtgg atgccttcat ggttgggacg gcggatctat ctccatcagt ccatatgact 1260
tggcccggaa aggttgattt tcagcatcct gacttgcgaa ccagttgcgg cataaatgga 1320
gattacaccg gccggtacat ccactacggc gtccgcgaac atgcaatgtg cgccatatcc 1380
aatggtctcg cggcgtacgc accaaacacc ataatcccag ttacgtcgtc cttttcatg   1440
ttctatctgt acgccgcacc agcggtacgc atgggagctt acagcgact tcaggttatt   1500
cacgctgcga cacatgattc aattggcatg ggtgaagatg gtccaactca tcaacccatc 1560
gaacttgcaa ctctgtatag agccatgccg aacctcctct acattcggcc agcagacagc 1620
gaagaaactg ccggagcctg gatcacagcg atcaaagcaa agaatactcc ttctatcatc 1680
tcaacgtcga gacacgccgt tcctcagctg aagcagacac gaagggaaaa agtggccctt 1740
ggcgcctatg tgcttgagga ggtggacgac gaaaagccag atcttacgct catcggtgtt 1800
ggcgcagagc tgtctcacgc ccttgccgtt gcggagaacc tccgaagaga tcggaacctg 1860
cgcgtccgcg tcgtcagttt tccgtgttgg cggcttttcg agcagcaacc tgtcgagtac 1920
aaacgaagtg ttctgaagcg acacctcagt attcctgccg tcgccatcga gcctacgcg  1980
cccaacggct gggaaagata cgccaacgca gcggcaagta tgacgcgctt tggacattca 2040
```

```
ttgccgggga ctgcggcgta caagtatttt ggattcgacg tggacggtct tacggtgaaa   2100
gttggaaact atctagatgc aattgaaagg gatcctgttc ttcggacgga atttgtagag   2160
ttataaacta gtaa                                                      2174
```

<210> SEQ ID NO 61
<211> LENGTH: 2120
<212> TYPE: DNA
<213> ORGANISM: Debaryomyces hansenii

<400> SEQUENCE: 61

```
atgaatcaaa ttgaagattt atcgttaaaa actattaggt gtttggtgag tgacctagta     60
caacaatata atggcggcca tccagggggt gcaatgggaa tggctgccat ggtatagca    120 ctttggaaat atatattaaa gtacaaccca aaaaatgcca attggtttaa tagagatagg    180
tttgttttgt ctaatggaca tacttgtctt ttccagtacg ttttcttaca tcttgttgga    240
tatgagtcat tcaccatgaa tcagttgaag aagtaccacg ccccagaagt gtctcaatgt    300
gctggacatc cggaaattga gtttgaaggt attgaggtta ccacgggtcc attaggtcaa    360
ggtattgcca acgcagtcgg tttggctatt gcctcgaaga acttagctgc aaattataac    420
aaacctgatt tggatttggt tgataacaaa atttattgta tggttggtga tgcttgtatt    480
caagaaggtg tcggcttaga agccatttcg cttgctggtc atttgggttt agataatttg    540
attgtgattt acgataacaa tcaaatcact tgtgatggtt ccgttgattt agcaaactct    600
gaagacatca atgctaagtt tatgggccaa aaatggcatg tgttaactgt tgacgacgga    660
agctttgatc ttagatctat attggctgcg attgagcagg caaagtcagt aaagggtctg    720
cctatcttga ttaatataag aacaatcatc ggtgtggata caaatgttgc taataatgcc    780
aaagcacacg tgctgcgta tggtgtagaa gaaggcagaa ggcttaaggc cctttatggc    840
tttgatcctg accaatttat tgaagttcca aaattagtct atgactttt tagagaaggc    900 aacgaagggg ccatttcaaa aggtgtcttt catcaggaac aatgggaaaa aaagttggag    960
gcatatagca agaaatatcc tcaattatac gaagaggtcg tatccagaat taatggaaag   1020
ttgccaaccg attggaaaga atcttttaccg cactcacttc caacagatgc gactgcttct   1080
agaaaggcat cgggattagt atttactcca cttgctgcca aatatccaca attcctcgtc   1140
ggcacagcgg acttatctcc atcagtgaac ttgttatggc cacataaaaa agattttcaa   1200
aaccctgaaa tcaaaactga ctgtggtatc aatggcgatt acagcggaag atacttacac   1260
tatggtatcc gggaacatgc catgtgtgcg atttctaatg gtatctcagc ttactccaaa   1320 ggtgcttta ttccaatcac atcttcgttt ttcatgtttt atctttattc tgcaccagcc   1380
gtaagaatgg gtgcgttgca gaatttacag gttattcatg tagcaaccca tgactcaatt   1440
ggaactggtg aagatggtcc tacacatcag cctattgcgt tagcatcatt ctacagatca   1500
ctaccgaact gtttgtatgt gagaccagcg gacaacgaag aagttgcagg cgcatgggaa   1560
cttgctattg aaaccactaa taaaccgaca attatatcct tgtccagaca gaatctcaag   1620
cagtaccctg gtatcacgga ccgtaacaaa gtgaaatttg gtgcatacgt attgaaggaa   1680
tttgactcat catcagacag ccaaaagtta caaattatat ccgttggtgc agaaagtcaa   1740
tttgctattg atgctgccga aatattgatt gagtcaaaca ttaatgttaa aattatttca   1800
tttccatgcc agcgactttt cgaatgtcaa tccacagagt ataagagatc cgtcttggat   1860
ccccaaatcg tgaccgttgc tattgaagcc tatgcttcca atggatggga aaggtatgct   1920
aatgctggtt tccacctaaa cgaatttggt atatcattac ctggtaaaaa tgcatatgag   1980
```

| | |
|---|---:|
| catttcggat ttaatggcgc ttatatcgcc agcaaaattc aaaaatactt agatgatttg | 2040 |
| caaaaggatg atattatgaa gtttgaatat caagaattga atattacgaa aaatcatcat | 2100 |
| tcttcttctt gaactagtaa | 2120 |

<210> SEQ ID NO 62
<211> LENGTH: 2216
<212> TYPE: DNA
<213> ORGANISM: Fonsecaea erecta

<400> SEQUENCE: 62

| | |
|---|---:|
| atgagcccta ttgctgttcc cgtcgaggga cagtcaatgc aactccccga cgccgactac | 60 |
| aagctggcca acagtgtgaa aaagggccag acaacatcaa caacgaatgc ctcaactcag | 120 |
| ctgagccccg aagaagaact ggtgttgaag agcttcagag tgctcatcgc cgacctatgc | 180 |
| cagcaattca aggcgggca tccaggaggc gcgatgggaa tggctgccat tggtgttgcg | 240 |
| ttgtggaaat acgtgatgca ctacgcgccg cacagtccag attggatcaa ccgcgatcgg | 300 |
| tttgtgctgt ccaacggcca tacctgcttg tttcaatact gcttttgca tctgaccggc | 360 |
| tacaaggcca tgacgctgga acagctgaag tcatatcatt cggatcggac cgactcgctg | 420 |
| tgccccggcc acccggagat cgagcacgag gggatcgagg tcaccacggg tccacttggt | 480 |
| cagggcatcg ccaatgcggt gggaatggcc atggcttcca agcatctcgc ggccaagttc | 540 |
| aaccgaccag gcttcgacat cgtgtccgac catgtctggt gtatggtcgg tgatgcctgc | 600 |
| ctccaagaag gggtcgggct cgaggccatc tcctttgccg gcacatgcg tctgggtaac | 660 |
| cttaccgtga tatacgacaa caaccagatc acctgcgacg gcccggtcag tctgaccaac | 720 |
| accgaggaca tcaatgccaa aatgagggct tgtggctgga atgtgatcga gatcgcagac | 780 |
| gggtgctggg atgttcgggg catcgtcaag gctctggagg cttctcgtgt ctcagaccgc | 840 |
| ccaacgttcg tgaattgcca cactgtcatc ggcgtcgaca cggccgttgc tggggacgcc | 900 |
| gtggcgcacg gagcagcgct gggagtggac acggttatgg ccctcaaaag actctacggg | 960 |
| ttcgatccag aacagcgata tgtcatcccc gacacggttc gcgagttctt cagtgggctc | 1020 |
| ccctcccgag gacagtctct ggtgaccgag tggaatcaca tgctccagga gtacagccaa | 1080 |
| gtttaccctg acctggccga agaatatgca acacgcatca gtggtcactt accggacagc | 1140 |
| tgggagtctc tgattccgca tccctcccc tcaaagccga cggcaacccg cgccgcgtca | 1200 |
| ggattggtct tcaacccgct cgctgaaaga cttgaccggt tcatggttgg gactgccgac | 1260 |
| ctgtctccgt cggtgtacat gagctggaag accaaggaag atttcgagcc ccttctctg | 1320 |
| gggacgggaa gttattctgg gcggttcatc cactatggtg tcagggaaca tgccatggcg | 1380 |
| gccatttcga atgggttggc agcctatcat cctgggatgt tcattccggt tacatcaagc | 1440 |
| ttcttcatgt tctacctata cgcagctccg gccgtccgaa tgggcgcgct gcagcacctg | 1500 |
| caagtcatcc acgccgcgac gcacgattcg attggcatgg gcgaagatgg gccgacgcac | 1560 |
| caacccatcg agcttgccgc gctgtaccgc gccatgccga acttgctgta catccgaccg | 1620 |
| ggagacagtg aggagaccgc aggtgcctgg atcgaggcca tcaaagccag acacatgtcg | 1680 |
| tccatcatct ccacgtcccg ccacgcgctc ccacagctga ccggcctgac caaacgcacc | 1740 |
| gaagtggcca agggcgcgta cgtcctcgaa gaagtcgtct caggaaccgc cgatctgacg | 1800 |
| ctgatcggcg tcggggccga gctcaacctc gccgtccgcg tggcggccga gctgcgcagc | 1860 |
| tcctcccacg gtctgaaagt gcggacggtg tcattcccgt gccagcgcct cttcgacgcc | 1920 |

| | |
|---|---|
| cagccgcgcg cgtatcagcg ccacgtgctc cagcgccaga gcggcgtgcc cgtcgtggtg | 1980 |
| atcgaggcgt acgcggcgaa cgggtgggag cgctacgccc acgcggccgt atgcatgagc | 2040 |
| acgaagcgct ttggcaagtc gctgcccggg ccgaaggcgt acgagtactt tggcttcgac | 2100 |
| gtcccctcga tggtggcccg gatcgcggga tatctggacg attggaaggc ggatccggac | 2160 |
| ttgaggcatg actttgtaga attgacgtgt gcgaaaacgg atgcatagac tagtaa | 2216 |

<210> SEQ ID NO 63
<211> LENGTH: 2156
<212> TYPE: DNA
<213> ORGANISM: Baudoina compniacensis

<400> SEQUENCE: 63

| | |
|---|---|
| atggagccta acgacaggac tcaatacgta gttcgatgct accgcgcact aattgcagat | 60 |
| ctatgccagc aattcaacat gggccaccca ggctcggcga tgggtatggc agcaatcggc | 120 |
| gtagcgctct ggaagtatgt gatgaagtac tcgcccaaga acgccgactt cttcaaccga | 180 |
| gaccgcttcg tccttttccaa tggccatgcg tgcctgttcc aatacacgtt cctacatttg | 240 |
| acgggatacc aagccatgac cttgagcaa ctatctagct atcacagcga gcgatgggac | 300 |
| tcctacacgc ctggccaccc ggagatcgag catgagggca tcgaagtcac gactggaccg | 360 |
| ctaggccagg gtatcgccaa cgctgtaggc ctggcgatgg cgacgaagca tcttggcgct | 420 |
| gtctacaacc ggcctggctt cgaaatggtc aacaacatga cgtgggttac gatcggcgac | 480 |
| gcatgcctgc aagaaggcgt cggcatggaa gcgattcaac ttgccggaca ttggagactc | 540 |
| gacaatctct gtgtgatcta cgacaacaac cagatcacct gtgacggctc agtcgacata | 600 |
| tgcatggcgg aagacgtcaa catgaaaatg cgcgccagcg gtttcgaagt gctcgaggtc | 660 |
| gaagacggca accatgacgt cgaaagcatt gtcaaggcgc ttgtggctgc ccgggctaac | 720 |
| aagaagaggc caacgttcat caatatcaag accacgatcg gcgtcggcag taaaaagcaa | 780 |
| ggcatagctg acgttcatgg cgcgccgctt ggcaaggagg atgtagctca catcaaggag | 840 |
| agctttggac tcgactccag caaaattcta gaggtgccgc aagaagtgta tgacttcttc | 900 |
| cgggaggccg ttccgcgtgg gcagcagctc gagaaggact ggaatggctt gctttctaag | 960 |
| tatagtaaag agcacccaga tctggcggcg gacctcaaga agcgcatgaa tggagagatg | 1020 |
| cttgacgact ggacaaagta catcccgaag aaggaggact cccactga gccgacacca | 1080 |
| tcacgcaagt cagctggggc agtctgcaac ccgctggcga agaacgtagg taacttcatg | 1140 |
| gtcggcacgg ctgacctcac accctcggtc aacatggctt ggaagggtaa ggtcgacttc | 1200 |
| caacatccag atcttcgaac tgcttgcggc atcaatggcg actacactgg tcgctacctc | 1260 |
| cactggggta tccgcgagca cgccatggca tccgtgtcga acggtatggc ggcgttcaag | 1320 |
| aagggatgca tcctgccggt cacgtctagc ttcttcatgt tctacatcta cgcagcgccg | 1380 |
| ggagtgcgga tgggtgcgct gcagagtctg caggtcatcc acattgctac ccacgactcc | 1440 |
| atcggcacgg gtgaagacgg accgacgcat cagcccatcg agcttgcggc gctgtacagg | 1500 |
| gctatgccaa acttcctcta tatccgcccct tgtgatggcg aagaggcggc tggtgccttc | 1560 |
| attgccgctg tcgcgccaa aaacacgcct tccatgatct ccgttgcgcg ccagaacgtc | 1620 |
| gagcagttcc cgaagtattc gagccgcgag ggcgtgcaga agggagccta tgtcttcatc | 1680 |
| gaggagcaag atgcggacgt cacgcttatc ggtgtcggcg cagagatgac cttcgcagtc | 1740 |
| ggcgccgcga aggtattgaa ggacaagcac ggtatcaagg ctcgcatcgt cagcttcccg | 1800 |
| tcgcaacgtc tcttcgagga gcaaccgata gaatacaagc gtgaagtcct gcaatatcgc | 1860 |

```
tccaacgcac cgcgcgtcat catcgaagca tatactgtca acggctggga acggtacgcc    1920
gatgctgggt actcgatgca cactttcggc cattctttgc cacgacaata tgtgtatggc    1980
cgcttcaact tcgacaacga caagatcgcc gccaagatcc agccattggt gcaggaggtg    2040
aagaagaacg gtatcgagag cctgagggga gagttccggg atctcaatac cgactacccg    2100
cgcgacgtct ttcatagcgc gtttggaacc agtcatgtag tgtcataaac tagtaa       2156
```

<210> SEQ ID NO 64
<211> LENGTH: 2201
<212> TYPE: DNA
<213> ORGANISM: Mycobacterium

<400> SEQUENCE: 64

```
gtgcggccgc cagaggccga tgaaccgaag gggagaaatc gtgactcaga cagcagatgc      60
gatccttgcc gagcccaatt cgacaccgtc ggtgttgaac tggacaaccg aggaccagcg     120
tgccgtggac accgtccggg tgctggccgc ggatgcgtgg agaaggtcgg caacggtcat     180
ccgggtacgg cgatgagcct ggctccggcg gcgtacctgt tgttccagaa gctgatgcgc     240
cacgaccccc gcgaccctga ctgggtgggc ggtgaccggt tcatcctctc gccgggccat     300
tcgtccgtga cgctgtacat ccagctgttc cttgccggtt acgggctgga gctggaggat     360
ctgaagtcct tccgcacctg gggttctctg acgcccggcc atccggagta caagcacacc     420
aagggcgtgg agatcaccac cggcccgctg gtcagggtc tcgcgtcgtc ggtcggattc     480
gcgtactcgc agcgccggat gcgcgggctg ctcgacccgg acgcagcccc gggaacctca    540
ccgttcgacc acacgatctg ggtgatcgca tccgacggtg acctgcagga aggtgtgacg    600
tccgaggctt cctccctcgc cgggcaccag gagctgggca acctcgtcgt ggtctacgac    660
gagaaccaca tctcgatcga ggacgacacc gacatctcgt tcaccgagga cgtcctgggg    720
cgctacgagt cctatggctg gcacgtccag cgcgtggact ggacccgcac cggtgagtac    780
cgggaagacg tcgaggaact gttcgcggct ctgctggcgc gaaggcggaa acctcgaagc    840
cgtccatcat tcgtgcgcac catcatcggc tacccggccc cgaagaagca gaacacgggc    900
aagatccacg gttctgcgtt gggcgccgag gaagtcgcgg cggtgaagga agtgctcggc    960
ttcgaccccg ctaagtcctt cgacgtcgac ccggcaatcc tggcccacgc ccgtgcggca   1020
atcgaccgcg gcgcggccgc gcgtagcgaa tgggacgagt cgttccagtc ctggcaggcc   1080
gccaatccgg acgccgccgc gttgctgcga cgcatcgagg ccaggcagct tcccgacggt   1140
gtcgacgccg tcctaccggt tttcgaagcg gcaaggacg tctcgacccg tgcggcatcc   1200
ggcaaggttc tcaacgcgct cggtccggtc ctccccgaac tctggggcgg ttcggccgac   1260
ctggccgagt cgaacaacac gaccatcgag ggatcaccgt cgttcattcc ggtctcgcgt   1320
tcggcgaatg cgtggaaagg caacccgtac ggacgggttc ttcacttcgg catccgtgag   1380
cagctgccgc ggtcgatcgt caacggcatc tcgctgcacg gccccacgcg cgcgttctcc   1440
ggcacgttcc tgatcttcag tgactaccag cgcccggcca tccggctgtc cgcgctgatg   1500
ggtgtgccgt ctgtctacgt ctggtcgcac gactccatcg gcctgggtga ggatggcccg   1560
acccaccagc ccgtggaaca gctttcgacc ctgcgtgcga tccccggcct ggacgtagtc   1620
ggtcccggcg acgccaacga ggtcggcatc gcgtggaaga ccatcctgga gaaccacgag   1680
aacccggcag gagtcgtgct gacccgccag aacatcccga cctttgcccg tggcgaaggc   1740
gcagccgagg gtgacacgtt cgcatccgcg gccggggtgg cgaaaggtgg ttacgtgctg   1800
```

```
gccgaggctt cccgggacgg cgccaccgtg ccggcccagg tgctgctgat cgccaccggc   1860
tccgaggtcc aactggcggt ccaggcccga gaagcgctcc aggccgaagg catccccacc   1920
cgcgtgatct ccatgccgtg cgtcgaatgg ttcaacaagc aggacgccgc ctaccgcgag   1980
tccgtgcttc ctgccgccgt gacggcccgt gtctcggtcg aggccggatt ggccctgggc   2040
tggaaggagt tcgtcggcga cgccggacgt tcggtcagcc ttgagcactt cggggcatcg   2100
gcggattaca agcgcctgtt ccaggagttc ggcatcaccg cagacgcggt cgtcgccgcc   2160
gccaaggact ccatcaccgc ggcaggcaac taaactagta a                       2201

<210> SEQ ID NO 65
<211> LENGTH: 2133
<212> TYPE: DNA
<213> ORGANISM: Artificial Sequence
<220> FEATURE:
<223> OTHER INFORMATION: Synthesized sequence of codon-optimized Das
      gene from Pichia angusta

<400> SEQUENCE: 65
atgtctatgc gcattccgaa agctgcaagc gtaaatgacg agcagcatca gcgtatcata     60
aaatatggcc gtcgcctggt tctggacatc gttgaacagt acggtggcgg tcacccgggc    120
tccgcaatgg gcgcgatggc aattggtatc gcgctgtgga atataccct gaaatacgcg     180 ccgaacgatc cgaactactt taaccgtgat cgcttcgttc tgagcaacgg tcacgtttgc    240
ctgttccagt atattttcca gcacctgtat ggcctgaaat ctatgactat ggcacagctg    300
aaatcttatc actctaacga tttccacagc ctgtgcccgg tcacccgga aattgaacac     360 gatgcagttg aagttaccac cggtccgctg gccagggta tttctaactc tgttggcctg     420
gctatcgcga ccaaaaaacct ggcggccacc tacaacaaac cgggtttcga catcatcacc    480
aacaaagttt attgtatggt gggcgatgcg tgtctgcagg aaggtccggc actggaatct   540
atttccctgg cgggccacat gggtctggat aacctgatcg ttctgtatga taacaaccag   600
gtgtgttgcg acggcagcgt tgatattgct aacaccgaag atatcagcgc taaattcaaa   660
gcgtgtaact ggaatgtgat tgaagttgaa acgcatcgg aagatgttgc aacgatcgtg   720
aaagcgctgg aatatgccca ggctgaaaaa caccgcccta ccctaattaa ctgccgtacc   780
gttattggca gcgtgctgc tttcgaaaac cattgcgcag ctcacggcaa cgcactcggg   840
gaagatggtg ttcgcgaact caaaatcaaa tacggcatga acccggccca gaaattctat   900
attccgcagg atgtttacga tttctttaaa gaaaaccgg cggaaggtga caaactggtg   960
gcagaatgga aaagcctggt ggcgaagtac gttaaggcct atccagaaga aggtcaggaa  1020
ttccttgccc gtatgcgtgg tgaactgcct aaaaactgga atcctttttt gccgcaacag  1080
gaatttacgg gagatgcgcc gacccgcgcg cagcccgtg aactggtacg cgcgctgggt  1140
cagaattgca atcggttat cgctggctgt gctgacctgt ctgtgtctgt caatctgcag  1200
tggccaggcg ttaaatattt tatggaccca agcttatcta cccagtgtgg actgtcaggc  1260
gactatagcg acgttatat cgaatacggt atccgcgaac atgccatgtg cgcgattgcc  1320
aacggtcttg cagcgtacaa caaaggtaca tttctgccca ttacctctac ctttttcatg  1380
ttctacctct atgctgctcc ggcaatccga atggcgggcc tgcaagaatt aaaagctatc  1440
cacatcggca ctcacgactc gatcaacgag ggcgagaatg gcccgactca ccagccggtt  1500
gagtctccgg cgttatttcg cgcgatgccg aacatttatt acatgcgtcc ggtggacagc  1560
gcggaagtct tcggtctgtt ccagaaagcg gtggagctgc cattctcttc tatcctttcc  1620
```

```
ctatcgcgta acgaagtatt acagtatccg ggcaaaagct ccgccgagaa agcacagcgt    1680
ggcggctaca ttctggaaga cgctgaaaat gcggaagtgc aaattattgg tgttggcgcc    1740
gaaatggaat ttgcttacaa agctgcgaaa attctgggtc gtaagtttcg tacccgtgtg    1800
ctgtctatcc cgtgtacccg tctgtttgat gaacagagca tcggctaccg tcgttctgtg    1860
ctgcgtaaag atggccgcca ggttccgacc gtggttgtgg acggccacgt tgcgttcggc    1920
tgggaacgtt acgcgaccgc ttcctactgt atgaacacct acggtaaatc tctgccgccg    1980
gaagtaatct atgaatactt cggttataac ccggctacca tcgctaaaaa agttgaagcg    2040
tacgtacgcg catgccagcg tgatccgctg ctgctgcacg acttcctgga tctgaaagaa    2100
aaaccgaacc atgataaagt taacaaactg taa                                  2133
```

SYNTHETIC METHYLOTROPHY

INCORPORATION BY REFERENCE

The text file named "USB BIPS—LISTE DE SEQ_ST25," created on Feb. 27, 2020, and sized 241,462 bytes, which contains sequence ID listings, is herein expressly incorporated by reference.

TECHNICAL FIELD

The application relates to synthetic methylotrophy, and describes a microorganism, which has been engineered to acquire the capacity of metabolizing methanol. More particularly, the application describes a non-naturally occurring microorganism, which has been engineered to express or comprise a first enzyme and a second enzyme, wherein said first enzyme is a methanol dehydrogenase (Mdh) enzyme or a methanol oxidase (Mox) enzyme, and wherein said second enzyme is a dihydroxyacetone synthase (Das) enzyme or a transketolase enzyme.

The application also describes means and applications, more particularly kits and methods, which comprise or use said non-naturally occurring microorganism.

BACKGROUND

Methylotrophic microorganisms have the capacity to use methanol as a carbon source, i.e., the capacity to metabolize the single carbon containing methanol compound to produce energy and metabolites. Methanol is thus viewed as a substrate that may potentially be used as an alternative to sugar, with the comparative advantage of providing competitive price and sustainable supply. Methylotrophic microorganisms have therefore attracted much attention as valuable hosts for producing products of interest in an industrial setting, such as biofuels, amino acids, polymers or value-added chemicals.

Understanding how methylotrophic microorganisms achieve the conversion of methanol into carbon compounds with carbon-carbon bounds has been the focus of researches for at least the past 50 years. Methanol metabolization is generally initiated by its oxidation to formaldehyde. Formaldehyde is a highly cell toxic and is metabolized through linear or cyclic detoxification pathways or assimilated into the central carbon metabolism, e.g., via the ribulose monophosphate pathway (RuMP), the serine pathway or the xylulose monophosphate pathway (XuMP).

Reconstruction of methanol metabolic pathway has been investigated in non-native hosts, such as *Escherichia coli*. Metabolic engineering and synthetic biology have also been applied to engineer microorganisms with optimized methylotrophic pathways.

For example, in *E. coli*, methanol dehydrogenase mdh2 from *B. methanolicus* has been expressed heterologously together with 3-hexulose-6-phosphate synthase (hps) and 6-phospho-3-hexuloisomerase (phi) from *B. methanolicus*: cf. Müller et al. 2015 (Metabolic Engineering 28:190-201); cf. WO 2013/110797 in the names of SINVENT SAS et al.

However, there remains a need for microorganisms, which show improved methanol catabolization, more particularly improved growth on methanol as a main or sole source of carbon and energy.

SUMMARY

The application describes a non-naturally occurring microorganism, which comprises, is expressing, or has been engineered to comprise or express a first enzyme and a second enzyme, wherein said first enzyme is an alcohol dehydrogenase (Ald) enzyme or alcohol oxidase (Alo) enzyme, more particularly a methanol dehydrogenase (Mdh) enzyme or a methanol oxidase (Mox) enzyme, more particularly a Mdh enzyme, more particularly a NAD-dependent Mdh enzyme, and said second enzyme is a dihydroxyacetone synthase (Das) enzyme or a transketolase enzyme, more particularly a Das enzyme.

At least one or each of said first and second enzymes is heterologous to said microorganism.

The non-naturally occurring microorganism allows methanol to be metabolized into compounds with carbon-carbon bonds.

The application further relates to means and applications, which comprise or use said non-naturally occurring microorganism. The application notably describes a method of in vitro production of a compound, more particularly of a compound of industrial interest, wherein said compound is produced as a metabolite of said non-naturally occurring microorganism. The application also describes kits, cell cultures and cell culture media, which comprise at least one non-naturally occurring microorganism.

Figure 1:
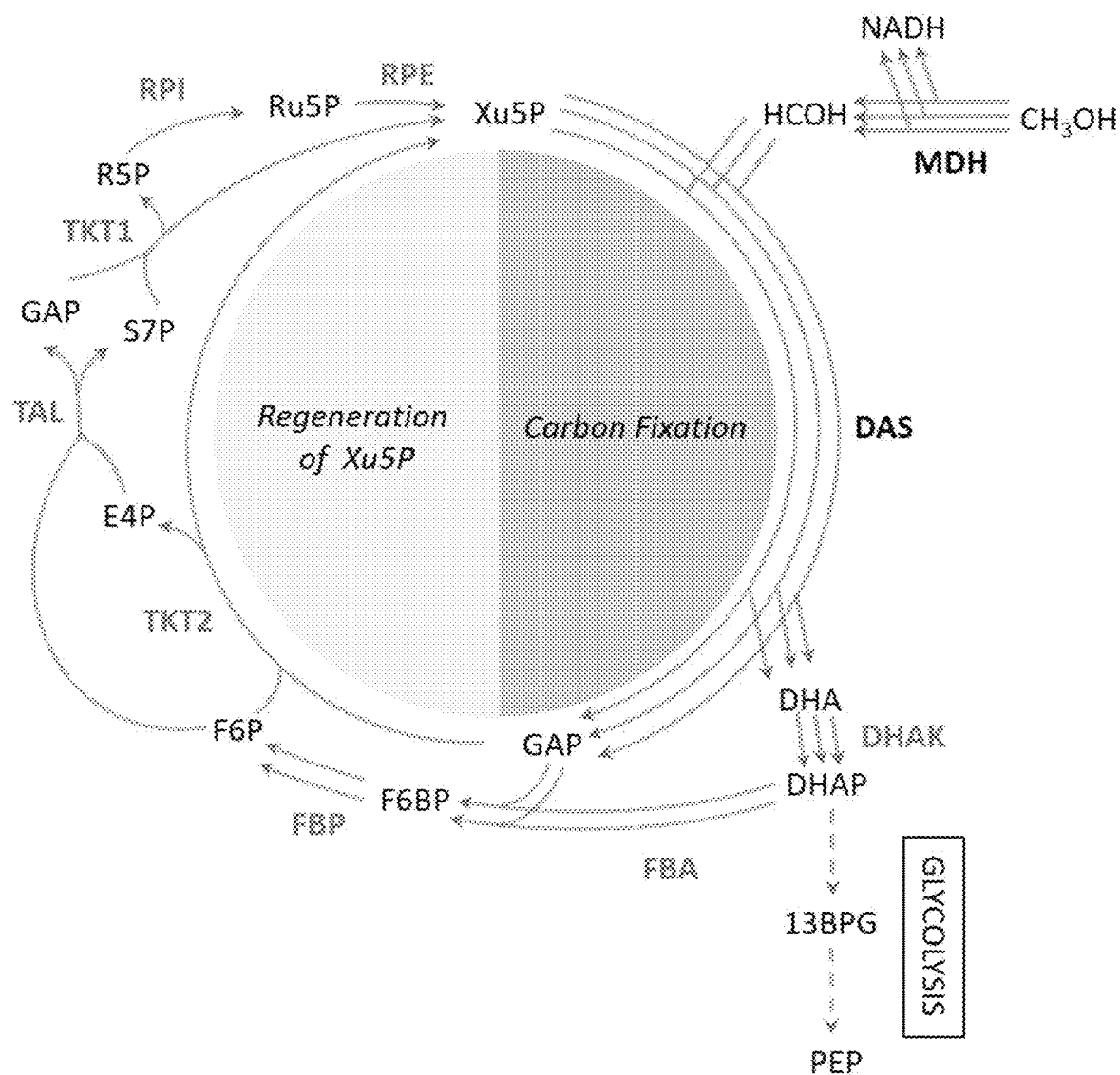
FIG. 1: example of metabolic pathway, which may be involved in methanol assimilation in *E. coli* strain recombinantly expressing Mdh and Das enzymes.

Metabolites: MeOH Methanol; HCOH Formaldehyde; DHA Dihydroxyacetone; DHAP Dihydroxyacetone phosphate; 13BPG 1,3-bisphosphoglycerate; PEP phosphoenolpyruvate; GA3P glyceraldehyde 3 phosphate; F6P fructose 6 phosphate; Xu5P xylulose 5 phosphate; E4P erythrose 4 phosphate; S7P sedoheptulose 7 phosphate; R5P ribose 5 phosphate; Ru5P ribulose 5 phosphate.

Enzymes: MDH NAD-dependent methanol dehydrogenase; DAS dihydroxyacetone synthase; DHAK dihydroxyacetone kinase; FBA fructose bisphosphate aldolase; FBP Fructose 1,6 bisphosphatase; TKT2 transketolase 2; TKT1 transketolase 1; TAL transaldolase; RPI Ribose 5 phosphate isomerase; RPE ribulose 5 phosphate 3 epimerase.

Figure 2:
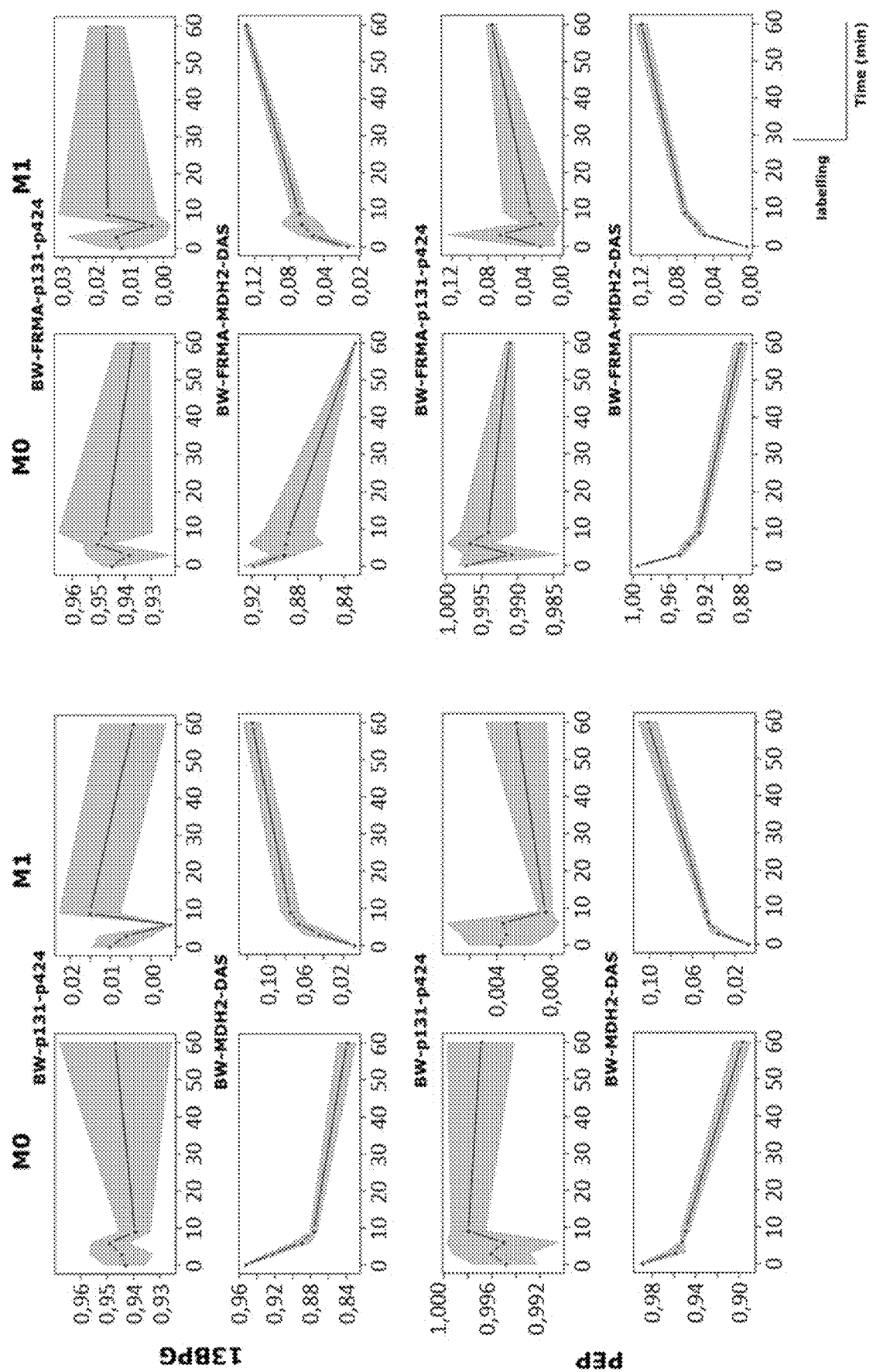

FIG. 2: mass isotopomer fractions of metabolites before (i.e., time zero point) and after (i.e., 3, 6, 10, 30 and 60 min time points) addition of 13C methanol in cultures of recombinant *E. coli*.

M0=fraction of the molecules wherein zero carbon atom is 13C-labeled

M1=fraction of the molecules wherein one carbon atom is 13C-labeled

Average and standard deviation (gray shading) of 3 replicates per condition is shown.

13BPG=1,3 bisphosphoglycerate

PEP=phosphoenolpyruvate

BW-MDH2-DAS=*E. coli* recombinantly expressing Mdh2 (from *B. methanolicus*; amino acid sequence of SEQ ID NO: 1) and Das (from *P. angusta*; amino acid sequence of SEQ ID NO: 15)

BW-p131-p134=control *E. coli* with empty plasmids

BW-FRMA-MDH2-DAS=*E. coli* recombinantly expressing Mdh2 (from *B. methanolicus*) and Das and lacking the formaldehyde dehydrogenase gene (from *P. angusta*).

Figure 3:
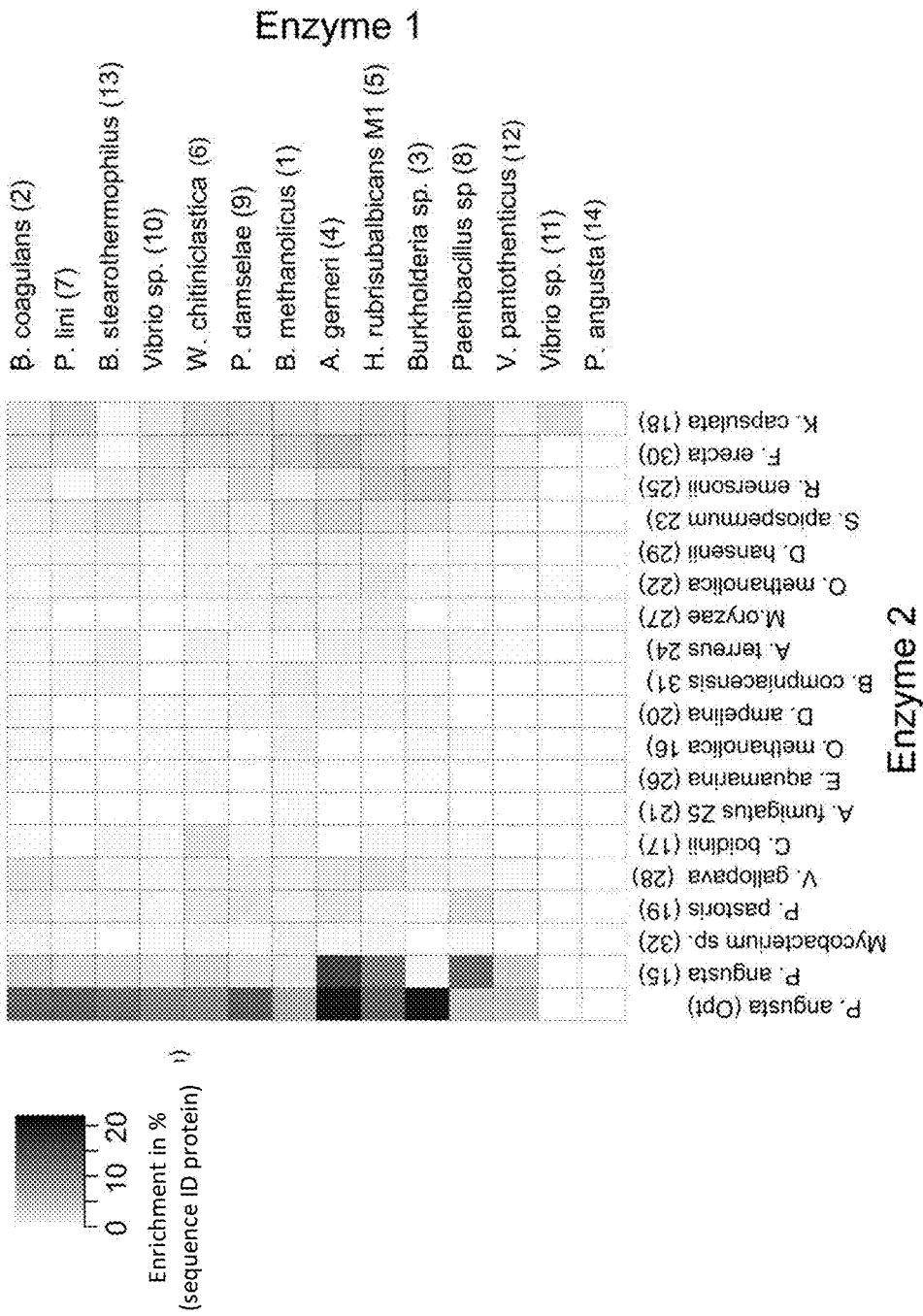

BW-FRMA-p131-p134=control *E. coli* with empty plasmids and lacking the formaldehyde dehydrogenase gene FIG. 3: Mean Isotopic enrichment of the phosphoenolpyruvate after 90 minutes addition of 13c methanol in cultures of recombinant *E. coli*. The mean isotopic enrichment is express in % and has been calculated as follow: (0*M0+1*M1+2*M2+3*M3)/3. For each enzyme, the source of the microorganism and the number of the protein sequence according to the table 1 are given in bracket.

Figure 4:
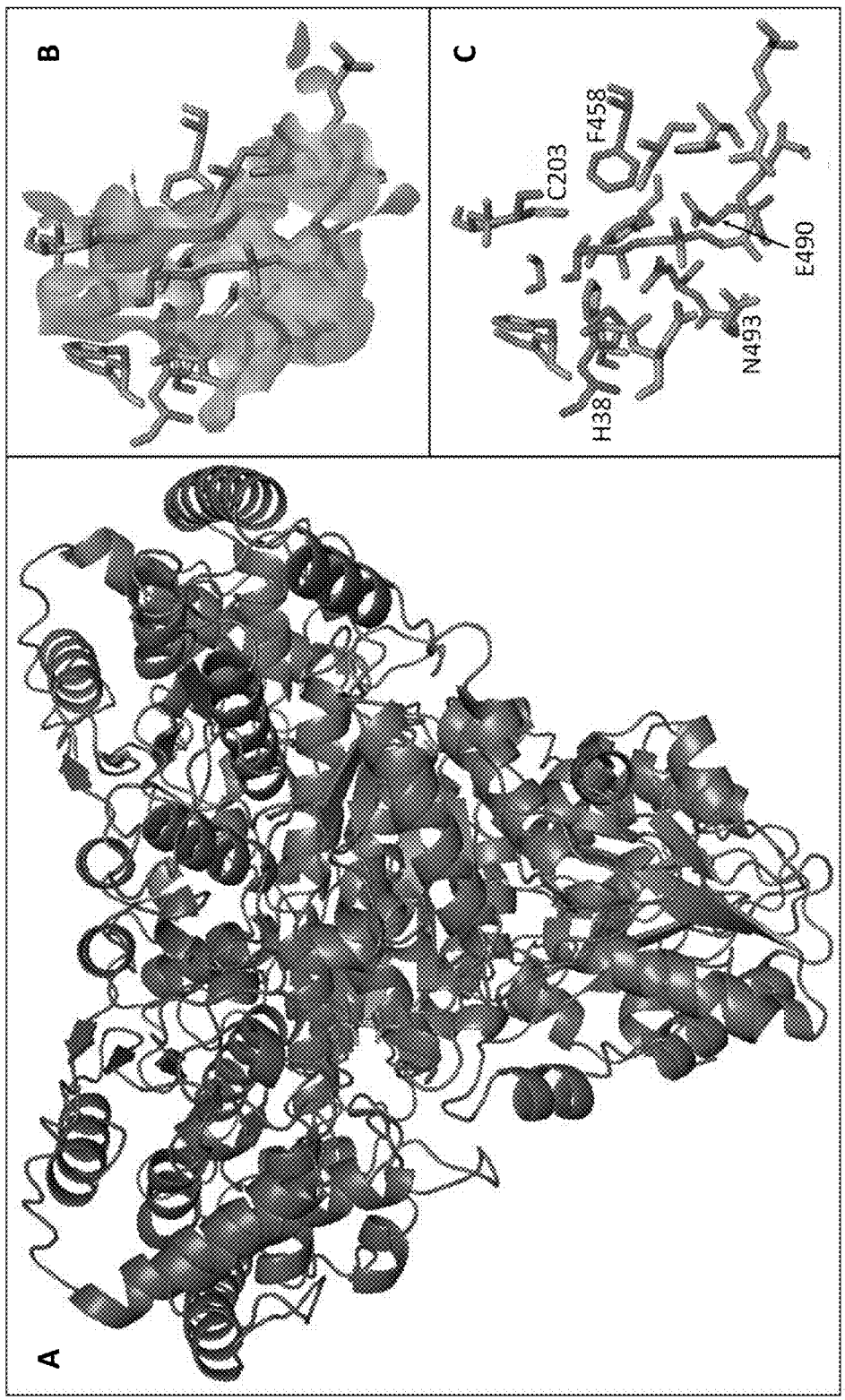

FIG. 4: DAS model resulting from I-TASSER. A: Homodimeric structure of DAS with the position of the X5P (yellow); B: X5P in the catalytic site of DAS. The amino acids represented are within 5 Å of X5P. The electrostatic surface of those amino acids is also represented; C: amino acids not conserved within the DAS phylogeny and within 5 Å of X5P, and H38 are highlighted in orange and labelled.

DETAILED DESCRIPTION

The application describes a non-naturally occurring microorganism, as well as means and applications, more particularly biotechnological means and applications, which comprise or use said non-naturally occurring microorganism.

The non-naturally occurring microorganism of the application allows methanol to be metabolized into compounds with carbon-carbon bonds. In other words, the non-naturally occurring microorganism of the application is a methylotrophic microorganism.

More particularly, the non-naturally occurring microorganism of the application has been engineered to allow or acquire methylotrophy.

More particularly, the non-naturally occurring microorganism of the application has been modified by genetic engineering and/or metabolic engineering to allow or acquire methylotrophy.

In other words, the non-naturally occurring microorganism of the application is a synthetic methylotroph.

The term "methylotrophy" is intended in accordance with its ordinary meaning in the field. Methylotrophy generally relates to the capacity of certain microorganisms (mostly bacteria and yeasts) to use reduced molecules without C—C bond (also referred to as one-carbon (C1) compounds) as their sole source of carbon and energy. The C1 compounds used by natural methylotrophs may include methane and methanol, and also methylamines, di-, tri- and tetra-methylamine, formate, formamide, chloromethane and dichloromethane. While bacterial methylotrophs typically are capable of growing on a variety of C1 compounds—with the exception of methanotrophs, which are mostly dedicated to methane conversion—eukaryotic methylotrophs are generally restricted to growth with methanol as C1 source.

The general view is that a methylotroph (aerobically) utilizes methanol by oxidizing it to yield formaldehyde, which in turn can either be used for energy and/or for production of metabolites, such as phosphoenolpyruvate (PEP) [cf. the example of metabolic diagram that is shown on FIG. 1]. Methylotrophy can thus be viewed as the capacity of metabolizing methanol (to produce energy and/or metabolites, such as PEP).

A methylotrophic microorganism may or may not grow on methanol (e.g., as sole carbon source), i.e., the number of cells of said microorganism may or may not increase. However, a methylotrophic microorganism metabolizes methanol (and produces metabolite(s), such as PEP).

The non-naturally occurring microorganism of the application comprises, or is expressing, or has been engineered to comprise or express:
- a first enzyme, which is an alcohol dehydrogenase (Ald) enzyme or alcohol oxidase (Alo) enzyme, more particularly a methanol dehydrogenase (Mdh) enzyme or a methanol oxidase (Mox) enzyme, more particularly a Mdh enzyme, more particularly a NAD-dependent Mdh enzyme, and
- a second enzyme, which is a dihydroxyacetone synthase (Das) enzyme or a transketolase enzyme, more particularly a Das enzyme.

The terms "alcohol dehydrogenase" (Ald), "alcohol oxidase" (Alo), "methanol dehydrogenase" (Mdh), "methanol oxidase" (Mox), "NAD-dependent methanol dehydrogenase" (NAD-dependent Mdh), "dihydroxyacetone synthase" (Das), "transketolase" are herein intended in accordance with their respective ordinary meanings in the field.

Schematically, the term "alcohol dehydrogenase" (Ald) refers to enzyme entry EC 1.1.1.1, i.e., an enzyme that catalyzes the reaction alcohol+NAD(⁺) or NADP(+)<=>aldehyde or ketone+NADH or NADPH.

Schematically, the term "alcohol oxidase" (Alo) refers to enzyme entry EC 1.1.3.13, i.e., an alcohol: oxygen oxidoreductase, i.e., an enzyme that catalyzes the reaction (primary) alcohol+O₂<=>aldehyde+H₂O₂ wherein FAD may act as a cofactor.

Schematically, the term "methanol dehydrogenase" (Mdh) refers to an enzyme that catalyzes the reaction methanol+NAD(⁺) or NADP(⁺)<=>formaldehyde+ NADH or NADPH, more particularly methanol+NAD (⁺)<=>formaldehyde+NADH.

A methanol dehydrogenase may be enzymatically active not only on methanol, but also on alcohol substrates other than methanol, e.g., on ethanol.

Schematically, the term "methanol oxidase" (Mox) refers to an enzyme that catalyzes the reaction methanol+O₂<=>formaldehyde+H₂O₂ wherein FAD may act as a cofactor.

Schematically, the term "NAD-dependent methanol dehydrogenase" (NAD-dependent Mdh) refers to enzyme entry EC 1.1.1.244, i.e., an enzyme which catalyzes the reaction methanol+NAD(⁺)<=>formaldehyde+NADH, but which cannot catalyze the reaction methanol+NADP(⁺)<=>formaldehyde+NADPH.

Schematically, the term "dihydroxyacetone synthase" (Das) refers to enzyme entry EC 2.2.1.3, i.e., D-xylulose-5-phosphate: formaldehyde glycolaldehydetransferase, i.e., an enzyme that catalyzes the reaction D-xylulose 5-phosphate+formaldehyde<=>D-glyceraldehyde 3-phosphate+dihydroxyacetone, wherein thiamine diphosphate may act as a cofactor.

Schematically, the term "transketolase" refers to enzyme entry EC 2.2.1.1, i.e., sedoheptulose-7-phosphate: D-glyceraldehyde-3-phosphate glycolaldehydetransferase, i.e., an enzyme that catalyzes the transfer of a two-carbon ketol group from a ketose donor to an aldose acceptor, via a covalent intermediate with the cofactor thiamine pyrophosphate.

The non-naturally occurring microorganism of the application may show improved energetic efficiency, more particularly improved ATP efficiency, compared to prior art microorganisms, such as an *E. coli* microorganism, which does not express said second enzyme (e.g., the Das enzyme), but which has been engineered to express *B. methanolicus* Mdh, Hps and Phi enzymes (as described e.g., in Müller et al. 2015 (Metabolic Engineering 28:190-201); cf. WO 2013/110797 in the names of SINVENT SAS et al.).

In addition, the proposed metabolic pathway allows regeneration of C1 acceptor (i.e., xylulose-5-phosphate) independently of pentose phosphate pathway activity. This has been identified as a major bottleneck in the microorganisms which has been engineered to express *B. methanolicus* Mdh, Hps and Phi enzymes.

At least one of said first and second enzymes is heterologous to said microorganism.

Alternatively or complementarily, at least one of said first and second enzymes is recombinantly expressed in said microorganism.

For example:
said first enzyme is recombinantly expressed and/or heterologous to said microorganism, more particularly is heterologous to said microorganism;
and/or, more particularly and,
said second enzyme is recombinantly expressed and/or heterologous to said microorganism, more particularly is heterologous to said microorganism.

More particularly, each of said first and second enzymes is heterologous to said microorganism (and optionally at least one or each of said first and second enzymes is recombinantly expressed).

The term "recombinant" is herein intended in accordance with its ordinary meaning in the field. It notably refers to nucleic acids or proteins, which have been engineered by man and/or which are not naturally occurring. For example, a plasmid or a chromosome, which has been engineered to carry and express a nucleic acid coding sequence, is a recombinant nucleic acid.

An enzyme is recombinantly expressed for example when the nucleic acid molecule which codes for the enzyme is a recombinant nucleic acid (e.g., a plasmid or chromosome into which the nucleic acid coding for the enzyme has been inserted for protein expression).

The term "heterologous" is herein intended in accordance with its ordinary meaning in the field. Schematically, a first biological entity is heterologous to a second biological entity when said first and second biological entities do not naturally occur together in the same biological life form.

Therefore, an enzyme is generally considered heterologous to a microorganism when there is no naturally-occurring form of said microorganism, which would comprise or express said enzyme.

For example:
an enzyme, which is a yeast enzyme or which originates from a yeast (e.g., a Das enzyme from a *Pichia* yeast) is heterologous to a microorganism, which is a bacterium (e.g., *E. coli*) [provided of course that said bacterium does not naturally comprise the same (Das) enzyme as said (*Pichia*) yeast];
an enzyme, which is a yeast enzyme or which originates from a yeast (e.g., a Das enzyme from a *Pichia angusta* yeast) is heterologous to a microorganism, which is a yeast that belongs to another yeast strain, species or genus (e.g., to a microorganism, which is a yeast that belongs to a *Pichia* species other than *P. angusta* or to a yeast genus other than *Pichia*, e.g., to a microorganism, which is a *Saccharomyces cerevisiae* yeast) [provided of course that said yeast that belongs to another yeast strain, species or genus (e.g., said *S. cerevisiae*) does not naturally comprise the same (Das) enzyme as said (*P. angusta*) yeast];
an enzyme, which is a bacterial enzyme or which originates from a bacterium (e.g., a Mdh enzyme from a *Bacillus* bacterium) is heterologous to a microorganism, which is a yeast (e.g., *S. cerevisiae*) [provided of course that said yeast does not naturally comprise the same (Mdh) enzyme as said (*Bacillus*) bacterium];
an enzyme, which is a bacterial enzyme or which originates from a bacterium (e.g., a Mdh enzyme from a *Bacillus methanolicus* bacterium) is heterologous to a microorganism, which is a bacterium that belongs to another strain, species or genus (e.g., to a microorganism, which is a bacterium that belongs to a genus other than *Bacillus* or to a species other than *B. methanolicus*, e.g., to a microorganism which is a *Bacillus subtilis* bacterium) [provided of course that said bacterium that belongs to another strain, species or genus (e.g., said *B. subtilis* bacterium) does not naturally comprise the same (Mdh) enzyme as said (*B. methanolicus*) bacterium)].

The fact that an enzyme is heterologous to a microorganism implies that the microorganism is heterologous to said enzyme.

Similarly, a first enzyme is heterologous to a second enzyme, when there is no naturally-occurring form of microorganism, which would comprise or express both said first and second enzymes. Said first and second enzymes may e.g., originate from different biological strains, species or genera.

For example, an enzyme, which is a bacterial enzyme or which originates from a bacterium (e.g., a Mdh enzyme from a *Bacillus* bacterium), is heterologous to an enzyme, which is a yeast enzyme or which originates from a yeast (e.g., a Das enzyme from a *Pichia* yeast) [provided of course that said bacterial enzyme and said yeast enzyme are not naturally comprised or expressed in the same naturally-occurring microorganism].

Thus, it can be considered that an enzyme, which is a bacterial enzyme or which originates from a bacterium (e.g., a Mdh enzyme from a *Bacillus methanolicus* bacterium), is heterologous to an enzyme, which is a yeast enzyme or which originates from a yeast (e.g., a Das enzyme from a *Pichia* yeast), and that both said bacterial enzyme and said yeast enzyme are heterologous to a microorganism, which is chosen from among the *Escherichia* bacteria (more particularly *Escherichia coli*), the *Corynebacterium* bacteria (more particularly *C. glutanicum*), the *Bacillus* bacteria other than *B. methanolicus* (more particularly *B. subtilis*), the *Saccharomyces* yeasts (more particularly *S. cerevisiae*) and the *Yarrowia* fungi (more particularly *Yarrowia lipolytica*).

The combination or association of said first and second enzymes (i.e., the combination or association of said Ald or Alo enzyme and of said Das or transketolase enzyme, e.g., of said Ald and Das enzymes, e.g., of said Mdh and Das enzymes) allows methanol to be metabolized into one or several compounds, which each have carbon-carbon bond (s). Said carbon-carbon bond(s) may e.g., be single bond(s). The phrase "compounds with carbon-carbon bond(s)" is intended in accordance with its ordinary meaning in the field. It notably encompasses compounds, which each comprise at least two carbon atoms (e.g., three carbon atoms), wherein said at least two carbon atoms (e.g., said three carbon atoms) are linked together by a covalent bond (e.g., each of said three carbon atoms is linked by a covalent bond to one or at least one of the two other carbon atoms).

Said microorganism may comprise any cofactor, which may be useful for the catalytic activity of said first or second enzyme. For example, said microorganism may comprise (or produce) thiamine diphosphate when said second enzyme is a Das enzyme.

Said first and second enzymes confers methylotrophy to said non-naturally occurring microorganism, or allows methylotrophy in said non-naturally occurring microorganism.

Said microorganism may grow or not grow on methanol (e.g., as sole carbon source). Said microorganism does however produce metabolite(s) from methanol (e.g., PEP).

Said first enzyme i.e., said Ald or Alo enzyme, more particularly said Mdh or Mox enzyme, more particularly said Mdh enzyme, more particularly said NAD-dependent Mdh enzyme) may allow conversion of methanol ($CH_3OH$) into formaldehyde (HCOH).

Said second enzyme (i.e., said Das or transketolase enzyme, more particularly said Das enzyme) may allow for incorporation of a C1 compound, more particularly of formaldehyde, into a C5 compound such as xylulose 5-phosphate (Xu5P). Said second enzyme may allow for incorporation of formaldehyde into Xu5P to produce dihydroxyacetone (DHA) and glyceraldehyde 3-phosphate (GA3P). Said second enzyme may allow for production of DHA from formaldehyde.

A non-naturally occurring microorganism, which has been engineered to acquire methylotrophy, wherein said microorganism comprises a first enzyme and a second enzyme, wherein said first enzyme is a methanol dehydrogenase (Mdh) enzyme or a methanol oxidase (Mox) enzyme, wherein said second enzyme is a dihydroxyacetone synthase (Das) enzyme or a transketolase enzyme, and wherein at least one of said first and second enzymes is heterologous to said microorganism.

The application describes more particularly a non-naturally occurring microorganism, which has been (genetically and/or metabolically) engineered to allow or acquire methylotrophy, wherein said microorganism comprises, or is expressing, or has been engineered to comprise or express:
 a first enzyme, which has been selected from microorganisms growing in a range from 10 to 60° C., and
 a second enzyme, which has been selected from microorganisms growing in a range from to 50° C. (see Table 1),
wherein the optimum temperature of some combinations of said first and second enzymes is quiet distant.

The application describes more particularly a non-naturally occurring microorganism herein defined, wherein the optimal activity temperature of said first enzyme and the optimal activity temperature of said second enzyme differ by at most 10° C., in particular by at most 5° C. and more particularly by at most 1° C.

More particularly, the optimal activity temperature of said first enzyme and the optimal activity temperature of said second enzyme differ by at most 9° C., 8° C., 7° C., 6° C., 5° C., 4° C., 3° C., 2° C., 1,5° C., 1° C., 0.9° C., 0.7° C., 0.5° C., 0.3° C. or 0.1° C.

The application describes more particularly a non-naturally occurring microorganism herein defined, wherein the optimal activity temperature of said first enzyme and the optimal activity temperature of said second enzyme are the same.

The application describes more particularly a non-naturally occurring microorganism herein defined, wherein the optimal activity temperature of said first enzyme and the optimal activity temperature of said second enzyme are from 10 to 60° C., in particular from 20 to 50° C., more particularly from 35 to 45° C.

More particularly, the optimal activity temperature of said first enzyme and the optimal activity temperature of said second enzyme are from 15 to 55° C., in particular from 25 to 45° C., more particularly from 30 to 40° C. More particularly, the optimal activity temperature of said first enzyme and the optimal activity temperature of said second enzyme are 10, 15, 20, 25, 30, 35, 36, 37, 38, 39, 40, 41, 42, 43, 44, 45, 50, 55 or 60° C.

The application describes more particularly a non-naturally occurring microorganism herein defined,
 wherein the optimal activity temperature of said first enzyme and the optimal activity temperature of said second enzyme are from 10 to 60° C., in particular from 20 to 50° C., more particularly from 35 to 45° C., and
 wherein the optimal activity temperature of said first enzyme and the optimal activity temperature of said second enzyme differ by at most 10° C., in particular by at most 5° C. and more particularly by at most 1° C.

The application describes more particularly a non-naturally occurring microorganism herein defined,
 wherein the optimal activity temperature of said first enzyme and the optimal activity temperature of said second enzyme are from 10 to 60° C., in particular from 20 to 50° C., more particularly from 35 to 45° C., and
 wherein the optimal activity temperature of said first enzyme and the optimal activity temperature of said second enzyme are the same.

The application describes more particularly a non-naturally occurring microorganism, which has been (genetically and/or metabolically) engineered to allow or acquire methylotrophy, wherein said microorganism comprises, or is expressing, or has been engineered to comprise or express:
 a first enzyme, which is a methanol dehydrogenase (Mdh) enzyme or a methanol oxidase (Mox) enzyme, more particularly a Mdh enzyme, more particularly a NAD-dependent Mdh enzyme,
 a second enzyme, which is a dihydroxyacetone synthase (Das) enzyme or a transketolase enzyme, more particularly a Das enzyme, as well as
wherein at least one of said first and second enzymes is recombinantly expressed and/or heterologous to said microorganism, more particularly is heterologous to said microorganism.

More particularly, each of said first and second enzymes is recombinantly expressed and/or heterologous to said microorganism (independently from each other).

More particularly, each of said first and second enzymes is heterologous to said microorganism (independently from each other).

Said first enzyme and said second enzyme may be heterologous to each other (i.e., there is no naturally-occurring microorganism, which would express both said first and second enzymes).

Alternatively, said first enzyme and said second enzyme may be not heterologous to each other, i.e., they may be autologous (i.e., there is a naturally-occurring microorganism, which expresses both said first enzyme and said second enzyme).

Said first enzyme may e.g., be a Mdh or Mox enzyme, more particularly a Mdh enzyme, more particularly a NAD-dependent Mdh enzyme, the amino acid sequence of which comprises:
   any one of SEQ ID NOs: 1-14, or
   an amino acid sequence, which is at least 50% identical to a sequence chosen from among SEQ ID NOs: 1-14.

Said first enzyme may e.g., be a Mdh enzyme, more particularly a NAD-dependent Mdh enzyme, the amino acid sequence of which comprises:
   any one of SEQ ID NOs: 1-13, or
   an amino acid sequence, which is at least 50% identical to a sequence chosen from among SEQ ID NOs: 1-13.

Said first enzyme may e.g., be a Mdh or Mox enzyme, more particularly a Mdh enzyme, more particularly a NAD-dependent Mdh enzyme, the amino acid sequence of which comprises:
   any one of SEQ ID NOs: 1-4, or
   an amino acid sequence, which is at least 50% identical to a sequence chosen from among SEQ ID NOs: 1-4.

Said first enzyme may e.g., be a Mdh or Mox enzyme, more particularly a Mdh enzyme, more particularly a NAD-dependent Mdh enzyme, the amino acid sequence of which comprises:
   SEQ ID NO: 1 or 2, or
   an amino acid sequence, which is at least 50% identical to a sequence chosen from among SEQ ID NOs: 1-2.

Said first enzyme may e.g., be a Mdh or Mox enzyme, more particularly a Mdh enzyme, more particularly a NAD-dependent Mdh enzyme, the amino acid sequence of which comprises:
   SEQ ID NO: 1, or
   an amino acid sequence, which is at least 50% identical to SEQ ID NO: 1.

The enzyme, the amino acid sequence of which is at least 50% identical to SEQ ID NO: 1, may e.g., be or comprise a sequence from among SEQ ID NOs: 2-14, more particularly from among SEQ ID NOs: 2-13, more particularly from among SEQ ID NOs: 2-4, more particularly SEQ ID NO: 2.

Said first enzyme has retained a Mdh or Mox activity, more particularly a Mdh activity, more particularly a NAD-dependent Mdh activity, more particularly the capacity to catalyze the reaction

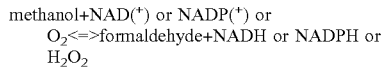

more particularly

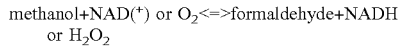

more particularly

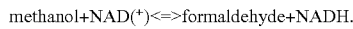

The enzyme, the amino acid sequence of which is at least 50% identical to SEQ ID NO: 1, may be an enzyme, the amino acid sequence length of which differs from the length of SEQ ID NO: 1, by e.g., plus or minus 70 nucleotides, e.g., plus or minus 60 nucleotides, e.g., plus or minus 50 nucleotides, e.g., plus or minus 40 nucleotides, e.g., plus or minus 30 nucleotides, e.g., plus or minus 20 nucleotides, e.g., plus or minus 10 nucleotides, e.g., plus or minus 5 nucleotides, e.g., by plus or minus 5 nucleotides.

The amino acid sequence of said first enzyme may consist of e.g., 330-460 amino acids (e.g., of 339-453 amino acids, e.g., of 376-453 amino acids), e.g., of 339-390 amino acids, e.g., of 382-390 amino acids, e.g., of 382, 384, 385, 386, 389, or 390 amino acids, e.g., of 385 or 386 amino acids, e.g., of 385 amino acids.

Said first enzyme may be e.g., a (Ald or Alo, more particularly a Mdh or Mox, more particularly a Mdh, more particularly a NAD-dependent Mdh) enzyme from a bacterium, a yeast or a fungus, more particularly from a bacterium. Said first enzyme may e.g., be a bacterial enzyme, which is not naturally comprised or expressed in yeast or fungus.

Said bacterial enzyme may e.g., be an (Ald or Alo, more particularly a Mdh or Mox, more particularly a Mdh, more particularly a NAD-dependent Mdh) enzyme from a bacterium chosen in the following list of bacteria:
   *Bacillus,*
   *Burkholderia,*
   *Acinetobacter,*
   *Herbaspirillum,*
   *Wohlfahrtiimonas,*
   *Pseudomonas,*
   *Paenibacillus,*
   *Photobacterium,*
   *Vibrio,*
   *Virgibacillus,* and
   *Geobacillus.*

Said bacterial enzyme may e.g., be an (Ald or Alo, more particularly a Mdh or Mox, more particularly a Mdh, more particularly a NAD-dependent Mdh) enzyme from a bacterium chosen in the following list of bacteria:
   *Bacillus methanolicus* (more particularly strain PB1 or strain MGA3),
   *Bacillus coagulans* (more particularly strain 36D1),
   *Burkholderia* sp. TSV86,
   *Acinetobacter gerneri* (more particularly strain DSM 14967 or CIP 107464),
   *Herbaspirillum rubrisubalbicans* (more particularly strain M1),
   *Wohlfahrtiimonas chitiniclastica* (more particularly strain SH04).
   *Pseudomonas lini,*
   *Paenibacillus* sp. IHB B 3084,
   *Photobacterium damselae* (more particularly *Photobacterium damselae* subsp. damselae, more particularly strain CIP 102761),
   *Vibrio* sp. ER1A,
   *Virgibacillus pantothenticus,* and
   *Geobacillus stearothermophilus* (*Bacillus stearothermophilus*).

More particularly, said bacterial enzyme may e.g., be an (Ald or Alo, more particularly a Mdh or Mox, more particularly a Mdh, more particularly a NAD-dependent Mdh) enzyme from *Bacillus*, more particularly *Bacillus methanolicus* or *Bacillus coagulans*, more particularly *Bacillus methanolicus*.

*B. methanolicus* strain PB1 is available under NCIMB 13113. Nucleic acid and protein sequences of *B. methanolicus* strain PB1 have been described in WO 2013/110797 in the names of SINVENT AS et al. (cf. the nucleic acid sequences of SEQ ID NO: 1, 3, 5, 7, 9 and 11 in WO 2013/110797 and the amino acid sequences of SEQ ID NO: 2, 4, 6, 8, 10 and 12 in WO 2013/110797).

*B. methanolicus* strain MGA3 is available under ATCC 53907.

More particularly, said first enzyme may e.g., be:
   a *Bacillus* NAD-dependent Mdh enzyme, more particularly a *Bacillus methanolicus* NAD-dependent Mdh enzyme, more particularly the *Bacillus methanolicus* NAD-dependent Mdh enzyme of SEQ ID NO: 1, or of a bacterial enzyme, wherein the amino acid sequence of said bacterial enzyme comprises a sequence from among SEQ ID NOs: 2-14 (more particularly a sequence from among SEQ ID NOs: 2-13, more particularly a sequence from among SEQ ID NOs: 2-4, more particularly the sequence of SEQ ID NO: 2), and wherein said bacterial enzyme has retained a Mdh or Mox activity, more particularly a Mdh activity.

The amino acid sequence of said first enzyme may consist of e.g., 330-460 amino acids (e.g., of 339-453 amino acids, e.g., of 376-453 amino acids), e.g., of 339-390 amino acids, e.g., of 382-390 amino acids, e.g., of 382, 384, 385, 386, 389, or 390 amino acids, e.g., of 385 or 386 amino acids, e.g., of 385 amino acids.

Said bacterial enzyme may e.g., an enzyme from one of the above-captioned lists of bacteria.

Said first enzyme may be e.g., a (Ald or Alo, more particularly a Mdh or Mox, more particularly a Mdh, more particularly a NAD-dependent Mdh) enzyme, which is activated or stimulated by the endogenous activator protein Act, or which is not activated and not stimulated by Act.

Said second enzyme may e.g., be a Das or transketolase enzyme, the amino acid sequence of which comprises:
any one of SEQ ID NOs: 15-32, or
an amino acid sequence, which is at least 50% identical to a sequence chosen from among SEQ ID NOs: 15-32.

Said second enzyme may e.g., a Das or transketolase enzyme, the amino acid sequence of which comprises:
any one of SEQ ID NOs: 15-18, or
an amino acid sequence, which is at least 50% identical to a sequence chosen from among SEQ ID NOs: 15-18.

Said second enzyme may e.g., a Das or transketolase enzyme, the amino acid sequence of which comprises:
any one of SEQ ID NOs: 15-16, or
an amino acid sequence, which is at least 50% identical to a sequence chosen from among SEQ ID NOs: 15-16.

Said second enzyme may e.g., be:
a *Pichia* Das enzyme, more particularly a *Pichia angusta* Das enzyme, more particularly the *Pichia angusta* Das enzyme of SEQ ID NO: 15; or
an enzyme, the amino acid sequence of which is at least 50% identical to SEQ ID NO: 15. Said second enzyme may e.g., be a Das or transketolase enzyme, the amino acid sequence of which comprises:
SEQ ID NO: 15, or
an amino acid sequence, which is at least 50% identical to SEQ ID NO: 15.

The enzyme, the amino acid sequence of which is at least 50% identical to SEQ ID NO: 15, may e.g., be or comprise a sequence from among SEQ ID NOs: 16-32, more particularly from among SEQ ID NOs: 16-18, more particularly the sequence of SEQ ID NO: 16.

Said second enzyme has retained a Das or transketolase activity, more particularly a Das activity, more particularly the capacity to catalyze the following reaction:

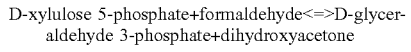

D-xylulose 5-phosphate+formaldehyde<=>D-glyceraldehyde 3-phosphate+dihydroxyacetone (wherein thiamine diphosphate may act as a cofactor).

The enzyme, the amino acid sequence of which is at least 50% identical to SEQ ID NO: 15, may be an enzyme, the amino acid sequence length of which differs from the length SEQ ID NO: 15, by e.g., plus or minus 200 nucleotides, e.g., plus or minus 100 nucleotides, e.g., plus or minus 50 nucleotides, e.g., plus or minus 30 nucleotides, e.g., by plus or minus 20 nucleotides, e.g., by plus or minus 10 nucleotides, e.g., by plus or minus 4 nucleotides.

The amino acid sequence of said second enzyme may consist of e.g., 618-875 amino acids, e.g., 700-810 amino acids (e.g., 703-808 amino acids), e.g., 700-760 amino acids (e.g., 703-754 amino acids), e.g., of 705-710 amino acids, e.g., of 705, 706, 707, 709 or 710 amino acids, e.g., of 710 amino acids.

TABLE 1

| SEQ ID NOS: | | | | Growth |
|---|---|---|---|---|
| Protein | Nucleic Acid | Protein names | Source organism | temperature (° C.) |
| 1 | 33 | Methanol dehydrogenase 2 (EC 1.1.1.244) | *Bacillus methanolicus* PB1 | 50-53 |
| 2 | 34 | Alcohol dehydrogenase | *Bacillus coagulans* | 30-55 |
| 3 | 35 | Lactaldehyde reductase | *Burkholderia* sp. TSV86 | 30-35 |
| 4 | 36 | Uncharacterized protein | *Acinetobacter gerneri* DSM 14967 = CIP 107464 | 30-41 |
| 5 | 37 | Iron-containing alcohol dehydrogenase protein | *Herbaspirillum rubrisubalbicans* M1 | 30 |
| 6 | 38 | Uncharacterized protein | *Wohlfahrtiimonas chitiniclastica* | 28-37 |
| 7 | 39 | Alcohol dehydrogenase | *Pseudomonas lini* | 30-35 |
| 8 | 40 | Lactaldehyde reductase | *Paenibacillus* sp. IHB B 3084 | 10-40 |
| 9 | 41 | Alcohol dehydrogenase | *Photobacterium damselae* subsp. *damselae* (*Listonella damsela*) | 25-37 |
| 10 | 42 | Alcohol dehydrogenase | *Vibrio* sp. ER1A | 30 |
| 11 | 43 | Alcohol dehydrogenase | *Vibrio* sp. ER1A | 30 |
| 12 | 44 | 1,2-propanediol oxidoreductase | *Virgibacillus pantothenticus* | 15-50 |
| 13 | 45 | Alcohol dehydrogenase (ADH) (EC 1.1.1.1) | *Geobacillus stearothermophilus* (*Bacillus stearothermophilus*) | 40-60 |
| 14 | 46 | Alcohol oxidase (AO) (AOX) (EC 1.1.3.13) (Methanol oxidase) (MOX) | *Pichia angusta* (Yeast) (*Hansenula polymorpha*) | 15-50 |
| 15 | 47, 65* | Dihydroxyacetone synthase (DHAS) (EC 2.2.1.3) (Formaldehyde transketolase) (Glycerone synthase) | *Pichia angusta* (Yeast) (*Hansenula polymorpha*) | 15-50 |
| 16 | 48 | Dihydroxyacetone synthase (EC 2.2.1.3) | *Ogataea methanolica* (Yeast) (*Pichia methanolica*) | 25-30 |
| 17 | 49 | Dihydroxyacetone synthase (DHAS) (EC 2.2.1.3) (Formaldehyde transketolase) (Glycerone synthase) | *Candida boidinii* (Yeast) | 25-30 |
| 18 | 50 | Uncharacterized protein | *Kuraishia capsulata* CBS 1993 | 24-26 |
| 19 | 51 | Dihydroxyacetone synthase 1 (EC 2.2.1.3) | *Komagataella pastoris* (Yeast) (*Pichia pastoris*) | 25-35 |

TABLE 1-continued

| SEQ ID NOS: Protein | Nucleic Acid | Protein names | Source organism | Growth temperature (° C.) |
|---|---|---|---|---|
| 20 | 52 | Dihydroxyacetone synthase | *Diaporthe ampelina* | 15-35 |
| 21 | 53 | Dihydroxy-acetone synthase, putative | *Aspergillus fumigatus* Z5 | 37-50 |
| 22 | 54 | DAS-like protein | *Ogataea methanolica* (Yeast) (*Pichia methanolica*) | 25-30 |
| 23 | 55 | Formaldehyde transketolase (EC 2.2.1.3) | *Scedosporium apiospermum* | 30-35 |
| 24 | 56 | Dihydroxyacetone synthase | *Aspergillus terreus* (strain NIH 2624/FGSC A1156) | 35-40 |
| 25 | 57 | Formaldehyde transketolase (EC 2.2.1.3) | CBS 393.64 | 45 |
| 26 | 58 | Transketolase | *Exophiala aquamarina* CBS 119918 | 24-30 |
| 27 | 59 | Dihydroxyacetone synthase | *Magnaporthe oryzae* (strain P131) (Rice blast fungus) (*Pyricularia oryzae*) | 26-28 |
| 28 | 60 | Transketolase | *Verruconis gallopava* | 37 |
| 29 | 61 | DEHA2F00968p | *Debaryomyces hansenii* (strain ATCC 36239/CBS 767/JCM 1990/NBRC 0083/IGC 2968) (Yeast) (*Torulaspora hansenii*) | 25-35 |
| 30 | 62 | Transketolase | *Fonsecaea erecta* | 27-37 |
| 31 | 63 | Uncharacterized protein | *Baudoinia compniacensis* (strain UAMH 10762) (Angels' share fungus) | 26-30 |
| 32 | 64 | Dihydroxyacetone synthase | *Mycobacterium* sp. (strain DSM 3803/JC1) | 30 |

*SEQ ID NO: 65 corresponds to an optimized nucleotide (codon) sequence of Das gene from *Pichia angusta*.

Said second enzyme (e.g., the Das or transketolase enzyme) may be e.g., a (Das or transketolase) enzyme from a yeast, fungus or bacterium, more particularly from a yeast or fungus, more particularly from a yeast.

Said second enzyme may e.g., be a yeast or fungal enzyme (more particularly a yeast enzyme), which is not naturally comprised or expressed in bacteria.

Said yeast enzyme may e.g., be a (Das or transketolase) enzyme from a yeast chosen in the following list of yeasts:
*Pichia*,
*Candida*,
*Kuraishia*,
*Komagataella*, and
*Debaryomyces*.

Said yeast enzyme may e.g., be a (Das or transketolase) enzyme from a yeast chosen in the following list of yeasts:
*Pichia angusta*,
*Pichia methanolica*,
*Candida boidinii*,
*Kuraishia capsulata* (more particularly strain CBS 1993),
*Komagataella pastoris*, and
*Debaryomyces hansenii* (more particularly strain ATCC 36239/CBS 767/JCM 1990/NBRC 0083/IGC 2968).

Said yeast enzyme may e.g., be a *Pichia* Das enzyme, more particularly a *Pichia angusta* das enzyme.

Said fungal enzyme may e.g., be a (Das or transketolase) enzyme from a fungus chosen in the following list of fungi:
*Diaporthe*,
*Aspergillus*,
*Scedosporium*,
*Rasamsonia*,
*Exophiala*,
*Magnaporthe*,
*Verruconis*,
*Fonsecaea*, and
*Baudoinia*.

Said fungal enzyme may e.g., be a (Das or transketolase) enzyme from a fungus chosen in the following list of fungi:
*Diaporthe ampelina*,
*Aspergillus fumigatus* (more particularly strain Z5),
*Scedosporium apiospermum*,
*Aspergillus terreus* (more particularly strain NIH 2624/FGSC A1156),
*Rasamsonia emersonii* (more particularly strain CBS 393.64),
*Exophiala aquamarina* (more particularly strain CBS 119918),
*Magnaporthe oryzae* (more particularly strain 70-15/ATCC MYA-4617/FGSC 8958, or strain P131 or strain Y34),
*Verruconis gallopava*,
*Fonsecaea erecta*, and
*Baudoinia compniacensis* (more particularly strain UAMH 10762).

Said bacterial enzyme may e.g., be a (Das or transketolase) enzyme from *Mycobacterium* sp.

More particularly, said second enzyme may e.g., comprise (or consists of) the amino acid sequence of
a *Pichia das* enzyme, more particularly a *Pichia angusta* Das enzyme, more particularly the *Pichia angusta* Das enzyme of SEQ ID NO: 15 (or a sequence, which is at least 50% identical to SEQ ID NO: 15), or
a yeast enzyme, wherein the amino acid sequence of said yeast enzyme comprises a sequence, which is any one from among SEQ ID NOs: 16-19, 22 and 29 (or a sequence, which is at least 50% identical to any one of these SEQ ID NOs), and wherein said yeast enzyme has retained a dihydroxyacetone synthase activity [more particularly, a yeast dihydroxyacetone synthase enzyme, the amino acid sequence of which comprises a sequence which is any one from among SEQ ID NOs: 16-19, 22 and 29, or a sequence, which is at least 50% identical to any one of these SEQ ID NOs], or of
a fungal enzyme, wherein the amino acid sequence of said fungal enzyme comprises a sequence, which is any one from among SEQ ID NOs: 20-21, 23-28 and 30-32, or a sequence, which is at least 50% identical to any one of these SEQ ID NOs, and wherein said fungal enzyme has retained a dihydroxyacetone synthase activity [more particularly, a fungal dihydroxyacetone synthase enzyme, the amino acid sequence of which comprises a sequence which is any one from among SEQ ID NOs:

16-19, 22 and 29, or a sequence, which is at least 50% identical to any one of these SEQ ID NOs].

The amino acid sequence of said second enzyme may consist of e.g., 618-875 amino acids, e.g., 700-810 amino acids (e.g., 703-808 amino acids), e.g., 700-760 amino acids (e.g., 703-754 amino acids), e.g., of 705-710 amino acids, e.g., of 705, 706, 707, 709 or 710 amino acids, e.g., of 710 amino acids.

Said yeast enzyme may e.g., an enzyme from one of the above-captioned lists of yeasts.

Said fungal enzyme may e.g., an enzyme from one of the above-captioned lists of fungi.

Throughout the application, the phrase "at least 50% identical" specifically encompasses the meanings of "at least 60% identical", "at least 70% identical", "at least 80% identical", "at least 85% identical", "at least 90% identical", "at least 91% identical", "at least 92% identical", "at least 95% identical", "at least 96% identical", "at least 99% identical" or "100% identical", e.g., "at least 80% identical" or "at least 90% identical".

Throughout the application, the feature of sequence identity is intended in accordance with its ordinary meaning in the field. It notably relates the percentage of sequence identity that is computed (on the best alignment) over the longest of the two sequences.

For example, said second enzyme may be e.g., a (Das or transketolase) enzyme from yeast or fungus, more particularly from yeast, more particularly from *Pichia*, more particularly from *Pichia angusta*, and said first enzyme may be e.g., a (Ald or Alo, more particularly a Mdh or Mox, more particularly a Mdh, more particularly a NAD-dependent Mdh) enzyme from a bacterium, more particularly from *Bacillus* (more particularly from *Bacillus methanolicus* or *Bacillus coagulans*, more particularly from *Bacillus methanolicus*).

More particularly, said second enzyme may comprise the sequence of SEQ ID NO: 15 and said first enzyme may comprise the sequence of SEQ ID NO: 1.

The non-naturally occurring microorganism, which comprises, or is expressing, or has been engineered to comprise or express, said first and second enzymes, may e.g., be a bacterium, a yeast or a fungus, more particularly a bacterium or a yeast, more particularly a bacterium.

Said bacterium may e.g., be
*Escherichia* (more particularly *Escherichia coli*), *Corynebacterium* (more particularly *Corynebacterium glutanicum*) or *Bacillus* (more particularly *Bacillus methanolicus* or *Bacillus subtilis*, more particularly *Bacillus* other than *B. methanolicus*, e.g., *Bacillus subtilis*),
more particularly *Escherichia* (more particularly *Escherichia coli*) or *Corynebacterium* (more particularly *Corynebacterium glutanicum*),
more particularly *Escherichia* (more particularly *Escherichia coli*).

Said yeast may e.g., be *Saccharomyces* (more particularly *Saccharomyces cerevisiae*) or *Pichia* (more particularly *Pichia* other than *Pichia pastoris*; more particularly, *Pichia angusta*), more particularly *Saccharomyces* (more particularly *Saccharomyces cerevisiae*).

Said fungus may e.g., be *Yarrowia*, more particularly *Yarrowia lipolytica*.

More particularly, the non-naturally occurring microorganism, which comprises, or is expressing, or has been engineered to comprise or express, said first and second enzymes, is

*Escherichia* (more particularly *Escherichia coli*),
*Corynebacterium* (more particularly *Corynebacterium glutanicum*),
*Bacillus*, more particularly *Bacillus* other than *B. methanolicus* (e.g., *B. subtilis*),
*Saccharomyces* (more particularly *Saccharomyces cerevisiae*), or
*Yarrowia* (more particularly *Yarrowia lipolytica*).

More particularly, the non-naturally occurring microorganism, which comprises, or is expressing, or has been engineered to comprise or express, said first and second enzymes, is
*Escherichia* (more particularly *Escherichia coli*),
*Corynebacterium* (more particularly *Corynebacterium glutanicum*), or
*Saccharomyces* (more particularly *Saccharomyces cerevisiae*).

More particularly, said microorganism may not be a natural methylotroph, i.e., it may be a microorganism, which, in the absence of engineering (i.e., the engineering which provides methylotrophy by expression of said first and second enzymes), is not a methylotrophic microorganism. For example, said microorganism may be a microorganism other than *Pichia pastoris*.

Said microorganism may be an aerobic microorganism or an anaerobic microorganism, more particularly an aerobic microorganism.

Said non-naturally occurring microorganism may use a C1 compound (i.e., a compound, wherein the number of carbon atoms is one), such as methanol (MeOH), as carbon source. Throughout the application, the phrase "CX compound(s)" wherein X is a positive integer (e.g., C1, C3, C5 or C6 compound(s)) is intended in accordance with its general meaning in the field, and refers to compound(s), wherein the number of carbon atoms is the value of said integer X (e.g., one, three, five or six carbon atom(s)).

More particularly, said non-naturally occurring microorganism metabolizes C1 compounds, such as methanol (MeOH), more particularly such as methanol (MeOH) and formaldehyde (HCOH).

More particularly, said non-naturally occurring microorganism may use methanol to produce formaldehyde (the reaction being catalyzed by said first enzyme, e.g., the enzyme Mdh).

More particularly, said non-naturally occurring microorganism may use formaldehyde to produce C3 compounds, such as dihydroxyacetone (DHA) or glyceraldehyde 3-phosphate (GA3P), more particularly DHA (the reaction being catalyzed by said second enzyme, e.g., the enzyme Das). For example, said non-naturally occurring microorganism may incorporate formaldehyde into an acceptor of C1 compound, more particularly into a C5 compound, such as xylulose 5-phosphate (Xu5P), to produce C3 compounds such as DHA and GA3P.

C3 compounds, such as DHA and GA3P, may be used by said non-naturally occurring microorganism to produce C6 compound(s), such as fructose 6-phosphate (F6P).

The non-naturally occurring microorganism of the application may advantageously allow for the regeneration of the acceptor of C1 compound, e.g., of the C5 compound, such as Xu5P. For example, GA3P may be used by said non-naturally occurring microorganism to recycle the acceptor of C1 compound (cf. e.g., FIG. 1).

C3 compounds, such as DHA, may be used by said non-naturally occurring microorganism to produce C3 compounds containing phosphate, such as one or several of dihydroxyacetone phosphate (DHAP), 1-3bis phosphoglycerate (13BPG) and phosphoenolpyruvate (PEP).

Please see the metabolic diagram shown in FIG. 1.

Hence, e.g., when provided with a C1 compound as sole or main carbon source, said non-naturally occurring microorganism may comprise or produce one or several compounds chosen from among C1 compound(s) such as formaldehyde,
C5 compound(s) such as Xu5P,
C3 compound(s) such as DHA and GA3P, more particularly DHA, phosphate-containing C3 compound(s) such as DHAP, 13BPG and PEP, and
C6 compound(s) such as F6P.

More particularly, said non-naturally occurring microorganism may comprise or produce one or several compounds chosen from among formaldehyde,
Xu5P,
DHA and GA3P, more particularly DHA
DHAP, 13BPG, and PEP, and
F6P.

More particularly, said non-naturally occurring microorganism may at least comprise or produce formaldehyde and DHA.

More particularly, said non-naturally occurring microorganism may at least comprise or produce formaldehyde, DHA and GA3P.

More particularly, said non-naturally occurring microorganism may at least comprise or produce formaldehyde, DHA and PEP.

More particularly, said non-naturally occurring microorganism may at least comprise or produce formaldehyde, DHA, GA3P and PEP Said non-naturally occurring microorganism may further comprise or produce one or several compounds chosen from among erythrose 4 phosphate (E4P), sedoheptulose 7 phosphate (S7P), ribose 5 phosphate (R5P) and ribulose 5 phosphate (Ru5P).

In addition to said first and second enzymes (e.g., in addition to Mdh and Das enzymes), said non-naturally occurring microorganism may further comprise one or several enzymes chosen from among dihydroxyacetone kinase (DHAK),
triosephosphate isomerase,
phosphoglycerate kinase,
fructose 6 aldolase (FSA),
transketolase 2 (TKT2),
ribulose 5 phosphate 3 epimerase (RPE),
ribose 5 phosphate isomerase (RPI),
transketolase 1 (TKT1), and
transaldolase (TAL),
fructose 1,6-bisphosphate aldolase,
transaldolase, and
sedoheptulose-1,7-bisphosphatase.

More particularly, said non-naturally occurring microorganism may further comprise one or several enzymes chosen from among dihydroxyacetone kinase (DHAK),
triosephosphate isomerase,
phosphoglycerate kinase,
fructose 6 aldolase (FSA),
transketolase 2 (TKT2), and
ribulose 5 phosphate 3 epimerase (RPE).

More particularly, said non-naturally occurring microorganism may further comprise at least one transketolase 2 (TKT2) enzyme.

Said non-naturally occurring microorganism may be a microorganism, wherein the (naturally occurring) pathway for formaldehyde detoxification (e.g., the frmA gene) has been partially or fully deleted, has been inactivated, is absent or is inactivated,
or, to the contrary,
wherein said pathway is present and active.

Said first and second enzymes are coded by or expressed from (more particularly recombinantly expressed from) from a first nucleic acid and from a second nucleic acid, respectively.

Said first and second nucleic acid are contained in said non-naturally occurring microorganism (more particularly in the cytoplasmic compartment of said non-naturally occurring microorganism), where they are translated into said first and second enzymes, respectively.

The application thus describes a non-naturally occurring microorganism, which comprises, is translating, or has been engineered to comprise or translate a first nucleic acid coding for said first enzyme, and
a second nucleic acid coding for said second enzyme, wherein at least one of said first and second enzymes, or at least one of said first and second nucleic acids, is heterologous to said non-naturally occurring microorganism.

Said first and second nucleic acids are contained in the non-naturally occurring microorganism where they are translated into the enzymes they encode, i.e., into said first and second enzymes respectively. The translation of said first and second nucleic acids may each independently from each other be constitutive or inducible, more particularly inducible, for example inducible by isopropyl β-D-1-thiogalactopyranoside (IPTG).

Examples of nucleic acid sequences, which codes for said first enzyme, notably comprise the nucleic acids, which code for a sequence from among SEQ ID NOs: 1-14, more particularly SEQ ID NOs: 1-13, more particularly SEQ ID NOs: 1-4, more particularly SEQ ID NOs: 1-2, more particularly SEQ ID NO: 1. Examples of nucleic acid sequences, which codes for said first enzyme, notably comprise the nucleic acids of SEQ ID NOs: 33-46, more particularly SEQ ID NOs: 33-45, more particularly SEQ ID NOs: 33-36, more particularly SEQ ID NOs: 33-34, more particularly SEQ ID NO: 34.

Examples of nucleic acid sequences, which codes for said second enzyme, notably comprise the nucleic acids, which code for a sequence from among SEQ ID NOs: 15-32, more particularly SEQ ID NOs: 15-18, more particularly SEQ ID NOs: 15-16, more particularly SEQ ID NO: 15. Examples of nucleic acid sequences, which codes for said second enzyme, notably comprise the nucleic acids of SEQ ID NOs: 47-65, more particularly SEQ ID NOs: 47-50 and 65, more particularly SEQ ID NOs: 47-48 and 65, more particularly SEQ ID NOs: 47 and 65, more particularly SEQ ID NO: 47 and more particularly SEQ ID NO: 65

Said first and second nucleic acids are each independently from each other contained in the same nucleic acid molecule (e.g., in the same chromosome or in the same plasmid insert), or are contained in distinct nucleic acid molecules (e.g., in two distinct plasmid inserts, or in two separate plasmids). For example, said first and second nucleic acids are each independently from each other contained in a nucleic acid vector (e.g., in a plasmid), which is contained in (or has been recombinantly inserted into) said naturally-occurring microorganism, or
in the chromosome of said non-naturally occurring microorganism.

The term "nucleic acid vector" is herein intended in accordance with its ordinary meaning in the field. It notably encompasses any engineered or recombinant nucleic acid construct, which may carry a coding nucleic acid, which may be inserted or introduced in said microorganism and which and allow the expression (transcription and/or translation) of said coding nucleic acid. The nucleic acid vector can thus be viewed an expression vector. The nucleic acid vector can e.g., be a a plasmid, virus, or nucleic acid fragment, more particularly a plasmid. More particularly, the nucleic acid vector is a DNA vector, more particularly a plasmid. The nucleic acid vector, more particularly the plasmid, may comprise at least one promoter sequence and at least one terminator sequence (e.g., BGH polyadenylation sequence), and optionally an origin of replication (ori) sequence, and optionally a selection or selectable marker sequence.

Said first and second nucleic acids may either be both contained in the same nucleic acid vector (e.g., in a plasmid), or may each be contained in separate (or different) nucleic vectors (e.g., in two separate or different plasmids). When they are contained in a nucleic acid vector (e.g., a plasmid) or in the chromosome, the first and second nucleic acids are each contained as a nucleic acid insert operably linked for translation of the enzyme they respectively encode.

Said first and second nucleic acids are contained in said non-naturally occurring microorganism in a first copy number and in a second copy number. Said first and second copy numbers can be in any proportion that the skilled person may found appropriate, e.g., a proportion of 20-80% (more particularly of 30-70%, more particularly of 40-60%) for said first copy number relative to said second copy number.

The application also describes a kit (or functional association), which contains
said first enzyme and said second enzyme, or which contains
said first nucleic acid and said second nucleic acid,
wherein said kit (or functional association) is for simultaneous, sequential or separate use in the engineering of a microorganism, more particularly for the recombinant engineering of a microorganism, more particularly for the genetic engineering of a microorganism, wherein at least one of said first and second enzymes, or at least one of said first and second nucleic acids, is heterologous to said microorganism.

The application also describes a method of producing a methylotrophic microorganism, or a microorganism, which has acquired the capacity metabolizing methanol (to produce energy and/or metabolites, such as PEP). Said method comprises engineering, more particularly recombinantly engineering, said microorganism,
to (recombinantly) express said first and second enzyme, or
to comprise said first and second nucleic acids (for expression, more particularly for recombinant expression, of said first and second enzymes),
wherein at least one of said first and second enzymes, or at least one of said first and second nucleic acids, is heterologous to said microorganism.

The term "engineering" or "recombinantly engineering" is intended in accordance with its ordinary meaning in the field. It notably encompasses
inserting or introducing at least one or each of said first and second enzymes into said microorganism, or
transfecting, infecting, transforming or otherwise inserting at least one or each of said first and said second nucleic acids (for expression, more particularly for recombinant expression, of at least one or each of said first and second enzymes).

The features, which have been described in relation to the first and second enzymes, to the first and second nucleic acids, or to the non-naturally occurring microorganism apply to said kit and method, mutatis mutandis.

The non-naturally occurring microorganism of the application can use methanol as carbon source, and therefore can be used as a biotechnological platform for producing a compound of industrial interest (e.g., as chemical compound, as fuel compound or as healthcare or medical compound).

The non-naturally occurring microorganism may produce, more particularly recombinantly produce, or may have been (further) engineered, more particularly recombinantly (further) engineered, to produce said compound [e.g., as a metabolite].

Said non-naturally occurring microorganism may comprise, more particularly recombinantly comprise, the reactants or products which are required for said microorganism to metabolize said compound. For example, said non-naturally occurring microorganism may have been engineered, more particularly recombinantly engineered, to comprise and express the enzyme(s) and any cofactor that may be required to build a metabolic pathway, which produces said compound.

Said compound may be a naturally occurring compound or a non-naturally occurring compound.

Said compound may e.g., be a compound, which requires NADH for its production.

Said compound may e.g., be an antibiotic, an amino acid, a vitamin, a pyrazine, a diamine, an organic acid, an alcohol, a butanol, an alkane, a carboxylic acid, a fatty acid a pyrimidine, a polymer, butanediol, isobutene, propylene or butadiene.

More particularly, said compound may e.g., be butanediol, isobutene, propylene or butadiene.

Said compound may e.g., be riboflavin, shikimate, L-phenylalanine, L-tryptophan, L-tyrosine, phenol, deoxyviolacein, p-aminobenzoic acid, 1,3-propanediol, 1,2-propanediol, L-serine, D-lactate, ethanol, L-lactate, L-valine, L-alanine, isobutanol, panthothenate, butanol, arteminisin, 1,4-butanediol, isopropanol, butyrate, fatty acid(s), taxadien, hexanol, poly-hydroxyalkanoate(s), beta-carotene, itaconate, L-lysine, L-threonine, L-isoleucine, cadaverine, 1-propanol, 1-butanol, ectoine, putrescine, 4OH-proline, succinate or malate (notably when said non-naturally occurring microorganism is a bacterium, such as *E. coli*; cf. Becker and Whittmann 2015).

Said compound may e.g., be L-histidine, L-tryptophan, L-phenylalanine, L-tyrosine, 1,2-propanediol, L-serine, D-serine, L-alanine, L-valine, D-lactate, isobutanol, L-leucine, L-oxoisovalerate, 2-oxoisocaproate, ethanol, panthothenate, pyrazine(s), oleic acid, palmitic acid, carotenoid(s), poly-hydroxybutyrate, L-lysine, cadaverine, L-isoleucine, L-threonine, ectoine, D-lysine, L-methionine, butanol, 1-propanol, glycolate, L-glutamate, L-arginine, L-ornithine, gamma-aminobutyrate, L-citruline, putrescine, L-proline, D-ornithine, D-arginine, 4OH-proline, or succinate (notably when said non-naturally occurring microorganism is a bacterium, such as *Corynebacterium glutamicum*; cf. Becker and Whittmann 2015).

Said compound may e.g., be resveratrol, naringenin, vanillin, 1,3-propanedoil, 2,3-butanedoil, L-lactate, ethanol, isobutanol, butanol, FAME, beta-carotene, lycopene, astaxanthin, zeaxanthin, itaconate, succinate or malate (notably when said non-naturally occurring microorganism is a yeast, such as *S. cerevisiae*; cf. Becker and Whittmann 2015).

The application also relates to a cell culture, more particularly a cell culture medium, which comprises at least one non-naturally occurring microorganism of the application, as well as to a method of producing a compound of interest, which comprises placing a non-naturally occurring microorganism of the application in a cell culture, more particularly a cell culture medium, and cultivating it under conditions that allow for production of said compound by said non-naturally occurring microorganism.

Said cell culture, more particularly a cell culture medium, may comprise methanol. Said cell culture, more particularly a cell culture medium, may further comprise at least one sugar (e.g., glucose), or, on the contrary, may comprise no carbon source other than methanol.

More particularly, the application relates to a method of production of a compound of interest (e.g., a compound of industrial interest as described above), which comprises cultivating a non-naturally occurring microorganism of the application in a culture medium containing methanol (e.g., wherein the methanol contributes to at least 40% (or at least 50%, or at least 60%) of the carbon source in the medium), wherein said non-naturally occurring microorganism produces said compound of interest as a metabolite, and collecting the compound produced by said non-naturally occurring microorganism.

Said method of production may be an in vivo or in vitro method of production, more particularly an in vitro method.

In the application, unless specified otherwise or unless a context dictates otherwise, all the terms have their ordinary meaning in the relevant field(s).

The term "comprising", which is synonymous with "including" or "containing", is open-ended, and does not exclude additional, unrecited element(s), ingredient(s) or method step(s), whereas the term "consisting of" is a closed term, which excludes any additional element, step, or ingredient which is not explicitly recited.

The term "essentially consisting of" is a partially open term, which does not exclude additional, unrecited element (s), step(s), or ingredient(s), as long as these additional element(s), step(s) or ingredient(s) do not materially affect the basic and novel properties of the invention.

The term "comprising" (or "comprise(s)") hence includes the term "consisting of" ("consist(s) of"), as well as the term "essentially consisting of" ("essentially consist(s) of"). Accordingly, the term "comprising" (or "comprise(s)") is, in the application, meant as more particularly encompassing the term "consisting of" ("consist(s) of"), and the term "essentially consisting of" ("essentially consist(s) of").

In an attempt to help the reader of the application, the description has been separated in various paragraphs or sections. These separations should not be considered as disconnecting the substance of a paragraph or section from the substance of another paragraph or section. To the contrary, the description encompasses all the combinations of the various sections, paragraphs and sentences that can be contemplated.

Each of the relevant disclosures of all references cited herein is specifically incorporated by reference. The following examples are offered by way of illustration, and not by way of limitation.

EXAMPLES

Example 1: Identification and Selection of Combinations of Genes Encoding Enzyme 1 and Enzyme 2

Genes encoded for enzyme 1 and genes encoded for enzyme 2 were selected by protein sequence similarity search using Uniref50% (Boris et al. 2015, Bioinformatics, 31:6). The protein sequences SEQ ID NO: 1 and SEQ ID NO: 15 were used as template (see Table 3). These tools give a list of similar sequences that have at least 50% sequence identity to, and 80% overlap with, the longest sequence of the list. The resulting lists contained 230 sequences of genes encoding enzyme 2 and 732 of genes encoding enzyme 1. CD-Hit (http://www.bioinformatics.org/cd-hit/) was then used to hierarchically cluster close homologous sequences together, identify sub-families and select sequences representative of each sub-family. In total 19 representative sequences were found for genes encoding enzyme 1 and 27 for genes encoding enzyme 2. Sequences originating from non-mesophilic and strictly anaerobic microorganisms were removed. In total 12 sequences out of 19 were conserved for genes encoding enzyme 1 mdh and 17 out of 27 for genes encoding enzyme 2. Adh gene from *Geobacillus stearothermophilus* and mox gene from *Pichia angusta* encoding enzyme 1; Das gene form *Mycobacterium* sp. and optimized nucleotide sequence (SEQ ID NO: 65) of Das gene from *Pichia angusta* encoding enzyme 2 were also added to the list (Table 1). All the selected sequences were used to generate a combinatorial library of 266 (i.e. 14 for enzyme 1*19 for enzyme 2) combinations of genes to be tested.

Variants are constructed as described in example 2 below. Methanol incorporation is measured in each variant using dynamic $^{13}C$ labelling experiment as described in example 3 below. First order time constants (T50) for incorporation of $^{13}C$ into phosphoenolpyruvate (PEP) and the maximal achieved labelling fraction in this metabolite is determined for each mdh/mox and das combination. PEP is an informative metabolite because it is among the first intermediates following C1 fixation and because it provides information on precursor regeneration since incorporation of more than one atom of $^{13}C$ into PEP can only be obtained via recycling of the acceptor carbon unit (i.e., xylulose 5-phosphate or Xu5P).

Example 2: Expression of a Combination of mdh/das Genes in *E. coli*

Bacterial Strains and Plasmids.

The strains constructed in this example are listed in Table 2 below. *Escherichia coli* BW25113 wild type strain and *E. coli* BW25113 cell lacking the formaldehyde dehydrogenase gene (frmA) were obtained from the KEIO collection (Baba et al. 2006).

Modified plasmid pSEVA131 containing an expression system lacIq-Ptrc was used for heterologous expression of dihydroxyacetone synthase (das) from *Pichia angusta*.

The plasmid pSEVA424 (Silva-Rocha et al. 2013) was used for heterologous expression of the methanol dehydrogenase gene (mdh2) from *Bacillus methanolicus* strain PB1.

TABLE 2

E. coli strains

| Strain | Abbreviation | Reference |
| --- | --- | --- |
| Escherichia coli BW25113 | BW | Datsenko and Wanner 2000 |
| E. coli BW25113 ΔfrmA | BW-FRMA | Baba et al. 2006 |
| E. coli BW25113 (p131-p424) | BW-p131-p424 | this example |
| E. coli BW25113 (p424-mdh2)(p131-das) | BW-MDH2-DAS | this example |
| E. coli BW25113ΔfrmA (p131-p424) | BW-FRMA-p131-p424 | this example |
| E. coli BW25113ΔfrmA (p424-mdh2)(p131-das) | BW-FRMAMDH2-DAS | this example |

Recombinant DNA Work.

The enzymes for recombinant DNA work were obtained from NEW ENGLAND BIOLABS® Inc. (240 County Road, Ipswich, MA 01938-2723, U.S.A.). Plasmids were isolated with the QIAPREP® SPIN MINIPREP kit (QIAGEN®, QIAGEN Strasse 1, DE-40724 Hilden, Germany). E. coli was transformed by the Rubidium Chloride method (Hanahan 1983). Routine methods like restriction were carried out according to standard protocols (Sambrook et al. 1989). For heterologous expression, the genes mdh2 and das were synthetized, verified by sequencing and integrated into the expression vector by GENESCRIPT® (860 Centennial Avenue, Piscataway, NJ 08854, U.S.A.).

TABLE 3

| | Nucleic acid SEQ ID NO: | Protein SEQ ID NO: |
| --- | --- | --- |
| Das sequence (from Pichia angusta) | 47 | 15 |
| Mdh2 sequence (from Bacillus methanolicus strain PB1) | 33 | 1 |

The mdh2-PB1 nucleic acid sequence (SEQ ID NO: 33) and the encoded Mdh2 amino acid sequence (SEQ ID NO: 1) have been described in WO 2013/110797 in the names of SINVENT AS et al.

B. methanolicus strain PB1 is available under NCIMB 13113.

Example 3: Methanol Incorporation into Engineered E. coli Strains

For the labelling experiments we used the E. coli strains described in Table 1 above. E. coli BW25113 (p131-p424) and E. coli BW25113ΔfrmA (p131-p424) were used as negative control. All the cultivations were performed at 37° C. E. coli strains were freshly inoculated from a glycerol stock on a LB (10 g/l of tryptone, 5 g/l of yeast extract and 10 g/l of NaCl) liquid medium for six hours. The LB cultures were used to inoculate liquid pre-cultures containing minimal synthetic medium composed of 20 mM of xylose, 17.4 g/l $Na_2HPO_4 \cdot 12H_2O$, 3.03 g/l of $KH_2PO_4$, 0.51 g/l of NaCl, 2.04 g of $NH_4Cl$, 0.49 g/l of $MgSO_4$, 4.38 mg/l of $CaCl_2$), 15 mg/l of $Na_2EDTA \cdot 2H_2O$, 4.5 mg/l of $ZnSO_4 \cdot 7H_2O$, 0.3 mg/l of $CoCl_2 \cdot 6H_2O$, 1 mg/l of $MnCl_2 \cdot 4H_2O$, 1 mg/l of $H_3BO_3$, 0.4 mg/l of $Na_2MoO_4 \cdot 2H_2O$, 3 mg/l of $FeSO_4 \cdot 7H_2O$ and 0.3 mg/l of $CuSO_4 \cdot 5H_2O$, 0.1 g/l of thiamine (i.e. M9-xylose). A final concentration of 0.1 mM of IPTG was used as inducer and 50 μg/ml of spectinomycin and 100 μg/ml of ampicillin were added in the medium as resistant markers. Cultures were inoculated at a final concentration of 36 mg $CDW.L^{-1}$. For the labelling experiments cells were centrifuged 5 min, 4400 g at room temperature and re-suspended in minimal synthetic medium plus IPTG but without unlabeled xylose and antibiotics at a final concentration between 0.18 and 0.36 g/l. To check for incorporation, one cultivation sample was taken before addition of $^{13}C$-methanol (i.e., zero minute time point), then 1M (final concentration) $^{13}C$-methanol was added and cultivation samples were taken at 3,6, 10 and 690 minutes. In order to quench the metabolic activity and extract the intracellular metabolites, cultivation samples were dispensed into a cold (−20° C.) solution of acetonitrile/methanol/0.1M formic acid (40/40/20 vol/vol). Extracted samples were evaporated in a Rotavapor (Buchi, Switzerland) for approximately 15 hours until complete dryness. The samples were then re-dissolved in 120 μl of ultrapure water and stored at −20° C. until analysis. The labeling patterns of intracellular metabolites were measured using a DIONEX™ ICS 2000 system (DIONEX™, Sunnyvale, U.S.A.) coupled to a triple quadrupole QTRAP® 4000 mass spectrometer (APPLIED BIOSYSTEMS™, Foster City, U.S.A.).

Results

When 13C-methanol was added as the only substrate (FIG. 2), no labeling into the mass isotopomer M1 fraction (i.e., in the fraction of molecules wherein one carbon atom is labeled) was detected in the negative controls, whereas labeling was detected in several metabolites with the recombinant E. coli strains expressing the mdh2 and das genes. The disruption of the native formaldehyde oxidation pathway by deleting the formaldehyde dehydrogenase (frmA) gene slightly improved formaldehyde assimilation. These data clearly demonstrate that the recombinant methylotrophic pathway operates in vivo, leading to assimilation of methanol into central carbon metabolism.

Example 4: Selection of the Best Combinations of Genes Encoding Enzyme 1 and Enzyme 2

A total of 266 variants containing each one of the combinations described in example 1 were constructed according to example 2 using the strain BW-FRMA (see Table 2). To analyze the performance of the different combinations, methanol incorporation was measured in each variant using dynamic $^{13}C$ labelling experiment as described in example 3. Briefly, cells were inoculated in a 96 deep well plates containing 1 ml of M9-xylose, antibiotic and IPTG in each well from a LB pre-cultivation at a final concentration of 36 mg $CDW.L^{-1}$. At mid exponential growth phase, deep well plates were centrifuged 3 min, 5000 g at room temperature and re-suspended in 0.5 ml of M9 medium containing $^{13}C$-methanol, antibiotics and IPTG. In these screening, all the cultivations were performed at 30° C. which is the medium growth temperature of the source microorganisms of the enzymes 2. Samples (120 μl of total broth) were taken at 90 min and dispensed in a 96 deep well plates containing 1 ml of acetonitrile/methanol/0.1M formic acid in each well. Extracted samples were subsequently treated as described in example 3.

Results

FIG. 3 shows the mean isotopic enrichment measured in the PEP for each combination of enzyme 1 and 2. The mean isotopic enrichment is express in % and has been calculated as follow: (0*M0+1*M1+2*M2+3*M3)/3. The highest mean isotopic enrichments were obtained for the combinations containing the genes encoding the enzyme 2 form *P. angusta* (SEQ ID NO: 15) and was maximal for the combination containing the enzyme 2 from *P. angusta* with an optimized nucleotide sequence (i.e. *P. angusta* (Opt), SEQ ID NO: 65). This nucleotide sequence exhibited 78% of identity with the native one. Labelling was also observed for combinations containing the gene encoding the enzyme 2 of *K. capsulata* (SEQ ID NO: 18) and *F. erecta* (SEQ ID NO: 30). Interestingly, in all the aforementioned combinations, labelling was observed whatever the nature of the enzyme 1 suggesting that enzyme 2 is the limiting step for the methanol assimilation. No labelling was observed for all the combinations containing the gene encoding the enzyme 1 of *P. angusta* (SEQ ID NO: 14) and *Vibrio* sp (SEQ ID NO: 11) suggesting that these enzymes are not functional. Overall the best combination are the ones containing the gene encoding enzyme 1 from *A. gerneri* (SEQ ID NO: 4) and *Burkholderia* (SEQ ID NO: 3) together with the optimized version of the gene encoding the enzyme 2 from *P. angusta*. In these combinations, labelling is found at respectively 31 and 32% in M1 and 17 and 13.7% in M2 of the PEP. In addition, trace of labelling were found in the M3.

Example 5: Compatibility of Optimum Temperatures for Enzyme 1 and 2

Selected genes encoding for enzyme 1 are originating from microorganisms growing in a range comprise 10 and 50° C. while the ones from enzyme 2 are comprised between 15-50° C. (Table 1). This means that optimum temperature of some combinations of enzyme 1 and 2 can be quiet distant (e.g. enzyme 1 from the genus *B. methanolicus* with enzyme 2 from *B. compniacensis*). In addition, all the combinations have been tested at 30° C. (See Example 4). This means that the activity of the enzyme having a higher optimum temperature can be reduced in this condition. Interestingly, for the enzyme 2 from *P. angusta* with an optimized nucleotide sequence (i.e. *P. angusta* (Opt), SEQ ID NO: 65), the highest labelling (i.e. highest in vivo activity) is observed when combined with an enzyme 1 having a close growth temperature. This is the case for encoding enzyme 1 from *A. gerneri* (SED ID NO: 4) and *Burkholderia* (SEQ ID NO: 3). Consistently, the labelling is lower when combined with an enzyme 1 having an growth temperature around 50° C. (Table 1 and FIG. 3). This is the case for instance for the enzyme 1 originating from *Bacillus methanolicus*.

Example 6: Enhancing Activity of the Enzyme 2 by Semi-Random Mutagenesis Approach Previous results described in example 4 demonstrated that enzyme 2 is crucial in methanol assimilation. The enzyme 2 are transketolases which are a family of dimeric enzymes (EC=2.2.1.1) thiamine pyrophosphate (TPP) dependant. More precisely enzyme 2 are formaldehyde transketolase (EC=2.2.1.3) (BRENDA-EC 2.2.1.3, 2018). Transketolases catalyse two reactions: cleavage of a C—C bond of the donor substrate and the transfer of this two carbons block formed onto an acceptor substrate. There are various donor substrates, such as fructose 6-phosphate, sedoheptulose 7-phosphate, erythrulose 4-phosphate (E4P) or xylulose 5-phosphate (Xu5P), as it is the case for the enzyme 2. The acceptors are also numerous: the most typical are ribose 5-phosphate, fructose 6-phosphate or erythrose 4-phosphate, or in the case of the enzyme 2, formaldehyde. To optimize the activity of the enzyme 2, we decided to increase its affinity towards its own substrates (i.e. Xu5P and formaldehyde).

Generation of the 3D Model

Since the crystal structures of the enzyme 2 is not available, the software I-TASSER (https://zhanglab.ccmb.med.u-mich.edu/I-TASSER/) was used to generate a 3D model by homology modelling. This online tool is able to generate a 3D model of a protein based on its sequence and known structural templates from the Protein DataBase (PDB, https://www.rcsb.org/). The amino acid sequence of enzyme 2 of P. Augusta was used as query and I-TASSER predicted a 3D model using the transketolase of *S. cerevisae* (PDB ID: 1NGS) as template with which it shares 40.7% of identity. The generated model was a monomer. To get the full working protein in its homo-dimeric version, this first model was aligned in PyMol with the 1NGS model. Because the model 1NGS model was not complexed with the right carbon donor (i.e. E4P instead of Xu5P), the 3D model of *E. coli* (PDB ID: 2R80) which is complexed with Xu5P, was used to get the position of Xu5P and thus of the catalytic pocket in our model (FIG. 4 A & B).

Selection of the Amino Acid to be Mutated

Using the resulting 3D model, all the amino acids being within 5 Å of the catalytic pocket and being not conserved within the enzyme 2 phylogeny were identified using PyMol (https://pymol.org/2/) and MEGA 7 (https://www.megasoftware.net/), respectively. In total 5 positions were identified (FIG. 4C): the cysteine 203 (C203), the asparagine 277 (N277), the phenylalanine 458 (F458), the glutamic acid 490 (E490) and the asparagine 493 (N493). The histidine 38 (H38) was added to the list because it was previously shown that the corresponding amino acid in the transketoalse of *S. cerevisiae* (H26) enhance the enzymatic activity towards short chain aldehydes when mutated (Hibbert et al. 2007, J Biotechnol. 30: 131 (4): 425-32).

Generation of the Libraries

The generation of the different library was achieved through a megawhop technique, as described previously (Miyazaki, 2011, Methods in Enzymology 498:399-406). Briefly, megaprimers (100-500 bp) containing saturation mutation at the desired positions mutations are generated through classical saturation mutagenesis PCR and are used as primers in a PCR on the whole plasmid containing the gene of interest. Instead of the typical NNN randomisation, we chose the NNK scheme (where N=A/T/G/C and K=G or T) in order to reduce codon redundancy from 64 to 32. By doing so, the library size and the number of STOP codons were reduced. As a result, the transformation capacity needed to cover the whole library is reduced. According to the GLUE online tool (http://guinevere.otago.ac.nz/cgi-bin/aef/glue.pl), for 32 equiprobable variants, full library coverage is achieved when 443 clones are obtained after transformation. For each mutant library we obtained thousands of clones, indicating that all variants were well represented. The quality of the libraries was assessed by sequencing and all the targeted positions showed NNK randomization Five libraries out of the six expected were produced: H38X, C203X, F458X, E490X and N493X (X being any amino acid).

Screening of the Libraries of DAS Variant (DAS*)

In *E. coli*, formaldehyde reacts freely with glutathione and form hydroxymethylglutathione, then converted through a formaldehyde dehydrogenase (GS-FdDH) to S-formylglutathione. Another enzyme, the S-formylgluthatione hydrolase, encoded together with the formaldehyde dehydrogenase on the frmrab operon, convert S-formylglutathione to formate. The formate is finally transformed into $CO_2$ via a formate dehydrogenase. In a Δfrma strain, in which the gene encoding the GS-FdDH is missing, the formaldehyde is no more transformed into $CO_2$ and becomes toxic. In such strain, an efficient enzyme 2 can in theory rescue the growth in presence of formaldehyde by complementing frma. We thus used a Δfrma strain to screen our libraries of variants of enzyme 2.

The growth in the presence of formaldehyde of BW25113 Δfrma strains containing H38X or C203X or F458X or E490X or N493X libraries with the BW25113 Δfrma strain (negative control); BW25113 Δfrma strain carrying the enzyme 2 of from *P. angusta* (positive control) and BW25113 strain carrying the empty plasmid (WT) were compared. Briefly, cells were grown on LB with 1 mM of IPTG at 30° C. When cells reached an optical density at 600 nm=0.6, 1.5 mM of formaldehyde was added. After 24h, cells were re-inoculated into new plates with fresh LB and 1 mM of IPTG, and the process was repeated until the growth in cells containing the libraries was rescued. To identify the mutation responsible for complementation of Δfrma, plasmids were extracted and sequenced. The ability of each gene to complement Δfrma was confirmed by reintroducing the corresponding plasmid. Using this approach and after 2 round of selection the Δfrma strains containing the H38X and the N493X libraries grew respectively as good as the positive control and the WT. In each library, one mutation among the 32 appears to be beneficial on the activity of the enzyme 2. To identify which mutation allowed such phenotype, plasmids is extracted and sequenced. The capacities of complementation of Δfrma of the resulting DAS* are analyzed and their enzymatic characteristics measured.

Example 7: Evolutionary Engineering of Synthetic Methylotrophic *E. coli* Strains The growth of the synthetic methylotrophic *E. coli* strains is boosted by evolutionary engineering. Briefly, it is done by serially sub-cultivating each strain on a medium containing more and more methanol until a clone able to grow faster on pure methanol can be selected. The resulting clone(s) is analyzed using complementary 'omics' approaches and next generation sequencing based technology, to determine complete sets of mutations responsible for the resulting evolved phenotype.

BIBLIOGRAPHIC REFERENCES

Baba et al. (2006) Construction of *Escherichia coli* K-12 in-frame, single-gene knockout mutants: the Keio collection. Molecular systems biology 2:2006 0008. doi: 10.1038/msb4100050

Becker and Whittmann (2015) Advanced biotechnology: metabolically engineered cells for the bio-based production of chemicals and fuels, materials and healthcare products. Angew. Chem. Int. Ed. 54:3328-3350

Hanahan (1983) Studies on transformation of *Escherichia coli* with plasmids. Journal of molecular biology 166 (4): 557-580

Hibbert et al. (2007) Directed evolution of transketolase activity on non-phosphorylated substrates. J Biotechnol. 30: 131 (4): 425-32

Miyazaki K (2011) Chapter seventeen-MEGAWHOP Cloning: A Method of Creating Random Mutagenesis Libraries via Megaprimer PCR of Whole Plasmids. Methods in Enzymology 498:399-406. https://doi.org/10.1016/B978-0-12-385120-8.00017-6

Müller et al. (2015) Engineering *Escherichia coli* for methanol conversion. Metabolic Engineering 28:190-201

Silva-Rocha et al. (2013) The Standard European Vector Architecture (SEVA): a coherent platform for the analysis and deployment of complex prokaryotic phenotypes. Nucleic acids research 41 (Database issue): D666-675. doi: 10.1093/nar/gks1119

Sambrook, Fritsch & Maniatis, T. (1989) Molecular cloning: a laboratory manual. Cold Spring Harbor, New York: Cold Spring Harbor Laboratory Press.

WO 2013/110797 in the names of SINVENT SAS et al.

The invention claimed is:

1. A non-naturally occurring microorganism, which has been engineered to acquire methylotrophy, wherein said microorganism comprises a first enzyme and a second enzyme, wherein said first enzyme is a methanol dehydrogenase (Mdh) enzyme, the nucleic acid sequence of which is selected from the group consisting of: SEQ ID NOs: 34-42 and 45,
  wherein said second enzyme is a dihydroxyacetone synthase (Das) enzyme, the nucleic acid sequence of which is SEQ ID NO: 47 or 65,
  wherein at least one of said first and second enzymes is heterologous to said microorganism, and
  wherein the nucleic acid pair of said first enzyme and said second enzyme is selected from the group consisting of SEQ ID NOs: 36 and 47, 37 and 47, 40 and 47, 34 and 65, 35 and 65, 36 and 65, 37 and 65, 38 and 65, 39 and 65, 40 and 65, 41 and 65, 42 and 65, and 45 and 65.

2. The non-naturally occurring microorganism of claim 1, wherein the nucleic acid pair of said first enzyme and said second enzyme is selected from the group consisting of SEQ ID NOs: 36 and 47, 37 and 47, 40 and 47, 34 and 65, 35 and 65, 36 and 65, 37 and 65, 39 and 65, 41 and 65, and 45 and 65.

3. The non-naturally occurring microorganism of claim 1, wherein the nucleic acid pair of said first enzyme and said second enzyme is selected from the group consisting of SEQ ID NOS: 35 and 65, and 36 and 65.

4. The non-naturally occurring microorganism of claim 1, wherein each of said first and second enzymes is heterologous to said microorganism.

5. The non-naturally occurring microorganism of claim 1, wherein said microorganism is a bacterium, a yeast or a fungus.

6. The non-naturally occurring microorganism of claim 5, wherein said microorganism is a bacterium, a yeast or a fungus, and wherein
  said bacterium is *Escherichia*, *Corynebacterium* or *Bacillus*,
  said yeast is *Saccharomyces* or *Pichia*, and
  said fungus is *Yarrowia*.

7. The non-naturally occurring microorganism of claim 1, wherein said first enzyme and said second enzyme are recombinantly expressed from a first nucleic acid and from a second nucleic acid, respectively, and wherein said first and second nucleic acids are either both contained in a same nucleic acid vector or are each contained in separate or different nucleic vectors.

* * * * *